(12) United States Patent
Keum et al.

(10) Patent No.: US 11,407,745 B2
(45) Date of Patent: Aug. 9, 2022

(54) INDAZOLE DERIVATIVES AND PHARMACEUTICAL COMPOSITION FOR PREVENTING, ALLEVIATING OR TREATING CANCER CONTAINING THE SAME

(71) Applicant: KOREA INSTITUTE OF SCIENCE AND TECHNOLOGY, Seoul (KR)

(72) Inventors: Gyo Chang Keum, Seoul (KR); Ashraf Kareem El-Damasy, Seoul (KR); Hee Won Jin, Seoul (KR); Taek Kang, Seoul (KR); Eun Kyoung Bang, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/897,987

(22) Filed: Jun. 10, 2020

(65) Prior Publication Data

US 2020/0392127 A1    Dec. 17, 2020

(30) Foreign Application Priority Data

Jun. 12, 2019    (KR) .................. 10-2019-0069242

(51) Int. Cl.
| | | |
|---|---|---|
| *C07D 413/12* | (2006.01) | |
| *C07D 403/12* | (2006.01) | |
| *C07D 231/56* | (2006.01) | |
| *A61P 35/02* | (2006.01) | |

(52) U.S. Cl.
CPC ............ *C07D 413/12* (2013.01); *A61P 35/02* (2018.01); *C07D 231/56* (2013.01); *C07D 403/12* (2013.01)

(58) Field of Classification Search
CPC .. C07D 413/12; C07D 403/12; C07D 231/56; A61P 35/02
See application file for complete search history.

(56) References Cited

U.S. PATENT DOCUMENTS 8,114,874 B2    2/2012    Zou et al.

FOREIGN PATENT DOCUMENTS

| KR | 10-2014-0088556 A | 7/2014 |
|---|---|---|
| KR | 10-2015-0067140 A | 6/2015 |

OTHER PUBLICATIONS

Golub et al., Science, vol. 286, Oct. 15, 1999, pp. 531-537.*
Elizabeth Day et al., Inhibition of collagen-induced discoidin domain receptor 1 and 2 activation by imatinib, nilotinib and dasatinib, European Journal of Pharmacology, Oct. 11, 2008, pp. 44-53, vol. 599.
Michael J. Mauro et al. STI571: Targeting BCR-ABL as Therapy for CML, The Oncologist, May 11, 2001, pp.233-238. vol. 6.
Ajay Shrivastava et al. An Orphan Receptor Tyrosine Kinase Family Whose Members Serve as Nonintegrin Collagen Receptors,Molecular Cell ,Dec. 1997, pp. 25-34, vol. 1.
Charles L. Sawyers, M.D et al. Chronic Myeloid Leukemia, The New England Journal of Medicine, Apr. 29, 1999, pp. 1330-1340, vol. 340, No. 17.
Shu-Guang Zhang et al. Recent Advances in Indazole-Containing Derivatives: Synthesis and Biological Perspectives, Molecules, Oct. 26, 2018, pp. 1-41, vol. 23, 2783.
Zhen Zhang et al., Design, Synthesis and Biological Evaluation of 6-(2,6-Dichloro-3,5-dimethoxyphenyl)-4-substituted-1H-indazoles as Potent Fibroblast Growth Factor Receptor Inhibitors, Molecules, Oct. 22, 2016, pp. 1-13. vol. 21, 1407.
Shuxin Li et al., Design, synthesis and biological evaluation of novel acrylamide analogues as inhibitors of BCR-ABL kinase, Bioorganic & Medicinal Chemistry Letters, Jun. 21, 2012, pp. 5279-5282, vol. 22.
E Weisberg et al. AMN107 (nilotinib): a novel and selective inhibitor of BCR-ABL, British Journal of Cancer, May 23, 2006, pp. 1765-1769, vol. 94.
Thomas O'Hare et al., AP24534, a Pan-BCR-ABL Inhibitor for Chronic Myeloid Leukemia, Potently Inhibits the T315I Mutant and Overcomes Mutation-Based Resistance, Cancer Cell, Nov. 3, 2009, pp. 401-412, vol. 16.
Yuanyuan Shan et al., Expanding the structural diversity of Bcr-Abl inhibitors: Dibenzoylpiperazin incorporated with 1H-indazol-3-amine, European Journal of Medicinal Chemistry, Oct. 8, 2015, pp. 139-147, vol. 104.
Peter Canning et al., Structural Mechanisms Determining Inhibition of the Collagen Receptor DDR1 by Selective and Multi-Targeted Type II Kinase Inhibitors, Jmb molecular biology, 2014, pp. 2457-2470, vol. 426.
Feiyang Liu et al., Discovery and characterization of a novel potent type II native and mutant BCR-ABL inhibitor (CHMFL-074) for Chronic Myeloid Leukemia (CML), Oncotarget. Jun. 14, 2016, pp. 45562-45574, vol. 7, No. 29.
Philipp Le Coutre et al.Activity and induction of apoptosis of the tyrosine kinase inhibitor AMN107 in bcr-abl + cell lines and in imatinib resistant primary cells from CML patients, Proc. Am. Assoc. Cancer. Res. May 2015, pp. 1-4, vol. 46.

\* cited by examiner

*Primary Examiner* — Samira J Jean-Louis
(74) *Attorney, Agent, or Firm* — Goldilocks Zone IP Law

(57) ABSTRACT

Disclosed are a compound selected from novel indazole derivatives, pharmaceutically acceptable salts thereof, hydrates thereof and stereoisomers thereof, a method for preparing the compound, and a pharmaceutical composition for preventing, alleviating or treating cancer containing the compound as an active ingredient. The novel indazole derivatives exhibit excellent ABL/DDR1 inhibitory efficacy and anti-proliferative efficacy against cancer cells, specifically blood cancer cells, and inhibitory activity against ABL T315I point mutations, thus being useful for the prevention, alleviation or treatment of cancer, specifically blood cancer, especially chronic myelogenous leukemia.

12 Claims, No Drawings

INDAZOLE DERIVATIVES AND PHARMACEUTICAL COMPOSITION FOR PREVENTING, ALLEVIATING OR TREATING CANCER CONTAINING THE SAME

CROSS-REFERENCE TO RELATED APPLICATION

This application claims, under 35 U.S.C. § 119(a), the priority of Korean Patent Application No. 10-2019-0069242, filed on Jun. 12, 2019, in the Korean Intellectual Property Office, the disclosure of which is incorporated herein by reference in its entirety.

BACKGROUND

(a) Technical Field

The present invention relates to a compound selected from novel indazole derivatives, pharmaceutically acceptable salts thereof, hydrates thereof and stereoisomers thereof, a method for preparing the compound, and a pharmaceutical composition for preventing, alleviating or treating cancer containing the compound as an active ingredient.

(b) Background Art

Chronic myelogenous leukemia (CML), which is a type of hematologic cancer, is a myeloid proliferative disease characterized by the activation of the Philadelphia chromosome, caused by the reciprocal translocation of chromosomes 9 and 22 and BCR-ABL fusion protein tyrosine kinase, the product thereof (*N. Engl. J. Med.,* 340 (17), 1330-1340, 1999). Philadelphia chromosomes are found in more than 95% of CML patients, and BCR-ABL fusion protein has an abnormal tyrosine kinase activity, stronger than that of a normal ABL protein, which is the driving cause for CML and thus represents an important target for drugs.

Imatinib is a BCR-ABL tyrosine kinase inhibitor developed by Novartis International AG and was approved by the FDA as a therapeutic agent for CML in 2001 (*Oncologist,* 6 (3), 233-238, 2001). It is currently used as a primary therapeutic agent for CML patients, and it has been shown to be effective in 67% of patients, but resistance within 6 months is often reported. The clinically observed drug resistance of imatinib is known to be caused by a point mutation of the BCR-ABL gene, and the mutation (T315I) of the threonine at position 315 to isoleucine and the mutation (T253H) of the tyrosine at position 253 to histidine are the most frequent. Among these, the T315I mutation in the gatekeeper region accounts for about 20% of the drug resistance of imatinib. In this mutation, the steric hindrance between isoleucine (I) at position 315 and imatinib reduces the binding force of imatinib and kinase more than 100 fold, thereby disabling inhibition of kinase activity.

In an attempt to overcome resistance to the drug imatinib, the second-generation drugs such as nilotinib and dasatinib were developed. However, as a result of identification of the 17 types of mutations found so far, the second-generation drugs showed no effect on some mutations including T315I. Ponatinib, developed by Ariad Pharmaceuticals, Inc., is a kinase inhibitor targeting T315I Bcr-Abl, which is approved as a therapeutic agent for CML when a T315I mutationexists, or treatment of imatinib is unsuitable and upon emergence of drug resistance to nilotinib or dasatinib, or in an accelerated phase or blast phase at which treatment withstand is impossible. However, in 20% of patients administered with ponatinib, side effects such as thrombosis or narrowing of blood vessel walls have been reported, and post-marketing investigations have reported serious side effects such as death from cardiac attack, aggravation of cardiovascular diseases and stroke. Accordingly, the FDA recommends that caution should be taken upon administration to patients with cardiovascular diseases or those who are at high risk of thrombus, while taking into consideration whether the benefits of treatment through ponatinib administration outweigh the potential risks.

It has recently been found that DDR (discoidin domain receptor), which is another target of imatinib, exists in human chronic leukemia cell line K562 cells (*Eur. J. Pharmacol.,* 599 (1-3), 44-53, 2008). In addition to imatinib, other CML inhibitors, namely nilotinib and dasatinib exhibit a comparable inhibitory activity against DDR1, which might be due to the structural homology between the ABL and DDR proteins. DDR is a transmembrane tyrosine kinase receptor activated by collagen, and is associated with various diseases such as fibrotic disease, atherosclerosis and cancer (*Mol. Cell.,* 1, 25-34, 1997). It has been found that DDR expression is increased in various cancer cells, and many attempts to treat cancer using DDR inhibitors have been attempted, but the underlying mechanism has not been completely elucidated. In particular, DDR1 and DDR2 have high structural similarity, so achieving isoform selectivity is required.

Second-generation anti-cancer drugs with improved inhibitory effect against cancer cells, reduced side effects and proved ability to overcome resistance thereto are being developed. However their ability to inhibit mutant species has been found to be insufficient, so further research on drug development thereof was devoted. Therefore, it is urgent to develop a novel next-generation anticancer agent that can prevent or treat side effects and overcome the emerged drug resistance.

In view of this background, and as a result of designing a novel drug chemotype and conducting continuous research thereon to develop a new next-generation anticancer agent, the present inventors developed an anti-cancer compound that exhibited excellent inhibitory activity against cancer cells without causing side effects, particularly as an ABL/DDR1 inhibitor. A compound selected from novel indazole-derived compounds is useful for preventing or treating cancer, a pharmaceutically acceptable salt thereof, a hydrate thereof and a stereoisomer thereof, and a method for preparing the compound, and a pharmaceutical composition for preventing, alleviating or treating cancer containing the compound as an active ingredient, thereby completing the present invention.

The above information disclosed in this Background section is provided only for better understanding of the Background of the invention and therefore it may contain information that does not form the prior art that is already known in this country to a person of ordinary skill in the art.

PRIOR ART DOCUMENT

Non-Patent Document (Non-Patent Document 1) *N. Engl. J. Med.,* 340(17), 1330-1340, 1999
(Non-Patent Document 2) *Oncologist,* 6(3), 233-238, 2001
(Non-Patent Document 3) *Eur. J. Pharmacol.,* 599(1-3), 44-53, 2008
(Non-Patent Document 4) *Mol. Cell.,* 1, 25-34, 1997

SUMMARY OF THE DISCLOSURE

The present invention has been made in an effort to solve the above-described problems associated with the prior art.

It is one object of the present invention to provide a compound selected from a novel indazole-derived compound having inhibitory activity against a protein kinase, a pharmaceutically acceptable salt thereof, a hydrate thereof and a stereoisomer thereof.

The present invention is also directed to providing a pharmaceutical composition for preventing, alleviating or treating cancer containing the novel indazole compound, a pharmaceutically acceptable salt thereof, a hydrate thereof and a stereoisomer thereof as an active ingredient.

The present invention is also directed to providing a method for preparing the novel indazole compound, a pharmaceutically acceptable salt thereof, a hydrate thereof and a stereoisomer thereof.

The objects of the present invention are not limited to those described above. The objects of the present invention will be clearly understood from the following description and can be implemented by the means defined in the claims and combinations thereof.

In one aspect, the present invention provides a compound selected from an indazole-derived compound represented by the following Formula 1, a pharmaceutically acceptable salt thereof, a hydrate thereof and a stereoisomer thereof:

[Formula 1]

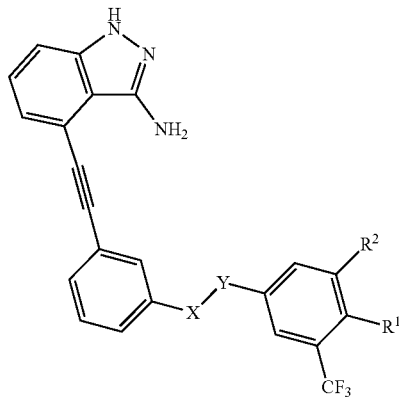

wherein $R^1$ and $R^2$ each independently represent hydrogen; a halogen atom; a $C_1$-$C_{13}$ alkyl group; a $C_3$-$C_{10}$ aryl group; a $C_3$-$C_{10}$ cyclic group; a $C_3$-$C_{10}$ heteroaryl group; and a $C_3$-$C_{10}$ heterocyclic group;

X and Y are each independently selected from the group consisting of —$NR_5$—; —$NR_5CH_2$—; —C(O)—; —C(O)$CH_2$—; —$CH_2$—; —S(O)$_2$—; —$NR_5$S(O)$_2$—; and —S(O)$_2NR_5$—; and $R_5$ is hydrogen; or a $C_1$-$C_6$ alkyl group;

wherein the $C_1$-$C_6$ alkyl group, the $C_1$-$C_{13}$ alkyl group or the $C_3$-$C_{10}$ cyclic group contains at least one substituent selected from the group consisting of hydrogen; a hydroxy group; a halogen group; a $C_1$-$C_{13}$ alkyl group; a $C_1$-$C_6$ alkoxy group; an amino group (—$NR_3R_4$); a nitro group (—$N(O)_2$); an amide group (—(C=O)$NR_3R_4$); a carboxyl group (—C(O)OH); a nitrile group (—CN); a urea group (—$NR_3$(C=O)$NR_4$—); a sulfonamide group (—NHS(O)$_2$—); a sulfide group (—S—); a sulfone group (—S(O)$_2$—); a phosphinyl group (—P(O)$R_3R_4$); a $C_6$-$C_{10}$ aryl group; a $C_3$-$C_{10}$ heteroaryl group; and a $C_3$-$C_{10}$ heterocyclic group, the $C_3$-$C_{10}$ aryl group, the $C_3$-$C_{10}$ heteroaryl group or the $C_3$-$C_{10}$ heterocyclic group contains at least one substituent selected from the group consisting of hydrogen; a hydroxy group; a halogen group; a carbonyl group (—(C=O)$R_3R_4$);

a $C_1$-$C_3$ alkyl group substituted or unsubstituted with halogen or a $C_3$-$C_{10}$ heterocyclic group; a $C_1$-$C_3$ alkoxy group substituted or unsubstituted with halogen or a $C_3$-$C_{10}$ heterocyclic group; $C_6$-$C_{10}$ phenoxy; an amino group (—$NR_3R_4$); a nitro group (—$N(O)_2$); an amide group (—(C=O)$NR_3R_4$); a carboxyl group (—C(O)OH); a nitrile group (—CN); a urea group (—$NR_3$(C=O)$NR_4$—); a sulfonamide group (—NHS(O)$_2$—); a sulfide group (—S—); a sulfone group (—S(O)$_2$—); a phosphinyl group (—P(O)$R_3R_4$); a $C_6$-$C_{10}$ aryl group; a $C_3$-$C_{10}$ heteroaryl group and a $C_3$-$C_{10}$ heterocyclic group, $R_3$ and $R_4$ described above each independently contain at least one selected from the group consisting of hydrogen; a $C_1$-$C_6$ alkyl group; a $C_1$-$C_6$ alkenyl group; a $C_1$-$C_6$ alkynyl group; a $C_6$-$C_{10}$ aryl group; a $C_3$-$C_{10}$ heteroaryl group; and a $C_3$-$C_{10}$ heterocyclic group, and the $C_3$-$C_{10}$ heteroaryl group and the $C_3$-$C_{10}$ heterocyclic group contain at least one heteroatom selected from the group consisting of N, O, and S.

In another aspect, the present invention provides a pharmaceutical composition for preventing, alleviating or treating cancer containing a compound selected from a group consisting of the indazole-derivative represented by Chemical Formula 1, a pharmaceutically acceptable salt thereof, a hydrate thereof and a stereoisomer thereof as an active ingredient.

In another aspect, the present invention provides a method for preparing a compound selected from a group consisting of the indazole derivative represented by Chemical Formula 1, a pharmaceutically acceptable salt thereof, a hydrate thereof and a stereoisomer thereof.

Other aspects and preferred embodiments of the invention are discussed below.

DETAILED DESCRIPTION

Unless otherwise stated in the context, all numbers, figures and/or expressions that represent ingredients, reaction conditions, polymer compositions and amounts of mixtures used in the specification are approximations that reflect various uncertainties of measurement occurring inherently in obtaining these figures, among other things. For this reason, it should be considered that, in all cases, the term "about" should be understood to modify all numbers, figures and/or expressions. In addition, when numerical ranges are disclosed in the description, these ranges are continuous and include all numbers from the minimum to the maximum including the maximum within each range unless otherwise defined. Furthermore, when the range refers to an integer, it includes all integers from the minimum to the maximum including the maximum within the range, unless otherwise defined.

It should be understood that, in the specification, when a range is referred to a parameter, the parameter encompasses all figures including end points disclosed within the range. For example, the range of "5 to 10" includes figures of 5, 6, 7, 8, 9, and 10, as well as arbitrary sub-ranges, such as ranges of 6 to 10, 7 to 10, 6 to 9, and 7 to 9, and any figures, such as 5.5, 6.5, 7.5, 5.5 to 8.5 and 6.5 to 9, between appropriate integers that fall within the range. In addition, for example, the range of "10% to 30%" encompasses all integers that include numbers such as 10%, 11%, 12% and 13% as well as 30%, and any sub-ranges, such as ranges of 10% to 15%, 12% to 18%, or 20% to 30%, as well as any numbers, such as 10.5%, 15.5% and 25.5%, between appropriate integers that fall within the range.

Hereinafter, the present invention will be described in detail.

As a result of continuous research to solve the above problems, the present inventors developed a compound selected from a group consisting of the indazole derivative represented by Chemical Formula 1 useful for the prevention or treatment of cancer as anti-cancer compounds exhibiting excellent inhibitory activity against cancer cells, improved kinase inhibitory activity against wild and mutant forms active, pharmaceutically acceptable salts thereof, hydrates thereof and stereoisomers thereof, a method for preparing the compound, and a pharmaceutical composition for preventing, alleviating or treating cancer containing the compound as an active ingredient.

In one aspect, the present invention provides a compound selected from a group consisting of the indazole derivative represented by Chemical Formula 1, a pharmaceutically acceptable salt thereof, a hydrate thereof and a stereoisomer thereof:

[Formula 1]

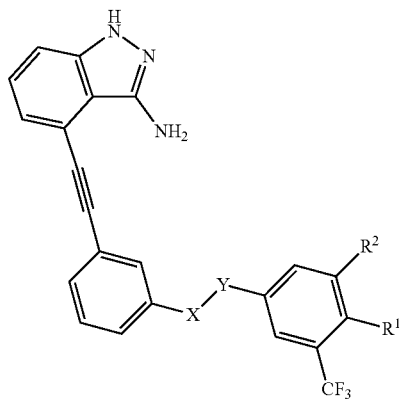

wherein $R^1$ and $R^2$ each independently represent hydrogen; a halogen atom; a $C_1$-$C_{13}$ alkyl group; a $C_3$-$C_{10}$ aryl group; a $C_3$-$C_{10}$ cyclic group; a $C_3$-$C_{10}$ heteroaryl group; and a $C_3$-$C_{10}$ heterocyclic group;

X and Y are each independently selected from the group consisting of —$NR_5$—; —$NR_5CH_2$—; —C(O)—; —C(O)$CH_2$—; —$CH_2$—; —$S(O)_2$—; —$NR_5S(O)_2$—; and —$S(O)_2NR_5$—; and $R_5$ is hydrogen; or a $C_1$-$C_6$ alkyl group;

wherein the $C_1$-$C_6$ alkyl group, the $C_1$-$C_{13}$ alkyl group or the $C_3$-$C_{10}$ cyclic group contains at least one substituent selected from the group consisting of hydrogen; a hydroxy group; a halogen group; a $C_1$-$C_{13}$ alkyl group; a $C_1$-$C_6$ alkoxy group; an amino group (—$NR_3R_4$); a nitro group (—$N(O)_2$); an amide group (—(C═O)$NR_3R_4$); a carboxyl group (—C(O)OH); a nitrile group (—CN); a urea group (—$NR_3$(C═O)$NR_4$—); a sulfonamide group (—$NHS(O)_2$—); a sulfide group (—S—); a sulfone group (—$S(O)_2$—); a phosphinyl group (—P(O)$R_3R_4$); a $C_6$-$C_{10}$ aryl group; a $C_3$-$C_{10}$ heteroaryl group; and a $C_3$-$C_{10}$ heterocyclic group, the $C_3$-$C_{10}$ aryl group, the $C_3$-$C_{10}$ heteroaryl group or the $C_3$-$C_{10}$ heterocyclic group contains at least one substituent selected from the group consisting of hydrogen; a hydroxy group; a halogen group; a carbonyl group (—(C═O)$R_3R_4$); a $C_1$-$C_3$ alkyl group substituted or unsubstituted with halogen or a $C_3$-$C_{10}$ heterocyclic group; a $C_1$-$C_3$ alkoxy group substituted or unsubstituted with halogen or a $C_3$-$C_{10}$ heterocyclic group; $C_6$-$C_{10}$ phenoxy; an amino group (—$NR_3R_4$); a nitro group (—$N(O)_2$); an amide group (—(C═O)$NR_3R_4$); a carboxyl group (—C(O)OH); a nitrile group (—CN); a urea group (—$NR_3$(C═O)$NR_4$—); a sulfonamide group (—$NHS(O)_2$—); a sulfide group (—S—); a sulfone group (—$S(O)_2$—); a phosphinyl group (—P(O)$R_3R_4$); a $C_6$-$C_{10}$ aryl group; a $C_3$-$C_{10}$ heteroaryl group and a $C_3$-$C_{10}$ heterocyclic group, $R_3$ and $R_4$ described above each independently contain at least one selected from the group consisting of hydrogen; a $C_1$-$C_6$ alkyl group; a $C_1$-$C_6$ alkenyl group; a $C_1$-$C_6$ alkynyl group; a $C_6$-$C_{10}$ aryl group; a $C_3$-$C_{10}$ heteroaryl group; and a $C_3$-$C_{10}$ heterocyclic group, and the $C_3$-$C_{10}$ heteroaryl group and the $C_3$-$C_{10}$ heterocyclic group contain at least one heteroatom selected from the group consisting of N, O, and S.

Furthermore, $R^1$ and $R^2$ each independently represent hydrogen; a halogen atom selected from F and Cl; a methyl group; a substituted methyl group; a trifluoromethyl group; a $C_3$-$C_6$ heterocyclic group containing at least one heteroatom selected from O and N; or a $C_3$-$C_6$ heteroaryl group containing at least one heteroatom selected from O and N, the substituted methyl group contains at least one substituent selected from the group consisting of a $C_6$-$C_{10}$ aryl group; a $C_3$-$C_{10}$ heteroaryl group; and a $C_3$-$C_{10}$ heterocyclic group, and the $C_3$-$C_6$ heterocyclic group or the $C_3$-$C_6$ heteroaryl group contains a substituent of hydrogen or a $C_1$-$C_3$ alkyl group.

In addition, X and Y are each independently —NH—; or —C(O)—, and when X is —NH—, Y may be —C(O)—, and when X is —C(O)—, Y may be —NH—.

In another aspect, the present invention provides a compound selected from a group consisting of the indazole derivative represented by Chemical Formula 1, which is selected from the group consisting of the following compound Nos. 1 to 16, a pharmaceutically acceptable salt thereof, a hydrate thereof and a stereoisomer thereof.

(Compound No. 1) N-(3-((3-Amino-1H-indazol-4-yl)ethynyl)phenyl)-3-(trifluoromethyl)benzamide;

(Compound No. 2) 4N-(3-((3-Amino-1H-indazol-4-yl)ethynyl)phenyl)-3,5-bis (trifluoromethyl)benzamide;

(Compound No. 3) N-(3-((3-Amino-1H-indazol-4-yl)ethynyl)phenyl)-3-(4-methyl-1H-imidazol-1-yl)-5-(trifluoromethyl)benzamide;

(Compound No. 4) N-(3-((3-Amino-1H-indazol-4-yl)ethynyl)phenyl)-3-fluoro-5-(trifluoromethyl)benzamide;

(Compound No. 5) N-(3-((3-Amino-1H-indazol-4-yl)ethynyl)phenyl)-3-morpholino-5-(trifluoromethyl)benzamide;

(Compound No. 6) N-(3-((3-Amino-1H-indazol-4-yl)ethynyl)phenyl)-4-methyl-3-(trifluoromethyl)benzam id e;

(Compound No. 7) N-(3-((3-Amino-1H-indazol-4-yl)ethynyl)phenyl)-4-(4-methylpiperazin-1-yl)-3-(trifluoromethyl)benzamide;

(Compound No. 8) N-(3-((3-Amino-1H-indazol-4-yl)ethynyl)phenyl)-3,5-bis (trifluoromethyl)benzamide;

(Compound No. 9) 3-((3-Amino-1H-indazol-4-yl)ethynyl)-N-(3-(trifluoromethyl)phenyl)benzamide;

(Compound No. 10) 3-((3-Amino-1H-indazol-4-yl)ethynyl)-N-(3,5-bis(trifluoromethyl)phenyl)benzamide;

(Compound No. 11) 3-((3-Amino-1H-indazol-4-yl)ethynyl)-N-(3-(4-methyl-1H-imidazol-1-yl)-5-(trifluoromethyl)phenyl)benzamide;

(Compound No. 12) 3-((3-Amino-1H-indazol-4-yl)ethynyl)-N-(3-((4-methylpiperazin-1-yl)methyl)-5-(trifluoromethyl)phenyl)benzamide;

(Compound No. 13) 3-((3-Amino-1H-indazol-4-yl)ethynyl)-N-(3-((4-methylpiperazin-1-yl)methyl)-5-(trifluoromethyl)phenyl)benzamide;

(Compound No. 14) 3-((3-Amino-1H-indazol-4-yl)ethynyl)-N-(4-chloro-3-(trifluoromethyl)phenyl)benzamide;

(Compound No. 15) 3-((3-Amino-1H-indazol-4-yl)ethynyl)-N-(4-((4-ethylpiperazin-1-yl)methyl)-3-(trifluoromethyl)phenyl)benzamide; and (Compound No. 16) 3-((3-Amino-1H-indazol-4-yl)ethynyl)-N-(4-(morpholinomethyl)-3-(trifluoromethyl)phenylbenzamide.

As used herein, the term "substitution" means that, when one or more hydrogen atoms in an organic compound are replaced with another atomic group to form a derivative, the other atomic group is introduced in place of a hydrogen atom, and the term "substituent" refers to an atomic group introduced at this time.

Examples of the substituent include halogen atoms, $C_1$-$C_{20}$ alkyl groups substituted with a halogen atom (e.g., $CCF_3$, $CHCF_2$, $CH_2F$ or $CCl_3$), $C_1$-$C_{20}$ alkoxy, $C_1$-$C_{20}$ alkoxyalkyl, a hydroxy group, a nitro group, a cyano group, an amino group, an amidino group, hydrazine, hydrazone, a carboxyl group or salt thereof, a sulfonyl group, a sulfamoyl group, a sulfonic acid group or salt thereof, a phosphoric acid or salt thereof, or a $C_1$-$C_{20}$ alkyl group, a $C_2$-$C_{20}$ alkenyl group, a $C_2$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, a $C_7$-$C_{20}$ heteroarylalkyl group, a $C_6$-$C_{20}$ heteroaryloxy group, and a $C_6$-$C_{20}$ heteroaryloxyalkyl group or a $C_6$-$C_{20}$ heteroarylalkyl group.

In the definition of substituents in the present invention, the term "alkyl" means an aliphatic hydrocarbon radical. The alkyl may be saturated alkyl that does not contain an alkenyl or alkynyl moiety, or unsaturated alkyl that contains at least one alkenyl or alkynyl moiety. The term "alkenyl" means a group containing at least one carbon-carbon double bond, and the term "alkynyl" means a group containing at least one carbon-carbon triple bond. The alkyl may have a cyclic, branched or straight-chain form when used alone or in combination.

The term "aryl" means an aromatic monocyclic group containing 6 carbon atoms which may be further fused singly or in combination with another radical with a second 5- or 6-membered carbocyclic group which may be aromatic, saturated or unsaturated. Examples of aryls may include, but are not limited to, phenyl, indanyl, 1-naphthyl, 2-naphthyl, tetrahydronaphthyl and the like. The aryl may be linked to another group at an appropriate position on the aromatic ring.

The term "alkoxy" refers to an alkyl group (i.e., —O-alkyl) linked to another group via an oxygen atom. The alkoxy group may be unsubstituted or substituted with at least one appropriate substituent. Examples of the alkoxy group include, but are not limited to, ($C_1$-$C_6$) alkoxy groups such as —O-methyl, —O-ethyl, —O-propyl, —O-isopropyl, —O-2-methyl-1-propyl, —O-2-methyl-2-propyl, —O-2-methyl-1-butyl, —O-3-methyl-1-butyl, —O-2-methyl-3-butyl, —O-2,2-dimethyl-1-propyl, —O-2-methyl-1-pentyl, -3-O-methyl-1-pentyl, —O-4-methyl-1-pentyl, —O-2-methyl-2-pentyl, —O-3-methyl-2-pentyl, —O-4-methyl-2-pentyl, —O-2,2-dimethyl-1-butyl, —O-3,3-dimethyl-butyl, —O-2-ethyl-1-butyl, —O-2-ethyl-1-butyl, —O-butyl, —O-isobutyl, —O-t-butyl, —O-pentyl, —O-isopentyl, —O-neopentyl and —O-hexyl.

The term "phenoxy" means a phenyl group (i.e., —O-aryl) linked to another group via an oxygen atom. The phenoxy group may be unsubstituted or substituted with at least one halogen; an alkyl group; an aryl group; and a heteroaryl group, but is not limited thereto.

The term "amino group" means an alkyl group linked to another group via a nitrogen atom (i.e., —NH— or —N-alkyl). The amino group may be unsubstituted or substituted with at least one appropriate substituent. Examples of the amine group include, but are not limited to, ($C_1$-$C_6$) amino groups, such as —NH-methyl, —NH-ethyl, —NH-propyl, —NH-isopropyl, —NH-2-methyl-1-propyl, —NH-2-methyl-2-propyl, —NH-2-methyl-1-butyl, —NH-3-methyl-1-butyl, —NH-2-methyl-3-butyl, —NH-2,2-dimethyl-1-propyl, —NH-2-methyl-1-pentyl, 3-NH-methyl-1-pentyl, —NH-4-methyl-1-pentyl, —NH-2-methyl-2-pentyl, —NH-3-methyl-2-pentyl, —NH-4-methyl-2-pentyl, —NH-2,2-dimethyl-1-butyl, —NH-3,3-dimethyl-butyl, —NH-2-ethyl-1-butyl, —NH-butyl, —NH-isobutyl, —NH-t-butyl, —NH-pentyl, —NH-isopentyl, —NH-neopentyl, —NH-hexyl, —N,N-dimethyl, —N-methyl-N-ethyl, —N-methyl-N-propyl, —N-methyl-isopropyl, —N-methyl-N-butyl, —N-methyl-N-isobutyl, —N-methyl-N-pentyl, —N-methyl-N-isopentyl, N-methyl-N-hexyl, N-methyl-N-isohexyl, —N,N-diethyl, —N-ethyl-N-propyl, —N-ethyl-N-isopropyl, —N-ethyl-N-butyl, —N-ethyl-N-isobutyl, —N-ethyl-N-pentyl, —N-ethyl-N-isopentyl, —N-ethyl-N-hexyl, —N-ethyl-N-isohexyl, —N,N-dipropyl, —N-propyl-N-isopropyl, —N-propyl-N-butyl, —N-propyl-N-isobutyl, —N-propyl-N-pentyl, —N-propyl-N-isopentyl, —N-propyl-N-hexyl, —N-propyl-N-isohexyl, —N,N-dibutyl, —N-butyl-N-isobutyl, —N-butyl-N-pentyl, —N-butyl-N-isopentyl, —N-butyl-N-hexyl, —N-butyl-N-isohexyl, —N,N-dipentyl, —N-pentyl-N-hexyl, —N-pentyl-N-isohexyl, and —N,N-dihexyl.

The term "halogen atom" refers to an atom in group 7 of the periodic table. The halogen atom includes fluorine (F), chlorine ($C_1$), bromine (Br) and iodine (I).

The term "carbonyl group" means —(C=O)—, and may be substituted with hydrogen, an alkyl group, an alkoxy group and an amino group, but is not limited thereto.

The term "heterocycle group" means a heteroaromatic compound containing at least one hetero atom selected from the group consisting of N, O, and S, unless otherwise mentioned. Preferably, the heterocyclic group may include a pyrrolidine group, a furan group, a morpholine group, a piperazine group and a piperidine group, and more preferably a pyrrolidine group, a piperidine group, a piperazine group and a morpholine group, but is not limited thereto.

The term "heteroaryl group" means a heteroaromatic compound containing at least one hetero atom selected from the group consisting of N, O, and S, unless otherwise mentioned. Preferably, the heteroaryl group is a pyridine group, a pyrazine group, a pyrimidine group, a pyridazine group, a pyrazole group, an imidazole group, a triazole group, an indole group, an oxadiazole group, a thiadiazole group, a quinoline group, an isoquinoline group, an isoxazole group, an oxazole group, a thiazolyl group and a pyrrole group, but is not limited thereto.

The term "derivative" refers to a compound obtained by substituting a part of the structure of the compound with another atom or atomic group.

The term "stereoisomer" refers to a compound that has an identical molecular formula and an identical method of linking constituent atoms, but has different spatial arrangement between atoms. A stereoisomer may be a diastereomer or an enantiomer. An enantiomer is an isomer that does not overlap a mirror structure thereof, like the relationship between the left and right hands, which is also called "an optical isomer". The enantiomer is divided into R (rectus: clockwise) and S (sinister: counterclockwise) when 4 or more substituents of the chiral center carbon are different. A diastereoisomer is a stereoisomer that does not a mirror relationship and may be divided into cis-trans isomers depending on the difference in the spatial arrangement of atoms.

Specific examples of indazole derived compounds preferred as compounds according to the present invention are as follows:

[Compound No. 1: N-(3-((3-Amino-1H-indazol-4-yl) ethynyl)phenyl)-3-(trifluoromethyl)benzamide;

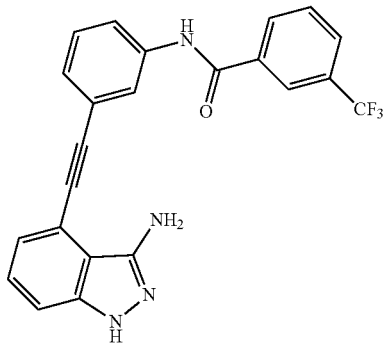 [SMILES: Nc1n[nH]c2cccc(C#Cc3cccc(NC(=O)c4cccc(C(F)(F)F)c4)c3)c12]

[Compound No. 2: 4N-(3-((3-Amino-1H-indazol-4-yl) ethynyl)phenyl)-3,5-bis (trifluoromethyl)benzamide];

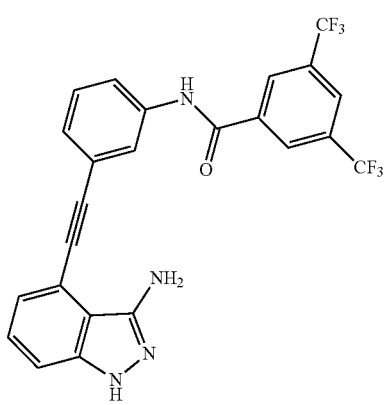 [SMILES: Nc1n[nH]c2cccc(C#Cc3cccc(NC(=O)c4cc(C(F)(F)F)cc(C(F)(F)F)c4)c3)c12]

[Compound No. 3: N-(3-(3-Amino-1H-indazol-4-yl)ethynyl)phenyl)-3-(4-methyl-1H-imidazol-1-yl)-5-(trifluoromethyl)benzamide];

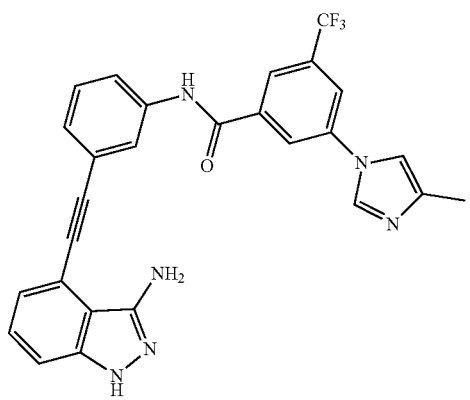 [SMILES: Cc1cn(-c2cc(C(=O)Nc3cccc(C#Cc4cccc5[nH]nc(N)c45)c3)cc(C(F)(F)F)c2)cn1]

[Compound No. 4: N-(3-((3-Amino-1H-indazol-4-yl) ethynyl)phenyl)-3-fluoro-5-(trifluoromethyl)benzamide];

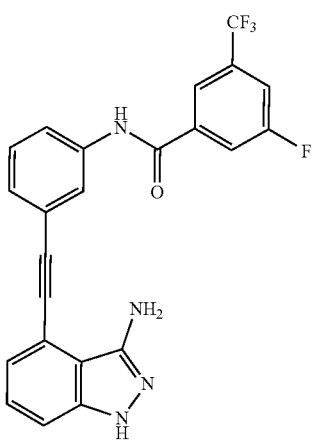 [SMILES: Nc1n[nH]c2cccc(C#Cc3cccc(NC(=O)c4cc(F)cc(C(F)(F)F)c4)c3)c12]

[Compound No. 5: N-(3-((3-Amino-1H-indazol-4-yl) ethynyl)phenyl)-3-morpholino-5-(trifluoromethyl)benzamide];

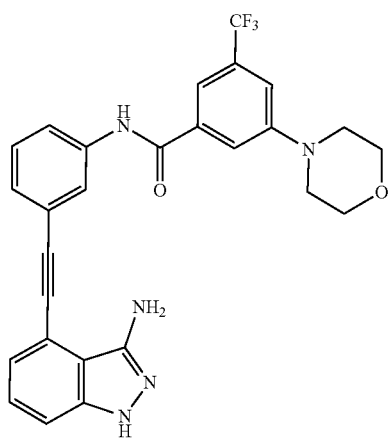 [SMILES: Nc1n[nH]c2cccc(C#Cc3cccc(NC(=O)c4cc(N5CCOCC5)cc(C(F)(F)F)c4)c3)c12]

[Compound No. 6: N-(3-((3-Amino-1H-indazol-4-yl) ethynyl)phenyl)-4-methyl-3-(trifluoromethyl)benzamide];

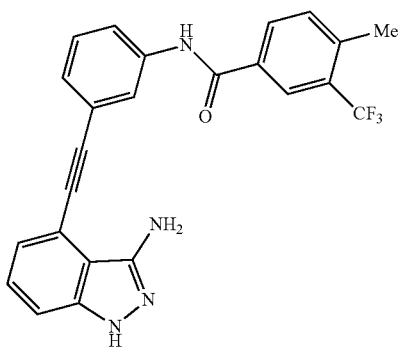 [SMILES: Cc1ccc(C(=O)Nc2cccc(C#Cc3cccc4[nH]nc(N)c34)c2)cc1C(F)(F)F]

[Compound No. 7: N-(3-((3-Amino-1H-indazol-4-yl)ethynyl)phenyl)-4-(4-methylpiperazin-1-yl)-3-(trifluoromethyl)benzamide];

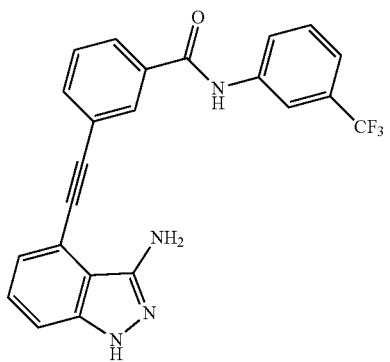

[Compound No. 10: 3-((3-Amino-1H-indazol-4-yl)ethynyl)-N-(3,5-bis(trifluoromethyl)phenyl)benzamide];

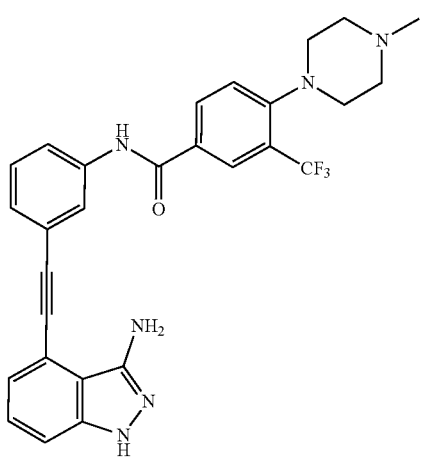 [SMILES: CN1CCN(c2ccc(C(=O)Nc3cccc(C#Cc4cccc5[nH]nc(N)c45)c3)cc2C(F)(F)F)CC1]

[Compound No. 8: N-(3-(3-Amino-1H-indazol-4-yl)ethynyl)phenyl)-3,5-bis (trifluoromethyl)benzamide];

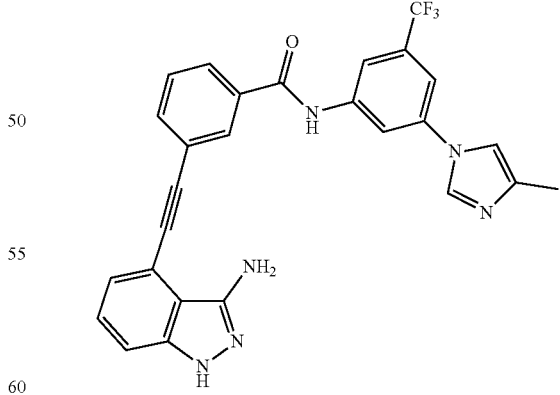

[Compound No. 11: 3-((3-Amino-1H-indazol-4-yl)ethynyl)-N-(3-(4-methyl-1H-imidazol-1-yl)-5-(trifluoromethyl)phenyl)benzamide];

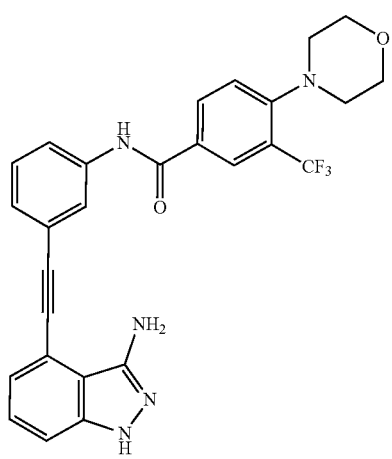 [SMILES: Nc1n[nH]c2cccc(C#Cc3cccc(NC(=O)c4ccc(N5CCOCC5)c(C(F)(F)F)c4)c3)c12]

[Compound No. 9: 3-(3-Amino-1H-indazol-4-yl)ethynyl)-N-(3-(trifluoromethyl)phenyl)benzamide];

[Compound No. 12: 3-((3-Amino-1H-indazol-4-yl)ethynyl)-N-(3-(4-methylpiperazin-1-yl)methyl)-5-(trifluoromethyl)phenyl)benzamide];

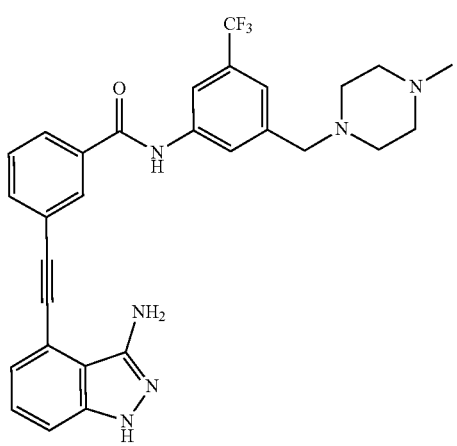 [SMILES: CN1CCN(Cc2cc(NC(=O)c3cccc(C#Cc4cccc5[nH]nc(N)c45)c3)cc(C(F)(F)F)c2)CC1]

[Compound No. 13: 3-((3-Amino-1H-indazol-4-yl)ethynyl)-N-(3-((4-methylpiperazin-1-yl)methyl)-5-(trifluoromethyl)phenyl)benzamide];

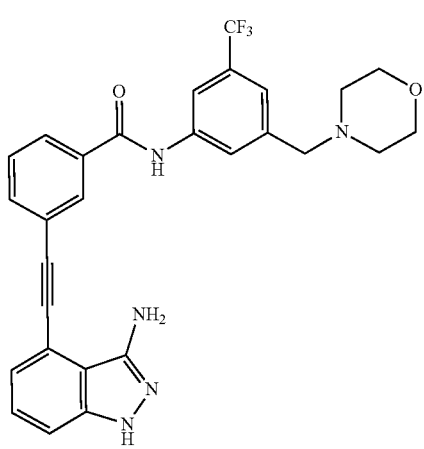 [SMILES: Nc1n[nH]c2cccc(C#Cc3cccc(C(=O)Nc4cc(CN5CCOCC5)cc(C(F)(F)F)c4)c3)c12]

[Compound No. 14: 3-((3-Amino-1H-indazol-4-yl)ethynyl)-N-(4-chloro-3-(trifluoromethyl)phenyl)benzamide];

[Compound No. 15: 3-((3-Amino-1H-indazol-4-yl)ethynyl)-N-(4-((4-ethylpiperazin-1-yl)methyl)-3-(trifluoromethyl)phenyl)benzamide];

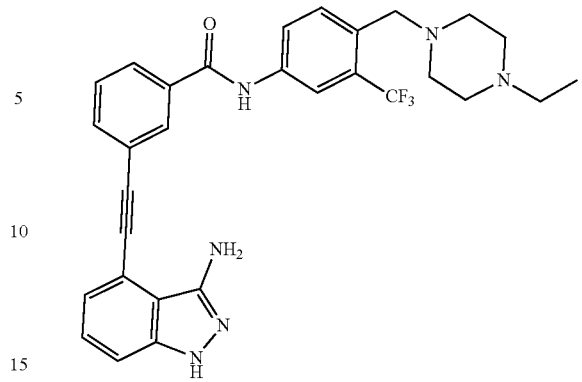

[Compound No. 16: 3-((3-Amino-1H-indazol-4-yl)ethynyl)-N-(4-(morpholinomethyl)-3-(trifluoromethyl)phenyl)benzamide];

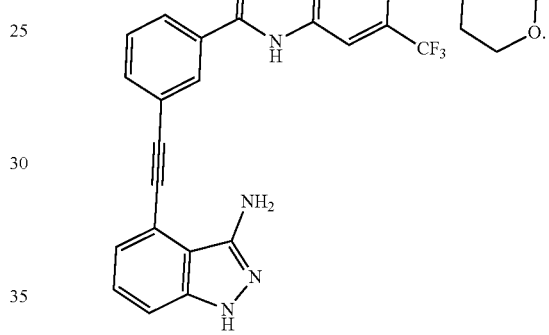

The compound of Formula 1 according to the present invention may be used in the form of a pharmaceutically acceptable salt derived from an inorganic or organic acid, and preferred pharmaceutically acceptable salts may include at least one selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

The compound of Formula 1 according to the present invention or a pharmaceutically acceptable salt thereof may include a hydrate and a solvate. The hydrate may be formed by bonding the compound of Formula 1 with a water molecule.

In another aspect, the present invention provides a pharmaceutical composition for preventing, alleviating or treating cancer containing, as an active ingredient, a compound selected from a group consisting of the indazole derivative represented by Chemical Formula 1 according to the present invention, a pharmaceutically acceptable salt thereof, a hydrate thereof and a stereoisomer thereof.

The pharmaceutical composition according to the present invention has excellent ability to inhibit the activity of protein kinase. The protein kinase may specifically include ABL, T315I mutant ABL or DDR1 or the similar.

Therefore, the pharmaceutical composition of the present invention may be used for treating, preventing and alleviating cancer caused by abnormal cell growth. The types of cancer that can be prevented, treated or alleviated through treatment with the pharmaceutical composition of the present invention include blood cancer, lung cancer, breast cancer, stomach cancer, liver cancer, colon cancer, skin cancer, uterine cancer, brain cancer, laryngeal cancer, prostate cancer, bladder cancer, esophageal cancer, thyroid cancer, kidney cancer and rectal cancer. Specifically, the blood cancer may be chronic myelogenous leukemia, acute myelogenous leukemia, chronic lymphocytic leukemia or acute lymphocytic leukemia.

In particular, the pharmaceutical composition of the present invention exhibits excellent inhibitory activity against ABL protein kinase and DDR1 protein kinase as well as T315I point mutation ABL protein kinase, and is thus useful as a therapeutic agent for preventing, alleviating or treating blood cancer, particularly chronic myelogenous leukemia (CML).

Preferably, the cancer is mediated and caused by protein kinase, and more preferably, the protein kinase may include at least one selected from ABL, ABL T315I and DDR1.

In another aspect, the present invention provides a pharmaceutical composition for preventing, alleviating or treating cancer, containing any one of the compounds as an active ingredient.

In another aspect, the present invention provides a pharmaceutical composition for preventing, alleviating or treating cancer, wherein the cancer includes at least one selected from the group consisting of blood cancer, lung cancer, breast cancer, stomach cancer, liver cancer, colon cancer, skin cancer, uterine cancer, brain cancer, laryngeal cancer, prostate cancer, bladder cancer, esophageal cancer, thyroid cancer, kidney cancer and rectal cancer.

In another aspect, the present invention provides a pharmaceutical composition for preventing, alleviating or treating cancer, wherein the cancer is chronic myelogenous leukemia (CML).

In one embodiment of the present invention, the result of verifying the activity inhibition effect of the novel indazole-derived compounds designed as ABL/DDR1 inhibitors against normal ABL and T315I point mutations ABL and DDR1 protein kinases showed that the novel indazole-derived compound has excellent selective inhibitory activity against ABL and DDR1 kinases and T315I point mutation kinases of ABL (Experimental Example 1).

In addition, the result of verifying the anti-cancer effect of the novel indazole derived compound on K562 cells, which are a chronic leukemia (CML) cell line, showed that the novel indazole derived compound has an excellent effect of inhibiting the proliferation of K562 cells (Experimental Example 2).

As described above, it was proved that the novel indazole derived compound according to the present invention is a selective inhibitor of wild and mutant ABL kinase, and has a selective high inhibitory activity and anti-proliferative effect on chronic leukemia cells, and thus is useful as a composition for treating chronic myelogenous leukemia.

In another aspect, the present invention provides a pharmaceutical composition for preventing, alleviating or treating cancer, wherein the pharmaceutical composition is administered to a patient having at least one of an ABL gene, a T315I mutant ABL gene and a DDR1 gene.

The pharmaceutical composition may be applied, without being limited thereto, to experimental animals such as mice, rabbits, rats, guinea pigs or hamsters, preferably primates including humans, more preferably humans.

As used herein, the term "treatment" includes alleviating or ameliorating symptoms, reducing the extent of a disease, delaying or alleviating disease progression, ameliorating, alleviating or stabilizing a disease, partial or full recovery, prolonging survival, and other beneficial treatment results.

In addition, as used herein, the treatment of cancer means treatment of all cancer cells, and the cancer includes angiogenesis of endothelial cells and mitosis thereof (solid tumor, tumor metastasis and benign tumor). For example, the cancer includes, but is not limited to, breast cancer, ovarian cancer, cervical cancer, prostate cancer, testicular cancer, genitourinary cancer, esophageal cancer, laryngeal cancer, glioblastoma, stomach cancer, skin cancer, keratoacanthomas, lung cancer, squamous cell carcinoma, large cell carcinoma, small cell carcinoma, lung adenocarcinoma, bone cancer, colon cancer, adenoma, pancreatic cancer, adenocarcinoma, carcinogenic cancer, follicular carcinoma, undifferentiated cancer, papillary cancer, normal hematoma, melanoma, sarcoma, bladder cancer, liver cancer and bile duct cancer, kidney cancer, myeloid disease, lymphoid disease, Hodgkin's disease, hair cell cancer, oral cavity cancer, pharyngeal (oral) cancer, lip cancer, tongue cancer, small intestine cancer, colorectal cancer, rectal cancer, brain cancer, central nervous system cancer, leukemia, hemangioma, trachoma or purulent sarcoma.

The content of the active ingredient, namely, the compound represented by Formula 1 above, the pharmaceutically acceptable salt thereof, the hydrate thereof and the stereoisomer thereof is appropriately adjusted by a selection by those skilled in the art according to the mode and method of utilization of the pharmaceutical composition of the present invention.

For example, the pharmaceutical composition is present in an amount of 0.1 to 10% by weight, more preferably 0.5 to 5% by weight, based on the total weight of the compound selected from the indazole derivative represented by Formula 1, the pharmaceutically acceptable salt thereof, the hydrate thereof and the stereoisomer thereof.

The compound selected from the indazole derivative represented by Formula 1, the pharmaceutically acceptable salt thereof, the hydrate thereof and the stereoisomer thereof may be present in the pharmaceutical composition alone or in combination with a pharmacologically acceptable carrier, excipient, diluent or sub-component.

Examples of pharmaceutically acceptable carriers, excipients and diluents include, but are not limited thereto, one or more selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil, dextrin, calcium carbonate, propylene glycol, liquid paraffin and physiological saline, and a common carrier, excipient, or diluent may be used. In addition, the pharmaceutical composition may further include a conventional filler, extender, binder, disintegrating agent, anticoagulant, lubricant, wetting agent, pH adjusting agent, nutrient, vitamin, electrolyte, alginic acid and salt thereof, pectic acid and salt thereof, protective colloid, glycerin, fragrance, emulsifier, preservative or the like.

The compound selected from the indazole derived compound represented by Formula 1, the pharmaceutically acceptable salt thereof, the hydrate thereof and the stereoisomer thereof can improve an effect of treatment with the anticancer drug when administered in combination with another anticancer drug for treating cancer or tumors.

Specifically, the pharmaceutical composition may further contain at least one another anti-cancer agent or therapeutic agent known to be effective for treating or preventing cancer in addition to the active ingredient and thus may be used as a simultaneously or separately applied combination therapy. Other anti-cancer agents or therapeutic agents that may be applied to the combination therapy may include, for example, at least one compound selected from the group consisting of Gleevec® (imatinib), Sutent® (sunitinib), Herceptin® (trastuzumab), Velcade® (bortezomib), dexamethasone, Nexavar® (sorafenib), aromatase inhibitors, or kinase inhibitors, but are not limited thereto.

The pharmaceutical composition may be administered orally or parenterally, and for example, may be administered through various routes including oral, transdermal, subcutaneous, intravenous or intramuscular routes. In addition, the formulation of the composition may vary depending on the method of use and may be formulated using methods well known in the art to provide rapid, sustained or delayed release of the active ingredient after administration to a mammal. In general, solid preparations for oral administration include tablets, troche, soft or hard capsules, pills, powders, granules and the like. These preparations, for example, can be prepared by mixing starch, calcium carbonate, sucrose, lactose, gelatin or the like. In addition, lubricants such as magnesium stearate and talc may be also used in addition to simple excipients. Liquid preparations for oral administration include suspensions, liquids and solutions, emulsions, syrups and the like. In addition to water and liquid paraffin, which are common simple diluents, various excipients such as wetting agents, sweeteners, fragrances and preservatives may be included. Formulations for parenteral administration include creams, lotions, ointments, plasters, liquids and solutions, aerosols, fluid extracts, elixir, infusions, sachet, patch, injections and the like. Injection formulations may be preferably in the form of an isotonic aqueous solution or suspension.

The pharmaceutical composition may further contain an adjuvant such as a sterilant, a preservative, a stabilizer, a hydrating agent or an emulsifying accelerator, a salt and/or a buffer for controlling osmotic pressure, and other therapeutically useful substances. Alternatively, the pharmaceutical composition may be formulated according to an ordinary mixing, granulation or coating method or using a suitable method known in the art.

In addition, the dosage of the pharmaceutical composition may be determined in consideration of the administration method, age, gender, disease severity, and conditions of the patient, the rate of absorption of the active ingredient in the body, the inactivation rate of the active ingredient and drugs used in combination therewith, and the pharmaceutical composition may be administered once or multiple times in a portionwise manner. The active ingredient of the pharmaceutical composition is preferably orally or parenterally administered to a mammal including a human in an amount of 0.001 to 100 mg/kg body weight, preferably 0.01 to 35 mg/kg body weight, on a daily basis, once or multiple times in a portionwise manner a day.

In another aspect, the present invention provides a method of treating cancer comprising administering a therapeutically effective amount of the compound selected from the indazole derivative represented by Formula 1, the pharmaceutically acceptable salt thereof, the hydrate thereof and the stereoisomer thereof.

Preferably, the treatment method may further include identifying a patient in need of prevention or treatment of cancer before the administration.

As used herein, the term "therapeutically effective amount" means an amount of an active ingredient which is effective for the prevention or treatment of cancer in a mammal, and the therapeutically effective amount may be controlled by a variety of factors such as the type of disease, the severity of the disease, the type and content of the active ingredient and other ingredients contained in the composition, the type of formulation, the age, weight, general health conditions, gender and diet of the patient, time of administration, route of administration, clearance rate of the composition in blood, duration of treatment, and drugs used simultaneously therewith. However, preferably, as described above, the compound may be administered in an amount of 0.001 to 100 mg/kg body weight, preferably 0.01 to 35 mg/kg body weight, on a daily basis, once or multiple times in a portionwise manner a day by oral or parenteral routes.

In another aspect, the present invention provides a method of preparing a compound selected from an indazole derivative represented by the following Formula 1, a pharmaceutically acceptable salt thereof, a hydrate thereof and a stereoisomer thereof, the method including reacting a compound represented by the following Formula 2 with a compound represented by the following Formula 3:

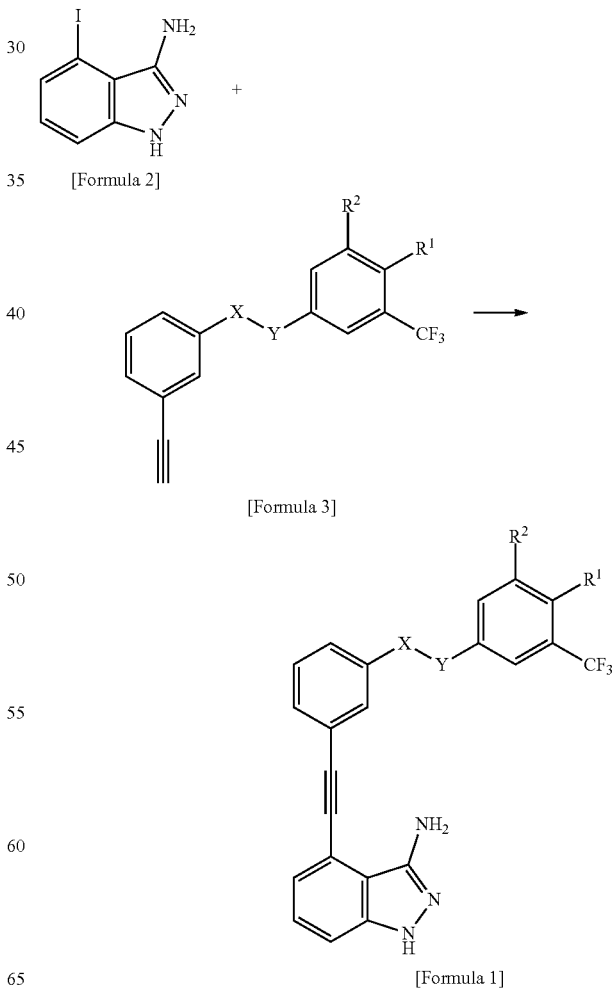

wherein R¹ and R² each independently represent hydrogen; a halogen atom; a $C_1$-$C_{13}$ alkyl group; a $C_3$-$C_{10}$ aryl group; a $C_3$-$C_{10}$ cyclic group; a $C_3$-$C_{10}$ heteroaryl group; and a $C_3$-$C_{10}$ heterocyclic group;

X and Y are each independently selected from the group consisting of —$NR_5$—; —$NR_5CH_2$—; —C(O)—; —C(O)$CH_2$—; —$CH_2$—; —S(O)$_2$—; —$NR_5$S(O)$_2$—; and —S(O)$_2$$NR_5$—; and $R_5$ is hydrogen; or a $C_1$-$C_6$ alkyl group;

wherein the $C_1$-$C_6$ alkyl group, the $C_1$-$C_{13}$ alkyl group or the $C_3$-$C_{10}$ cyclic group contains at least one substituent selected from the group consisting of hydrogen; a hydroxy group; a halogen group; a $C_1$-$C_{13}$ alkyl group; a $C_1$-$C_6$ alkoxy group; an amino group (—$NR_3R_4$); a nitro group (—N(O)$_2$); an amide group (—(C=O)$NR_3R_4$); a carboxyl group (—C(O)OH); a nitrile group (—CN); a urea group (—$NR_3$(C=O)$NR_4$—); a sulfonamide group (—NHS(O)$_2$—); a sulfide group (—S—); a sulfone group (—S(O)$_2$—); a phosphinyl group (—P(O)$R_3R_4$); a $C_6$-$C_{10}$ aryl group; a $C_3$-$C_{10}$ heteroaryl group; and a $C_3$-$C_{10}$ heterocyclic group, the $C_3$-$C_{10}$ aryl group, the $C_3$-$C_{10}$ heteroaryl group or the $C_3$-$C_{10}$ heterocyclic group contains at least one substituent selected from the group consisting of hydrogen; a hydroxy group; a halogen group; a carbonyl group (—(C=O)$R_3R_4$); a $C_1$-$C_3$ alkyl group substituted or unsubstituted with halogen or a $C_3$-$C_{10}$ heterocyclic group; a $C_1$-$C_3$ alkoxy group substituted or unsubstituted with halogen or a $C_3$-$C_{10}$ heterocyclic group; $C_6$-$C_{10}$ phenoxy; an amino group (—$NR_3R_4$); a nitro group (—N(O)$_2$); an amide group (—(C=O)$NR_3R_4$); a carboxyl group (—C(O)OH); a nitrile group (—CN); a urea group (—$NR_3$(C=O)$NR_4$—); a sulfonamide group (—NHS(O)$_2$—); a sulfide group (—S—); a sulfone group (—S(O)$_2$—); a phosphinyl group (—P(O)$R_3R_4$); a $C_6$-$C_{10}$ aryl group; a $C_3$-$C_{10}$ heteroaryl group and a $C_3$-$C_{10}$ heterocyclic group, $R_3$ and $R_4$ described above each independently contain at least one selected from the group consisting of hydrogen; a $C_1$-$C_6$ alkyl group; a $C_1$-$C_6$ alkenyl group; a $C_1$-$C_6$ alkynyl group; a $C_6$-$C_{10}$ aryl group; a $C_3$-$C_{10}$ heteroaryl group; and a $C_3$-$C_{10}$ heterocyclic group, and the $C_3$-$C_{10}$ heteroaryl group and the $C_3$-$C_{10}$ heterocyclic group contain at least one heteroatom selected from the group consisting of N, O, and S.

Hereinafter, a specific example of a method for preparing the indazole derived compound represented by Formula 1 above is described.

Preparation Method 1: Preparation of Indazole Derived Compound of Formula 1

As exemplified below, the method of preparing a compound selected from an indazole derivative represented by the following Formula 1, a pharmaceutically acceptable salt thereof, a hydrate thereof and a stereoisomer thereof may include reacting a compound represented by the following Formula 2 with a compound represented by the following Formula 3:

[Formula 1]

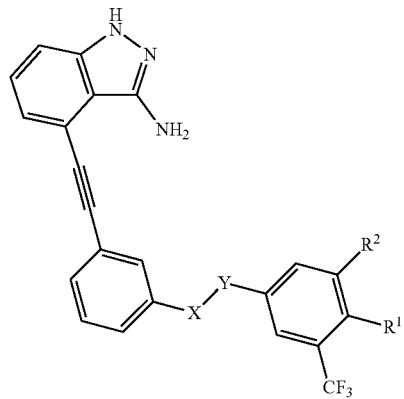

[Formula 2]

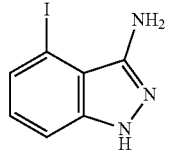

[Formula 3]

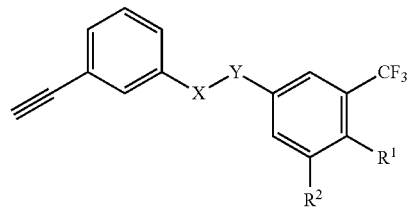

wherein R¹ and R² each independently represent hydrogen; a halogen atom; a $C_1$-$C_{13}$ alkyl group; a $C_3$-$C_{10}$ aryl group; a $C_3$-$C_{10}$ cyclic group; a $C_3$-$C_{10}$ heteroaryl group; and a $C_3$-$C_{10}$ heterocyclic group;

X and Y are each independently selected from the group consisting of —$NR_5$—; —$NR_5CH_2$—; —C(O)—; —C(O)$CH_2$—; —$CH_2$—; —S(O)$_2$—; —$NR_5$S(O)$_2$—; and —S(O)$_2$$NR_5$—; and $R_5$ is hydrogen; or a $C_1$-$C_6$ alkyl group;

wherein the $C_1$-$C_6$ alkyl group, the $C_1$-$C_{13}$ alkyl group or the $C_3$-$C_{10}$ cyclic group contains at least one substituent selected from the group consisting of hydrogen; a hydroxy group; a halogen group; a $C_1$-$C_{13}$ alkyl group; a $C_1$-$C_6$ alkoxy group; an amino group (—$NR_3R_4$); a nitro group (—N(O)$_2$); an amide group (—(C=O)$NR_3R_4$); a carboxyl group (—C(O)OH); a nitrile group (—CN); a urea group (—$NR_3$(C=O)$NR_4$—); a sulfonamide group (—NHS(O)$_2$—); a sulfide group (—S—); a sulfone group (—S(O)$_2$—); a phosphinyl group (—P(O)$R_3R_4$); a $C_6$-$C_{10}$ aryl group; a $C_3$-$C_{10}$ heteroaryl group; and a $C_3$-$C_{10}$ heterocyclic group, the $C_3$-$C_{10}$ aryl group, the $C_3$-$C_{10}$ heteroaryl group or the $C_3$-$C_{10}$ heterocyclic group contains at least one substituent selected from the group consisting of hydrogen; a hydroxy group; a halogen group; a carbonyl group (—(C=O)$R_3R_4$); a $C_1$-$C_3$ alkyl group substituted or unsubstituted with halogen or a $C_3$-$C_{10}$ heterocyclic group; a $C_1$-$C_3$ alkoxy group substituted or unsubstituted with halogen or a $C_3$-$C_{10}$ heterocyclic group; $C_6$-$C_{10}$ phenoxy; an amino group (—$NR_3R_4$); a nitro group (—N(O)$_2$); an amide group (—(C=O)$NR_3R_4$); a carboxyl group (—C(O)OH); a nitrile group (—CN); a urea group (—$NR_3$(C=O)$NR_4$—); a sulfonamide group (—NHS(O)$_2$—); a sulfide group (—S—); a sulfone group (—S(O)$_2$—); a phosphinyl group (—P(O)R$_3$R$_4$); a C$_6$-C$_{10}$ aryl group; a C$_3$-C$_{10}$ heteroaryl group and a C$_3$-C$_{10}$ heterocyclic group, R$_3$ and R$_4$ described above each independently contain at least one selected from the group consisting of hydrogen; a C$_1$-C$_6$ alkyl group; a C$_1$-C$_6$ alkenyl group; a C$_1$-C$_6$ alkynyl group; a C$_6$-C$_{10}$ aryl group; a C$_3$-C$_{10}$ heteroaryl group; and a C$_3$-C$_{10}$ heterocyclic group, and the C$_3$-C$_{10}$ heteroaryl group and the C$_3$-C$_{10}$ heterocyclic group contain at least one heteroatom selected from the group consisting of N, O, and S.

The step of reacting the compound of Formula 2 with the compound of Formula 3 may be performed by a method depicted in the following Reaction Scheme 1.

[Reaction Scheme 1]

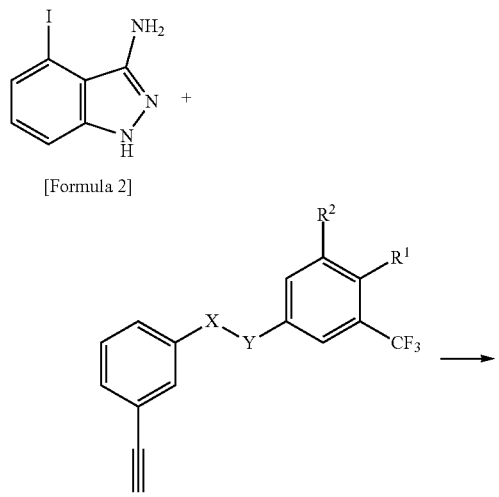

[Formula 2]

[Formula 3]

[Formula 1]

wherein R$^1$ and R$^2$ each independently represent hydrogen; a halogen atom; a C$_1$-C$_{13}$ alkyl group; a C$_3$-C$_{10}$ aryl group; a C$_3$-C$_{10}$ cyclic group; a C$_3$-C$_{10}$ heteroaryl group; and a C$_3$-C$_{10}$ heterocyclic group;

X and Y are each independently selected from the group consisting of —NR$_5$—; —NR$_5$CH$_2$—; —C(O)—; —C(O)CH$_2$—; —CH$_2$—; —S(O)$_2$—; —NR$_5$S(O)$_2$—; and —S(O)$_2$NR$_5$—; and R$_5$ is hydrogen; or a C$_1$-C$_6$ alkyl group;

wherein the C$_1$-C$_6$ alkyl group, the C$_1$-C$_{13}$ alkyl group or the C$_3$-C$_{10}$ cyclic group contains at least one substituent selected from the group consisting of hydrogen; a hydroxy group; a halogen group; a C$_1$-C$_{13}$ alkyl group; a C$_1$-C$_6$ alkoxy group; an amino group (—NR$_3$R$_4$); a nitro group (—N(O)$_2$); an amide group (—(C═O)NR$_3$R$_4$); a carboxyl group (—C(O)OH); a nitrile group (—CN); a urea group (—NR$_3$(C═O)NR$_4$—); a sulfonamide group (—NHS(O)$_2$—); a sulfide group (—S—); a sulfone group (—S(O)$_2$—); a phosphinyl group (—P(O)R$_3$R$_4$); a C$_6$-C$_{10}$ aryl group; a C$_3$-C$_{10}$ heteroaryl group; and a C$_3$-C$_{10}$ heterocyclic group, the C$_3$-C$_{10}$ aryl group, the C$_3$-C$_{10}$ heteroaryl group or the C$_3$-C$_{10}$ heterocyclic group contains at least one substituent selected from the group consisting of hydrogen; a hydroxy group; a halogen group; a carbonyl group (—(C═O)R$_3$R$_4$); a C$_1$-C$_3$ alkyl group substituted or unsubstituted with halogen or a C$_3$-C$_{10}$ heterocyclic group; a C$_1$-C$_3$ alkoxy group substituted or unsubstituted with halogen or a C$_3$-C$_{10}$ heterocyclic group; C$_6$-C$_{10}$ phenoxy; an amino group (—NR$_3$R$_4$); a nitro group (—N(O)$_2$); an amide group (—(C═O)NR$_3$R$_4$); a carboxyl group (—C(O)OH); a nitrile group (—CN); a urea group (—NR$_3$(C═O)NR$_4$—); a sulfonamide group (—NHS(O)$_2$—); a sulfide group (—S—); a sulfone group (—S(O)$_2$—); a phosphinyl group (—P(O)R$_3$R$_4$); a C$_6$-C$_{10}$ aryl group; a C$_3$-C$_{10}$ heteroaryl group and a C$_3$-C$_{10}$ heterocyclic group, R$_3$ and R$_4$ described above each independently contain at least one selected from the group consisting of hydrogen; a C$_1$-C$_6$ alkyl group; a C$_1$-C$_6$ alkenyl group; a C$_1$-C$_6$ alkynyl group; a C$_6$-C$_{10}$ aryl group; a C$_3$-C$_{10}$ heteroaryl group; and a C$_3$-C$_{10}$ heterocyclic group, and the C$_3$-C$_{10}$ heteroaryl group and the C$_3$-C$_{10}$ heterocyclic group contain at least one heteroatom selected from the group consisting of N, O, and S.

The preparation method of Reaction Scheme 1 may be performed by a carbon-carbon bond formation reaction (Sonogashira coupling) between the iodine group of Formula 2 and the alkynyl carbon of Formula 3.

The compound of Formula 2 may be performed by the method depicted in the following Reaction Scheme 2:

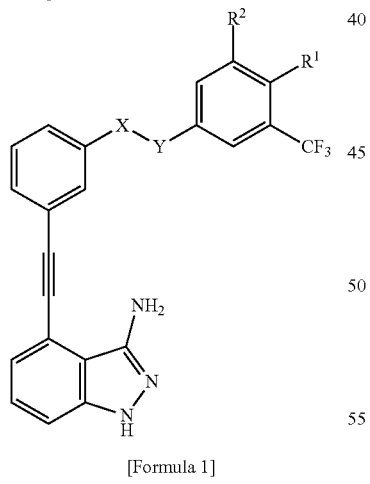

[Reaction Scheme 2]

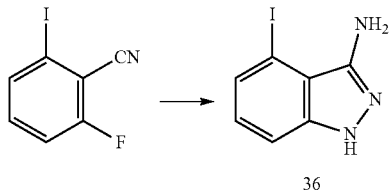

36

The compound of Formula 3 may be performed by the method depicted in the following Reaction Scheme 3 or Reaction Scheme 4.

[Reaction Scheme 3]

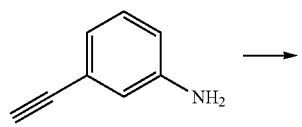

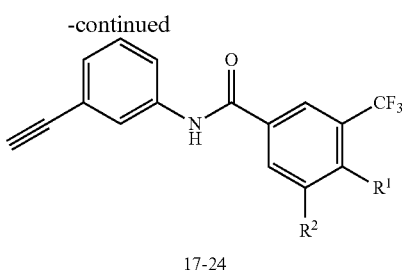

17-24

[Reaction Scheme 4]

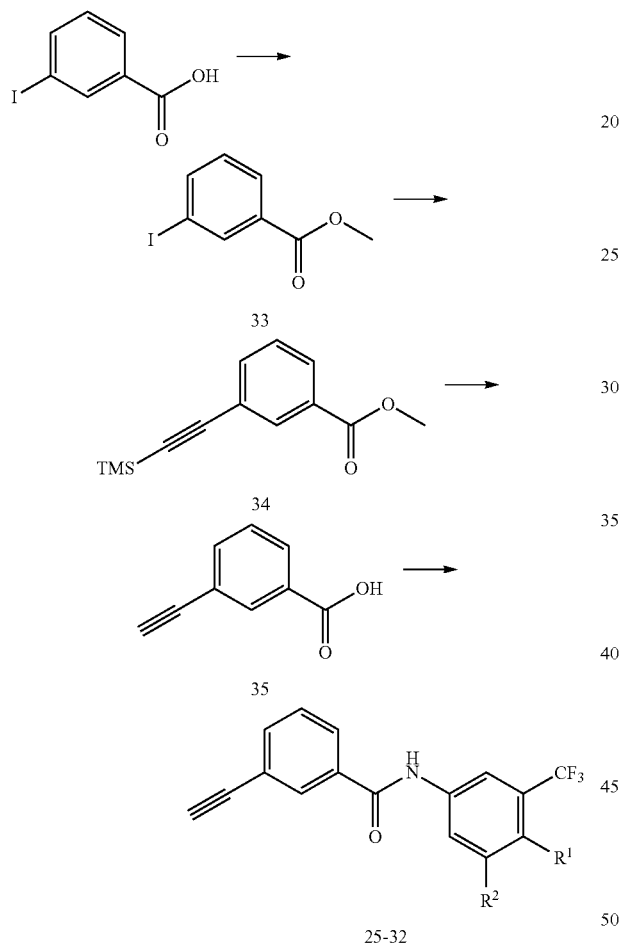

wherein $R^1$ and $R^2$ each independently represent hydrogen; a halogen atom; a $C_1$-$C_{13}$ alkyl group; a $C_3$-$C_{10}$ aryl group; a $C_3$-$C_{10}$ cyclic group; a $C_3$-$C_{10}$ heteroaryl group; and a $C_3$-$C_{10}$ heterocyclic group;

wherein the $C_1$-$C_{13}$ alkyl group or the $C_3$-$C_{10}$ cyclic group contains at least one substituent selected from the group consisting of hydrogen; a hydroxy group; a halogen group; a $C_1$-$C_{13}$ alkyl group; a $C_1$-$C_6$ alkoxy group; an amino group (—$NR_3R_4$); a nitro group (—$N(O)_2$); an amide group (—(C═O)$NR_3R_4$); a carboxyl group (—C(O)OH); a nitrile group (—CN); a urea group (—$NR_3$(C═O)$NR_4$—); a sulfonamide group (—$NHS(O)_2$—); a sulfide group (—S—); a sulfone group (—$S(O)_2$—); a phosphinyl group (—P(O)$R_3R_4$); a $C_6$-$C_{10}$ aryl group; a $C_3$-$C_{10}$ heteroaryl group; and a $C_3$-$C_{10}$ heterocyclic group, the $C_3$-$C_{10}$ aryl group, the $C_3$-$C_{10}$ heteroaryl group or the $C_3$-$C_{10}$ heterocyclic group contains at least one substituent selected from the group consisting of hydrogen; a hydroxy group; a halogen group; a carbonyl group (—(C═O)$R_3R_4$); a $C_1$-$C_3$ alkyl group substituted or unsubstituted with halogen or a $C_3$-$C_{10}$ heterocyclic group; a $C_1$-$C_3$ alkoxy group substituted or unsubstituted with halogen or a $C_3$-$C_{10}$ heterocyclic group; $C_6$-$C_{10}$ phenoxy; an amino group (—$NR_3R_4$); a nitro group (—$N(O)_2$); an amide group (—(C═O)$NR_3R_4$); a carboxyl group (—C(O)OH); a nitrile group (—CN); a urea group (—$NR_3$(C═O)$NR_4$—); a sulfonamide group (—$NHS(O)_2$—); a sulfide group (—S—); a sulfone group (—$S(O)_2$—); a phosphinyl group (—P(O)$R_3R_4$); a $C_6$-$C_{10}$ aryl group; a $C_3$-$C_{10}$ heteroaryl group and a $C_3$-$C_{10}$ heterocyclic group, $R_3$ and $R_4$ described above each independently contain at least one selected from the group consisting of hydrogen; a $C_1$-$C_6$ alkyl group; a $C_1$-$C_6$ alkenyl group; a $C_1$-$C_6$ alkynyl group; a $C_6$-$C_{10}$ aryl group; a $C_3$-$C_{10}$ heteroaryl group; and a $C_3$-$C_{10}$ heterocyclic group, and the $C_3$-$C_{10}$ heteroaryl group and the $C_3$-$C_{10}$ heterocyclic group contain at least one heteroatom selected from the group consisting of N, O, and S.

Specific examples of the compound of Formula 3 for preparing an indazole derived compound preferred as the compound according to the present invention are as follows:

[Compound No. 17: N-(3-Ethynylphenyl)-3-(trifluoromethyl)benzamide];

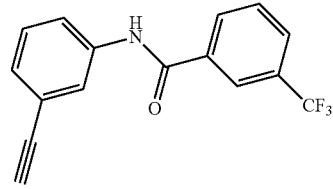 [SMILES: C#Cc1cccc(NC(=O)c2cccc(C(F)(F)F)c2)c1]

[Compound No. 18: N-(3-Ethynylphenyl)-3,5-bis(trifluoromethyl)benzamide];

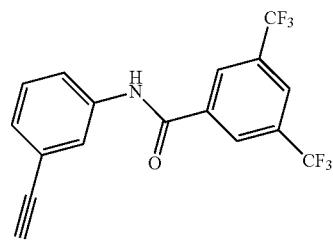 [SMILES: C#Cc1cccc(NC(=O)c2cc(C(F)(F)F)cc(C(F)(F)F)c2)c1]

[Compound No. 19: N-(3-Ethynylphenyl)-3-(4-methyl-1H-imidazol-1-yl)-5-(trifluoromethyl)benzamide];

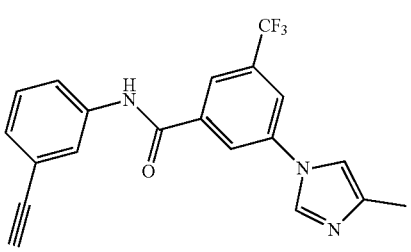 [SMILES: C#Cc1cccc(NC(=O)c2cc(-n3cnc(C)c3)cc(C(F)(F)F)c2)c1]

[Compound No. 20: N-(3-Ethynylphenyl)-3-fluoro-5-(trifluoromethyl)benzamide];

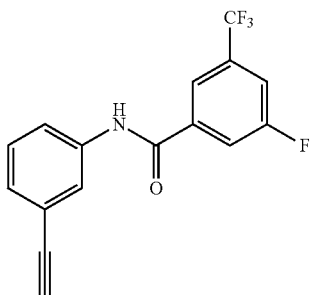 [SMILES: C#Cc1cccc(NC(=O)c2cc(F)cc(C(F)(F)F)c2)c1]

[Compound No. 21: N-(3-Ethynylphenyl)-3-morpholino-5-(trifluoromethyl)benzamide];

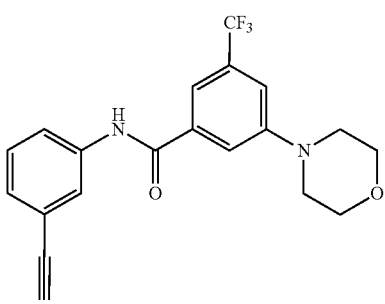 [SMILES: C#Cc1cccc(NC(=O)c2cc(N3CCOCC3)cc(C(F)(F)F)c2)c1]

[Compound No. 22: N-(3-Ethynylphenyl)-4-methyl-3-(trifluoromethyl)benzamide];

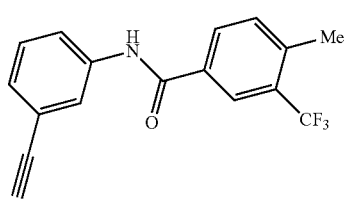 [SMILES: C#Cc1cccc(NC(=O)c2ccc(C)c(C(F)(F)F)c2)c1]

[Compound No. 23: N-(3-Ethynylphenyl)-4-(4-methylpiperazin-1-yl)-3-(trifluoromethyl)benzamide];

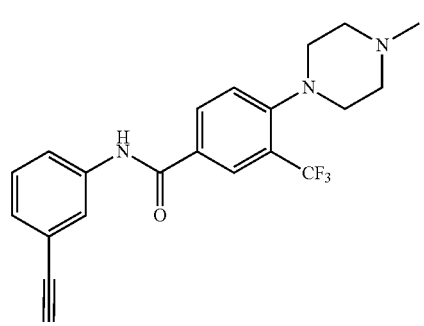 [SMILES: C#Cc1cccc(NC(=O)c2ccc(N3CCN(C)CC3)c(C(F)(F)F)c2)c1]

[Compound No. 24: N-(3-Ethynylphenyl)-4-morpholino-3-(trifluoromethyl)benzamide];

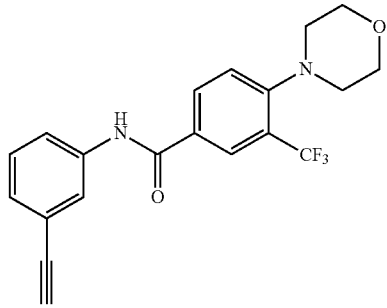 [SMILES: C#Cc1cccc(NC(=O)c2ccc(N3CCOCC3)c(C(F)(F)F)c2)c1]

[Compound No. 25: 3-Ethynyl-N-(3-(trifluoromethyl)phenyl)benzamide];

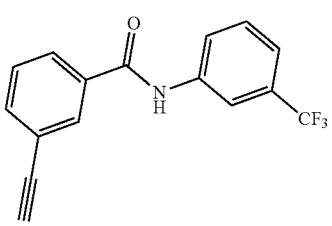 [SMILES: C#Cc1cccc(C(=O)Nc2cccc(C(F)(F)F)c2)c1]

[Compound No. 26: N-(3,5-Bis(trifluoromethyl)phenyl)-3-ethynylbenzamide];

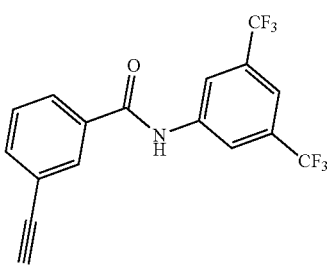 [SMILES: C#Cc1cccc(C(=O)Nc2cc(C(F)(F)F)cc(C(F)(F)F)c2)c1]

[Compound No. 27: 3-Ethynyl-N-(3-(4-methyl-1H-imidazol-1-yl)-5-(trifluoromethyl)phenyl)benzamide];

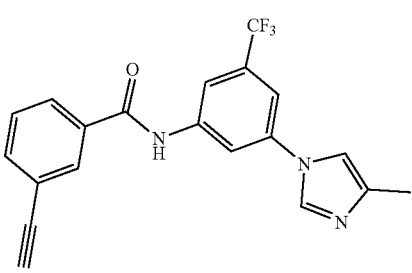 [SMILES: C#Cc1cccc(C(=O)Nc2cc(-n3cnc(C)c3)cc(C(F)(F)F)c2)c1]

[Compound No. 28: 3-Ethynyl-N-(3-(4-methylpiperazin-1-yl)methyl)-5-(trifluoromethyl)phenyl)benzamide];

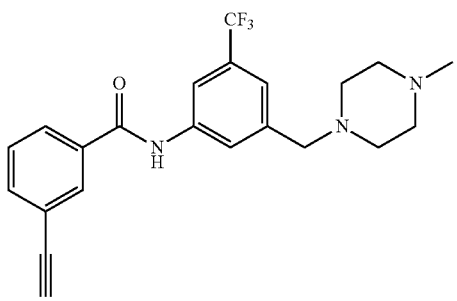 [SMILES: C#Cc1cccc(C(=O)Nc2cc(CN3CCN(C)CC3)cc(C(F)(F)F)c2)c1]

[Compound No. 29: 3-Ethynyl-N-(3-(morpholinomethyl)-5-(trifluoromethyl) phenyl)benzamide];

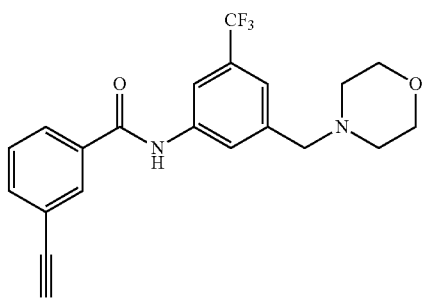 [SMILES: C#Cc1cccc(C(=O)Nc2cc(CN3CCOCC3)cc(C(F)(F)F)c2)c1]

[Compound No. 30: N-(4-Chloro-3-(trifluoromethyl) phenyl)-3-ethynylbenzamide];

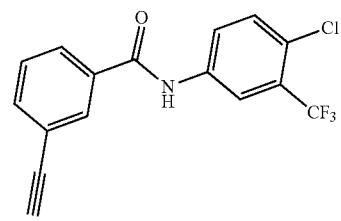 [SMILES: C#Cc1cccc(C(=O)Nc2ccc(Cl)c(C(F)(F)F)c2)c1]

[Compound No. 31: N-(4-((4-Ethylpiperazin-1-yl)methyl)-3-(trifluoromethyl) phenyl)-3-ethynylbenzamide];

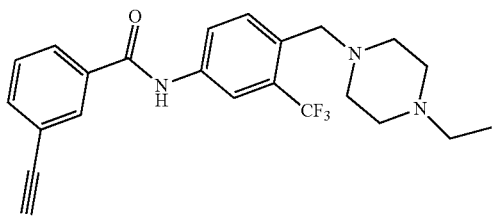 [SMILES: C#Cc1cccc(C(=O)Nc2ccc(CN3CCN(CC)CC3)c(C(F)(F)F)c2)c1]

[Compound No. 32: 3-Ethynyl-N-(4-(morpholinomethyl)-3-(trifluoromethyl) phenyl)benzamide];

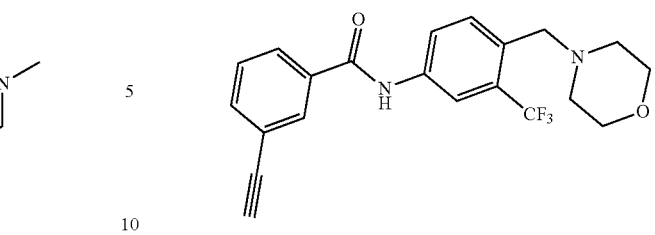

A specific example of step 1 of the compound of Formula 3 for preparing an indazole derived compound preferred as the compound according to the present invention is as follows:

[Compound No. 33: Methyl-3-iodobenzoate]

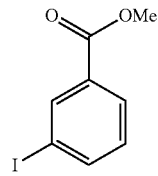

A specific example of step 2 of the compound of Formula 3 for preparing an indazole derived compound preferred as the compound according to the present invention is as follows.

[Compound No. 34: Methyl 3-(((trimethylsilyl)ethynyl)benzoate]

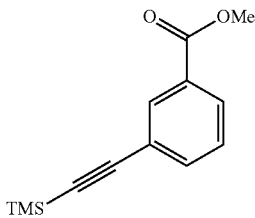 [SMILES: COC(=O)c1cccc(C#C[Si](C)(C)C)c1]

A specific example of step 3 of the compound of Formula 3 for preparing an indazole derived compound preferred as the compound according to the present invention is as follows.

[Compound No. 35: Methyl 3-(((trimethylsilyl)ethynyl)benzoate]

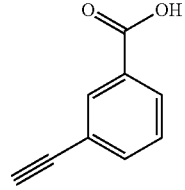

A specific example of the compound of Formula 2 for preparing an indazole derived compound preferred as the compound according to the present invention is as follows.

[Compound No. 36: 4-iodo-1H-indazol-3-amine]

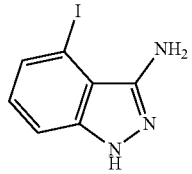

Hereinafter, the present invention will be described in more detail with reference to Examples and Experimental Examples. However, the following Examples and Experimental Examples are provided only for better understanding of the present invention, and should not be construed as limiting the scope of the present invention.

Example 1: Preparation of Compounds of Formula 3 (Compound Nos. 17 to 24)

Example 1-1: Preparation of N-(3-Ethynylphenyl)-3-(trifluoromethyl) benzamide (Compound 17)

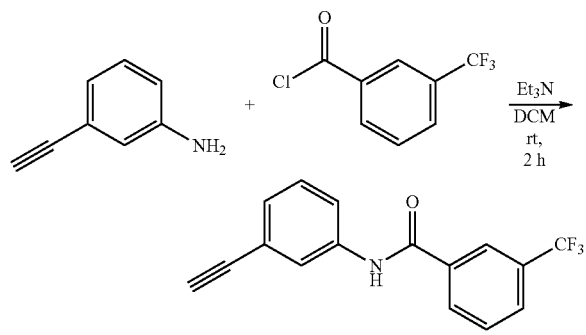

3-Ethynylaniline (134 mg, 1.14 mmol) and 3-(trifluoromethyl)benzoyl chloride (286 mg, 1.37 mmol) were added to DCM (10 mL) and stirred. Triethylamine (346 mg, 3.42 mmol) was slowly added to the resulting suspension and stirred at room temperature under argon atmosphere for 2 hours. The solvent was removed by distillation under reduced pressure, and the obtained residue was purified by column chromatography (SiO$_2$: ethyl acetate-hexane (1:3, v/v)) to obtain 179 mg (54%) of a yellow solid compound.

$^1$H NMR (400 MHz, CDCl$_3$) δ 8.55 (s, 1H), 8.09 (s, 1H), 8.01 (d, J=8.0 Hz, 1H), 7.77-7.43 (m, 2H), 7.66-7.63 (m, 1H), 7.54 (t, J=7.6 Hz, 1H), 7.29-7.27 (m, 2H), 3.08 (s, 1H); $^{13}$C NMR (100 MHz, CDCl$_3$) δ 164.88, 137.52, 135.38, 131.17 (q, J=33 Hz), 130.48, 129.35, 129.06, 128.70, 128.46 (q, J=4 Hz), 124.24, 124.17 (q, J=4 Hz), 123.95 (q, J=271 Hz), 122.96, 121.34, 82.96.

Example 1-2: Preparation of N-(3-Ethynylphenyl)-3,5-bis(trifluoromethyl) benzamide (Compound 18)

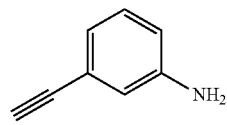

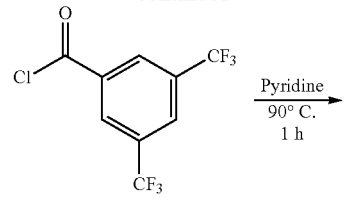

3-Ethynylaniline (56.6 mg, 0.484 mmol) and 3,5-bis(trifluoromethyl)benzoyl chloride (161 mg, 0.581 mmol) were dissolved in pyridine (1 mL) and the resulting solution was stirred while heating at 90° C. under argon atmosphere for 1 hour. The solvent was removed by distillation under reduced pressure, and the obtained residue was purified by column chromatography (SiO$_2$: ethyl acetate-hexane (1:2, v/v)) to obtain 92 mg (53%) of a yellow product.

$^1$H NMR (400 MHz, acetone-d$_6$) δ 10.08 (s, 1H), 8.64 (s, 1H), 8.29 (s, 1H), 8.04 (s, 1H), 7.85 (d, J=8.0 Hz, 1H), 7.41 (t, J=7.6 Hz, 1H), 7.31 (d, J=7.6 Hz, 1H), 3.68 (s, 1H); $^{13}$C NMR (100 MHz, acetone-d$_6$) δ 162.75, 138.88, 137.44, 131.47 (q, J=33 Hz), 129.05, 128.30 (q, J=3.2 Hz), 127.81, 125.02 (q, J=3.7 Hz), 123.60, 123.32 (q, J=270 Hz), 122.80, 120.89, 82.97, 78.38; HRMS (ESI-TOF) m/z calculated for C$_{17}$H$_{10}$F$_6$NO [M+H]$^+$: 358.0667, found: 358.0662.

Example 1-3: Preparation of N-(3-ethynylphenyl)-3-(4-methyl-1H-imidazol-1-yl)-5-(trifluoromethyl) benzamide (Compound 19)

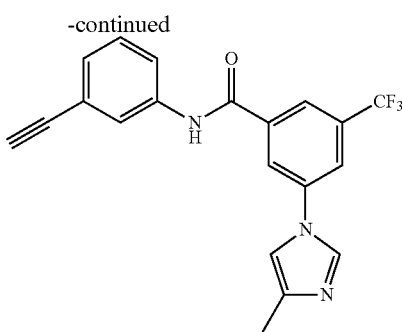

3-Ethynylaniline (109 mg, 0.93 mmol) and 3-(4-methyl-1H-imidazol-1-yl)-5-(trifluoromethyl)benzoic acid (326.8 mg, 1.21 mmol) were dissolved in anhydrous DMF (5 ml) and stirred under argon atmosphere. DIPEA (0.661 mL, 3.72 mmol) and HATU (460 mg, 1.21 mmol) were added to the resulting solution and then the resulting mixture was stirred at room temperature for 18 hours. The reaction was terminated with saturated aqueous NaHCO$_3$ (30 mL), transferred to a separatory funnel and extracted with ethyl acetate (3×20 mL). The ethyl acetate layer was collected, washed once with water and brine, and then dried with anhydrous sodium sulfide. The resulting residue was purified by flash column chromatography on silica gel using ethyl acetate-hexane (1:1, v/v), followed by 100% ethyl acetate to obtain 143 mg (42%) of a compound.

$^1$H NMR (400 MHz, CDCl$_3$) δ 10.45 (s, 1H), 8.20 (s, 1H), 8.15 (s, 1H), 7.77 (s, 2H), 7.74-7.69 (m, 2H), 7.25-7.24 (m, 2H), 7.03 (s, 1H), 3.04 (s, 1H), 2.09 (s, 3H); $^{13}$C NMR (100 MHz, CDCl$_3$) δ 163.68, 140.11, 137.95, 137.66, 137.59, 134.42, 132.79 (q, J=33.4 Hz), 128.99, 128.70, 124.46, 123.48 (q, J=3.5 Hz), 123.32, 122.96 (q, J=271.3 Hz), 122.79, 121.66, 120.23 (q, J=3.5 Hz), 114.78, 92.97, 13.16.

Example 1-4: Preparation of N-(3-ethynylphenyl)-3-fluoro-5-(trifluoromethyl) benzamide (Compound 20)

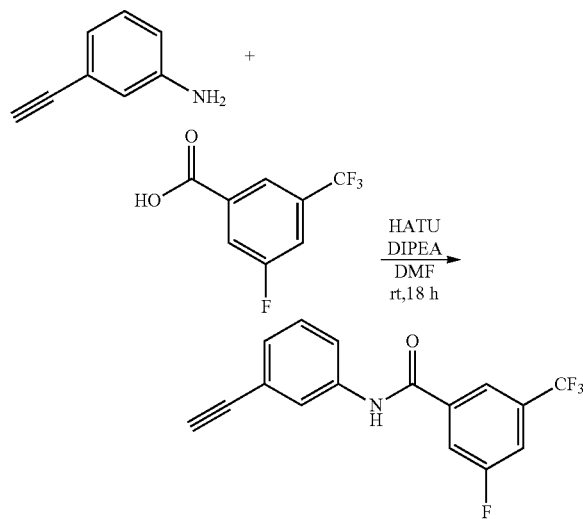

A mixture of 3-ethynylaniline (188 mg, 1.605 mmol) and 3-fluoro-5-(trifluoromethyl)benzoic acid (334 mg, 1.605 mmol) was dissolved in anhydrous DMF (3 mL) and stirred under an argon atmosphere. DIPEA (0.817 mL, 6.42 mmol) and HATU (793 mg, 2.09 mmol) were added to the resulting reaction solution and then the reaction mixture was stirred at room temperature for 18 hours. Then, the reaction solution was quenched with saturated aqueous NaHCO$_3$ (30 mL) and the aqueous layer was extracted with ethyl acetate (3×15 mL). The combined organic layer was washed with water and brine, dried with anhydrous sodium sulfate (Na$_2$SO$_4$) and filtered, and the solvent was removed under reduced pressure. The resulting residue was purified by flash column chromatography on silica gel using ethyl acetate-hexane (1:3, v/v) to obtain the title compound; 460.3 mg (yield 93.3%); $^1$H NMR (400 MHz, CDCl$_3$) δ 8.06 (s, 1H), 7.91 (s, 1H), 7.80 (d, J=8.4 Hz, 1H), 7.75 (s, 1H), 7.69-7.66 (m, 1H), 7.54 (d, J=8.0 Hz, 1H), 7.37-7.29 (m, 2H), 3.12 (s, 1H); $^{13}$C NMR (100 MHz, CDCl$_3$) δ 163.83, 162.24 (q, J=183 Hz), 137.99, 137.92, 137.14, 129.11 (q, J=22 Hz), 124.02, 123.15, 121.10, 119.58, 119.54, 118.16 (q, J=22 Hz), 116.41, 116.16, 82.79, 77.91.

Example 1-4: Preparation of N-(3-Ethynylphenyl)-3-morpholino-5-(trifluoromethyl) benzamide (Compound 21)

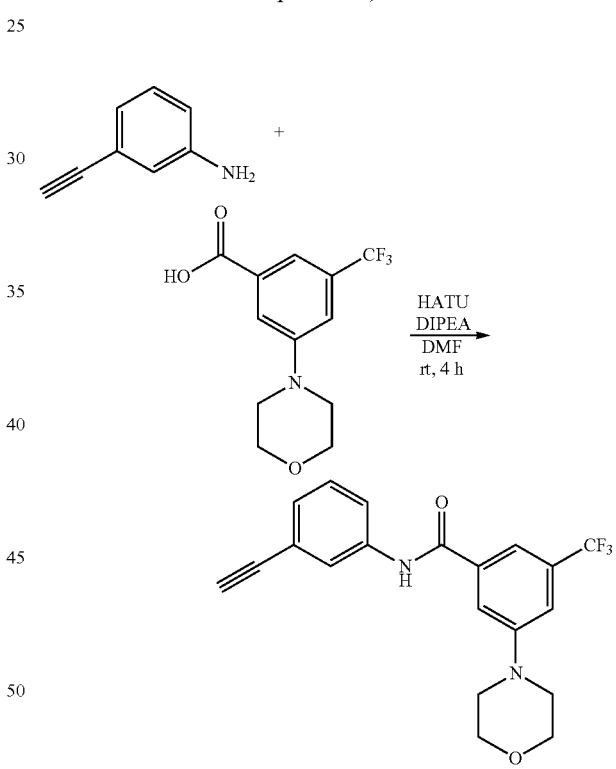

A mixture of 3-ethynylaniline (53 mg, 0.452 mmol) and 3-morpholino-5-(trifluoromethyl)benzoic acid (124.5 mg, 0.452 mmol) was dissolved in anhydrous DMF (1 mL) and stirred under argon atmosphere. DIPEA (0.228 ml, 1.81 mmol) and HATU (344 mg, 0.905 mmol) were added to the resulting reaction solution and then the reaction mixture was stirred at room temperature for 4 hours. Then, the reaction solution was quenched with saturated aqueous NaHCO$_3$ (10 mL) and the aqueous layer was extracted with ethyl acetate (3×10 mL). The combined organic layer was washed with water and brine, dried with anhydrous sodium sulfate (Na$_2$SO$_4$) and filtered, and the solvent was removed under reduced pressure. The resulting oily residue was purified by Example 1-5: Preparation of N-(3-ethynylphenyl)-4-methyl-3-(trifluoromethyl) benzamide (Compound 22)

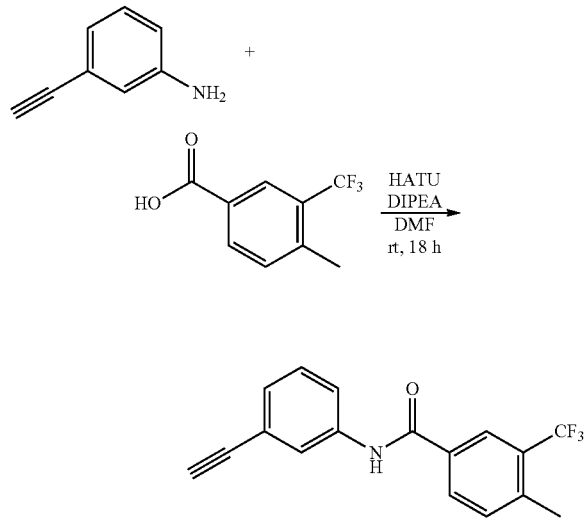

A mixture of 3-ethynylaniline (65 mg, 0.555 mmol) and 4-methyl-3-(trifluoromethyl) benzoic acid (113.2 mg, 0.555 mmol) was dissolved in anhydrous DMF (2 mL) and stirred under argon atmosphere. DIPEA (0.280 mL, 2.22 mmol) and HATU (422 mg, 1.11 mmol) were added to the resulting reaction mixture and the reaction mixture was stirred at room temperature for 18 hours. Then, the reaction mixture was quenched with a saturated aqueous NaHCO$_3$ (15 mL) solution and the aqueous layer was extracted with ethyl acetate (3×10 mL). The combined organic layer was washed with water and brine, dried with anhydrous Na$_2$SO$_4$ and filtered, and the solvent was removed under reduced pressure. The resulting residue was purified by flash column chromatography on silica gel using ethyl acetate-hexane (1:3, v/v) to obtain the title compound; 143.6 mg (yield 84.8%); $^1$H NMR (400 MHz, CDCl$_3$) δ 8.26 (s, 1H), 7.77 (s, 1H), 7.71 (dt, J=7.6 Hz, 2.0 Hz, 1H), 7.59 (s, 1H), 7.46 (s, 1H), 7.36-7.29 (m, 2H), 7.24 (s, 1H), 3.89-3.87 (m, 4H), 3.28-3.25 (m, 4H), 3.11 (s, 1H); $^{13}$C NMR (100 MHz, CDCl$_3$) δ 165.11, 151.78, 137.70, 136.50, 131.95 (q, J=32 Hz), 129.13, 128.55, 123.77 (q, J=271 Hz), 123.87, 122.97, 121.01, 117.21, 114.47 (q, J=3.9 Hz), 113.33 (q, J=3.9 Hz), 83.00, 66.52, 48.25; HRMS (ESI-TOF) m/z calculated for C$_{20}$H$_{18}$F$_3$N$_2$O$_2$ [M+H]$^+$: 375.1320, found: 375.1311.

Example 1-5: Preparation of N-(3-ethynylphenyl)-4-methyl-3-(trifluoromethyl) benzamide (Compound 22)

A mixture of 3-ethynylaniline (65 mg, 0.555 mmol) and 4-methyl-3-(trifluoromethyl) benzoic acid (113.2 mg, 0.555 mmol) was dissolved in anhydrous DMF (2 mL) and stirred under argon atmosphere. DIPEA (0.280 mL, 2.22 mmol) and HATU (422 mg, 1.11 mmol) were added to the resulting reaction mixture and the reaction mixture was stirred at room temperature for 18 hours. Then, the reaction mixture was quenched with a saturated aqueous NaHCO$_3$ (15 mL) solution and the aqueous layer was extracted with ethyl acetate (3×10 mL). The combined organic layer was washed with water and brine, dried with anhydrous Na$_2$SO$_4$ and filtered, and the solvent was removed under reduced pressure. The resulting residue was purified by flash column chromatography on silica gel using ethyl acetate-hexane (1:3, v/v) to obtain the title compound; 160.2 mg (yield 95.2%); $^1$H NMR (400 MHz, CDCl$_3$) δ 8.10 (d, J=1.3 Hz, 1H), 7.99 (br. s, 1H), 7.92 (dd, J=7.9 Hz, 1.8 Hz, 1H), 7.77-7.76 (m, 1H), 7.70 (dt, J=7.6 Hz, 2.0 Hz, 1H), 7.41 (d, J=7.9 Hz, 1H), 7.36-7.31 (m, 2H), 3.10 (s, 1H), 2.57 (s, 3H); $^{13}$C NMR (100 MHz, CDCl$_3$) δ 164.49, 141.11, 137.65, 132.52, 132.46, 130.17, 129.15, 128.55, 125.34, 124.55, 124.60, 123.82, 123.02, 120.95, 82.99, 77.69, 19.43; HRMS (ESI-TOF) m/z calculated for C$_{17}$H$_{13}$F$_3$NO [M+H]$^+$: 304.0949, found: 304.0946.

Example 1-6: Preparation of N-(3-ethynylphenyl)-4-(4-methylpiperazin-1-yl)-3-(trifluoromethyl)benzamide (Compound 23)

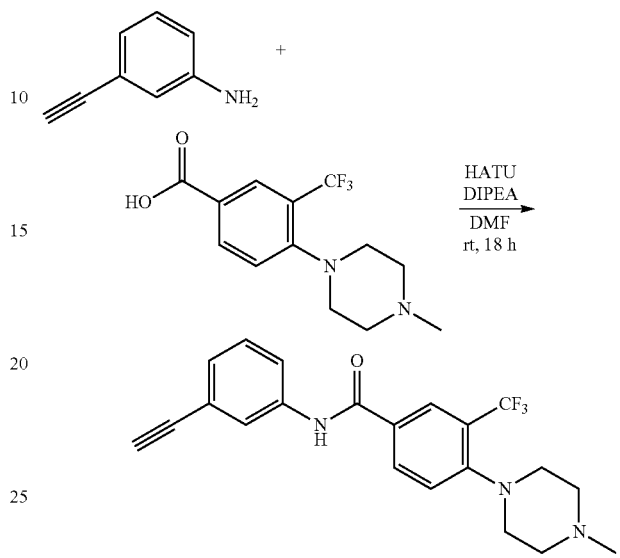

A mixture of 3-ethynylaniline (115 mg, 0.982 mmol) and 4-(4-methylpiperazin-1-yl)-3-(trifluoromethyl) benzoic acid (367.8 mg, 1.276 mmol) was dissolved in anhydrous DMF (5 mL) and stirred under argon atmosphere. DIPEA (0.698 ml, 3.93 mmol) and HATU (485 mg, 1.276 mmol) were added to the resulting reaction mixture and the reaction mixture was stirred at room temperature for 18 hours. Then, the reaction mixture was quenched with a saturated aqueous NaHCO$_3$ solution (30 mL) and the aqueous layer was extracted with ethyl acetate (3×20 mL). The combined organic layer was washed with water and brine, dried with anhydrous Na$_2$SO$_4$ and filtered, and the solvent was removed under reduced pressure. The resulting residue was purified by flash column chromatography on silica gel using ethyl acetate-hexane (1:1, v/v) and then 100% ethyl acetate, to obtain the title compound; 243.4 mg (yield 64%); $^1$H NMR (400 MHz, CDCl$_3$) δ 8.29 (s, 1H), 8.10 (d, J=1.6 Hz, 1H), 7.97 (dd, J=8.4 Hz, 1.6 Hz, 1H), 7.73 (s, 1H), 7.67-7.65 (m, 1H), 7.31-7.25 (m, 2H), 3.07 (s, 1H), 3.04-3.01 (m, 4H), 2.59 (s, 4H), 2.37 (s, 3H); $^{13}$C NMR (100 MHz, CDCl$_3$) δ 164.53, 155.40, 137.77, 131.63, 129.81, 129.05, 128.43, 126.94 (q, J=5.3 Hz), 125.76 (q, J=29.3 Hz), 124.0 (q, J=272 Hz), 123.97, 123.23, 122.91, 121.11, 83.04, 55.15, 53.01, 46.03.

Example 1-7: Preparation of N-(3-ethynylphenyl)-4-morpholino-3-(trifluoromethyl)benzamide (Compound 24)

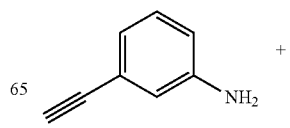

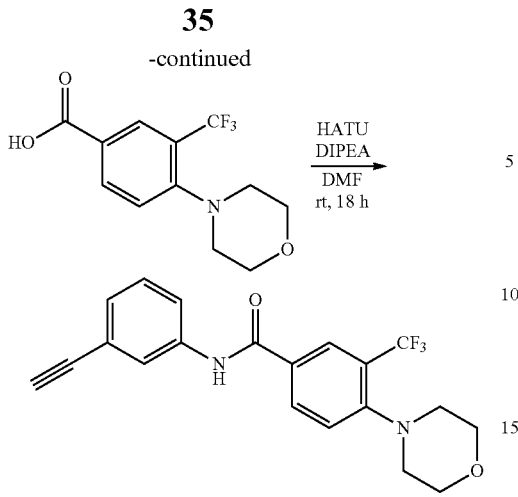

A mixture of 3-ethynylaniline (49.6 mg, 0.423 mmol) and 4-morpholino-3-(trifluoromethyl)benzoic acid (151.4 mg, 0.55 mmol) was dissolved in anhydrous DMF (2 mL) and stirred under argon atmosphere. DIPEA (0.261 mℓ, 1.502 mmol) and HATU (185 mg, 0.488 mmol) were added to the resulting reaction mixture and the reaction mixture was stirred at room temperature for 18 hours. Then, the reaction mixture was quenched with a saturated aqueous NaHCO$_3$ solution (15 mL) and the aqueous layer was extracted with ethyl acetate (3×10 mL). The combined organic layer was washed with water and brine, dried with anhydrous Na$_2$SO$_4$ and filtered, and the solvent was removed under reduced pressure. The resulting residue was purified by flash column chromatography on silica gel using ethyl acetate-hexane (1:3, v/v) to obtain the title compound; 153.9 mg (yield 97.2%); $^1$H NMR (400 MHz, CDCl$_3$) δ 8.42 (s, 1H), 8.12 (d, J=1.6 Hz, 1H), 8.01 (dd, J=8.4 Hz, 1.6 Hz, 1H), 7.73 (s, 1H), 7.68-7.65 (m, 1H), 7.32-7.28 (m, 3H), 3.86-3.84 (m, 4H), 3.08 (s, 1H), 3.00-2.98 (m, 4H); $^{13}$C NMR (100 MHz, CDCl$_3$) δ 164.53, 154.97, 137.74, 131.86, 130.23, 129.06, 128.49, 126.95 (q, J=5.5 Hz), 126.17 (q, J=29.6 Hz), 124.05, 123.62 (q, J=272 Hz), 123.26, 122.91, 121.20, 83.04, 76.75, 67.06, 53.38.

Example 2: Preparation of Compound of Formula 3 (Compound Nos. 25 to 32)

Step 1

Preparation of methyl-3-iodobenzoate (Compound 33)

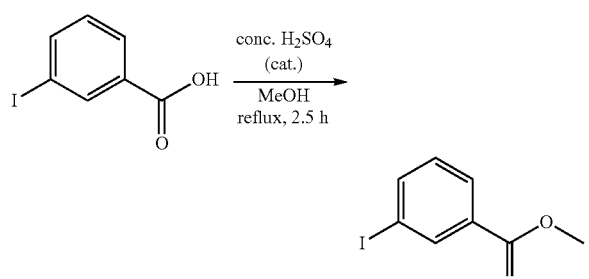

Concentrated sulfuric acid (H$_2$SO$_4$) (3.0 mL) was carefully added to a solution of 3-iodobenzoic acid (3.00 g, 12.1 mmol) dissolved by stirring in methanol (75 mL) and the resulting solution was cooled to room temperature while refluxing under a nitrogen atmosphere for 2.5 hours. Then, the reaction mixture was then diluted with diethyl ether (75 mL) and sequentially washed with water (H$_2$O) (2×75 mL), saturated aqueous sodium hydrogen carbonate (NaHCO$_3$) solution (75 mL), and then brine (75 mL). The organic layer was dried with anhydrous Na$_2$SO$_4$ and filtered, and the solvent was removed under reduced pressure to obtain the compound 33 as a white solid (3.17 g, 99%); $^1$H NMR (400 MHz, CDCl$_3$) δ 8.35 (t, J=1.6 Hz, 1H), 7.98 (m, 1H), 7.86 (m, 1H), 7.16 (t, J=7.8 Hz, 1H), 3.89 (s, 3H).

Step 2

Preparation of methyl 3-((trimethylsilyl) ethynyl) benzoate (Compound 34)

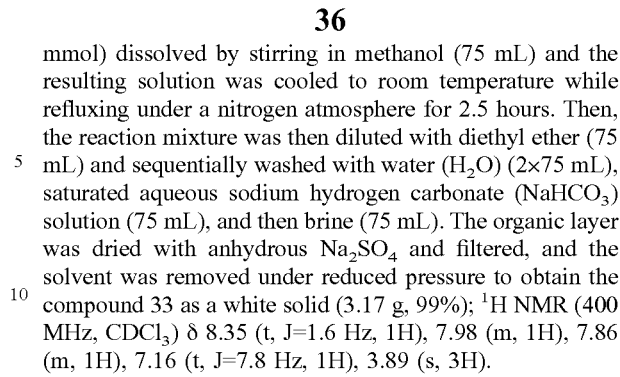

Compound 33 (3.22 g, 12.29 mmol), trimethylsilylacetylene (1.811 g, 18.4 mmol), PdCl$_2$(PPh$_3$)$_2$ (86 mg, 0.123 mmol) and Et$_3$N (20 mL) were dissolved in anhydrous THF (40 mL) while stirring. The reaction mixture was degassed and stirred under argon atmosphere for 15 minutes, and CuI (36 mg, 0.184 mmol) was added thereto. The reaction solution was stirred at room temperature for 18 hours, then diluted with diethyl ether (75 mL), and then washed with 0.1 M HCl solution (2×100 mL), H$_2$O (75 mL) and brine (75 mL). The organic layer was dried with anhydrous Na$_2$SO$_4$ and filtered. The solvent was removed under reduced pressure to obtain compound 34 (3.41 g, 96%) as an orange oil; $^1$H NMR (400 MHz, CDCl$_3$) δ 8.16 (t, J=1.5 Hz, 1H), 7.98 (dt, J=7.8 and 1.2 Hz, 1H), 7.65 (dt, J=7.7 and 1.2 Hz, 1H), 7.39 (t, J=7.8 Hz, 1H), 3.93 (s, 3H), 0.28 (s, 9H); $^{13}$C NMR (100 MHz, CDCl$_3$) δ 166.33, 136.0, 133.10, 130.30, 129.42, 128.36, 123.59, 103.86, 95.35, 52.23, 0.13.

Step 3

Preparation of methyl 3-((trimethylsilyl)ethynyl)benzoate (Compound 35)

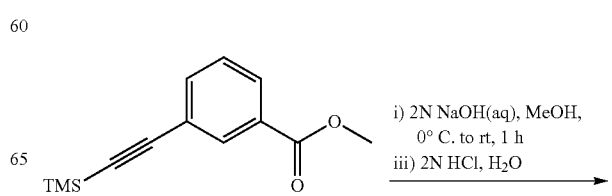

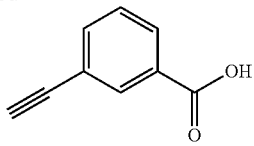

Sodium hydroxide (at a concentration of 2M in H₂O, 15 mL, 28 mmol) was added to a solution of cold compound 34 (3.23 g, 13.9 mmol) dissolved in 0° C. MeOH (75 mL), and the solution was stirred at room temperature for 1 hour. The reaction mixture was concentrated under reduced pressure and acidified with HCl (concentration of 2M in H₂O). The resulting solution was diluted with ethyl acetate (EtOAc) and washed with water and saturated brine. The organic layer was dried with anhydrous Na₂SO₄ and filtered. The solvent was removed under reduced pressure to obtain compound 35 (1.712 g, 84%) as a light brown solid; ¹H NMR (400 MHz, DMSO-d₆) δ 13.0 (br, 1H), 7.98-7.96 (m, 2H), 7.73 (dt, J=7.8 and 1.4 Hz, 1H), 7.54 (t, J=7.8 Hz, 1H), 4.30 (s, 1H); ¹³C NMR (100 MHz, CDCl₃) δ 166.91, 136.23, 132.69, 131.79, 130.13, 129.66, 122.57, 82.93, 82.12.

Step 4

Preparation of 3-ethynyl-N-(3-(trifluoromethyl)phenyl)benzamide (Compound

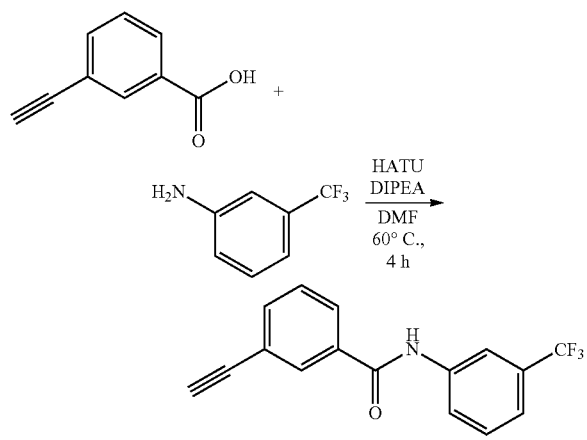

A mixture of 3-ethynylaniline (100 mg, 0.684 mmol) and 3-(trifluoromethyl) aniline (110.2 mg, 0.684 mmol) was dissolved in anhydrous DMF (1 mL) and stirred under argon atmosphere. DIPEA (0.345 ml, 2.737 mmol) and HATU (520.3 mg, 1.368 mmol) were added to the resulting reaction solution and then the reaction mixture was stirred at 60° C. for 4 hours. Then, the reaction solution was quenched with a saturated aqueous NaHCO₃ solution (10 mL) and the aqueous layer was extracted with ethyl acetate (3×10 mL). The combined organic layer was washed with water and brine, dried with anhydrous sodium sulfate (Na₂SO₄) and filtered, and the solvent was removed under reduced pressure. The resulting oily residue was purified by flash column chromatography on silica gel using ethyl acetate-hexane (1:3, v/v) to obtain the title compound; 145.7 mg (yield: 73.6%); ¹H NMR (400 MHz, CDCl₃) δ 8.34 (s, 1H), 7.95 (s, 2H), 7.85 (t, J=8.4 Hz, 2H), 7.64 (d, J=7.6 Hz, 1H), 7.48-7.39 (m, 3H), 3.15 (s, 1H); ¹³C NMR (100 MHz, CDCl₃) δ 165.34, 138.24, 135.47, 134.64, 131.60, 131.28, 130.57, 129.62, 128.96, 127.54, 123.52, 122.96, 121.33 (q, J=3.9 Hz), 117.18 (q, J=4.1 Hz), 82.36, 78.67.

Example 2-1: Preparation of N-(3,5-bis(trifluoromethyl)phenyl)-3-ethynylbenzamide (Compound 26)

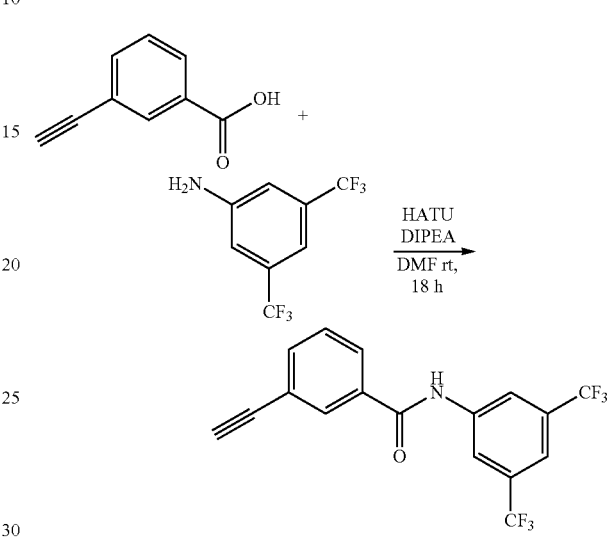

A mixture of 3-ethynylbenzoic acid (99 mg, 0.676 mmol) and 3,5-bis (trifluoromethyl)aniline (155 mg, 0.676 mmol) was dissolved in anhydrous DMF (1 mL) and stirred under argon atmosphere. DIPEA (0.342 ml, 2.71 mmol) and HATU (514 mg, 1.353 mmol) were added to the resulting reaction solution, and then the reaction mixture was stirred at room temperature for 18 hours. Then, the reaction solution was quenched with a saturated aqueous NaHCO₃ solution (10 mL) and the aqueous layer was extracted with ethyl acetate (3×10 mL). The combined organic layer was washed with water and brine, dried with anhydrous sodium sulfate (Na₂SO₄) and filtered, and the solvent was removed under reduced pressure. The resulting oily residue was purified by flash column chromatography on silica gel using ethyl acetate-hexane (1:4, v/v) to obtain the title compound; 57.5 mg (yield 23.8%); ¹H NMR (400 MHz, CDCl₃) δ 8.35 (br. s, 1H), 8.19 (s, 1H), 7.97 (s, 1H), 7.88 (d, J=7.6 Hz, 1H), 7.71-7.68 (m, 2H), 7.48 (t, J=7.6 Hz, 1H), 3.18 (s, 1H); ¹³C NMR (100 MHz, CDCl₃) δ 165.29, 139.11, 135.89, 134.02, 132.49 (q, J=33.4 Hz), 130.47, 129.16, 127.54, 123.19, 123.0 (q, J=271.3 Hz), 119.98, 118.05, 82.13, 78.91.

Example 2-2: Preparation of 3-ethynyl-N-(3-(4-methyl-1H-imidazol-1-yl)-5-(trifluoromethyl)phenyl)benzamide (Compound 27)

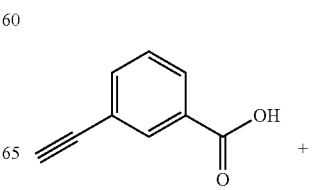

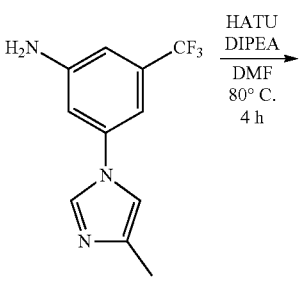

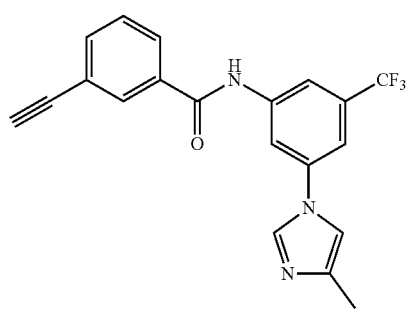

A mixture of 3-ethynylbenzoic acid (60.5 mg, 0.415 mmol) and 3-(4-methyl-1H-imidazol-1-yl)-5-(trifluoromethyl)phenyl) aniline (100 mg, 0.415 mmol) was dissolved in anhydrous DMF (2 mL) and stirred under argon atmosphere. DIPEA (0.342 ml, 2.71 mmol) and HATU (514 mg, 1.353 mmol) were added to the resulting reaction solution and then the reaction mixture was stirred at 60° C. for 4 hours. Then, the reaction solution was quenched with a saturated aqueous NaHCO$_3$ (10 mL) solution and the aqueous layer was extracted with ethyl acetate (3×10 mL). The combined organic layer was washed with water and brine, dried with anhydrous sodium sulfate (Na$_2$SO$_4$) and filtered, and the solvent was removed under reduced pressure. The resulting oily residue was purified by flash column chromatography on silica gel using ethyl acetate-hexane (1:2, v/v) to obtain the title compound; 80 mg (yield 52.3%); $^1$H NMR (400 MHz, CDCl$_3$) δ 10.03 (s, 1H), 8.26 (s, 1H), 8.05 (s, 1H), 7.94-7.92 (m, 2H), 7.80 (s, 1H), 7.63 (d, J=8.0 Hz, 1H), 7.34-7.29 (m, 2H), 7.06 (s, 1H), 3.15 (s, 1H), 2.25 (s, 3H); 13C NMR (100 MHz, CDCl$_3$) δ 165.89, 140.88, 138.25, 136.15, 135.48, 134.47, 132.85 (q, J=33.1 Hz), 131.08, 130.32, 128.77, 128.57, 128.05, 127.05, 123.27 (q, J=271.3 Hz), 122.69, 122.54, 115.68, 82.45, 79.0, 13.49.

Example 2-3: Preparation of 3-ethynyl-N-(3-((4-methylpiperazin-1-yl)methyl)-5-(trifluoromethyl) phenyl)benzamide (Compound 28)

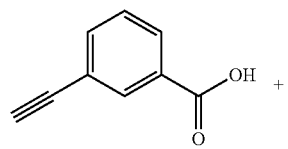

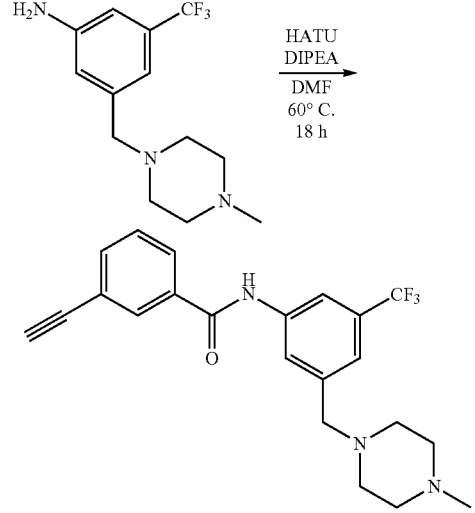

A mixture of 3-ethynylbenzoic acid (95.5 mg, 0.654 mmol) and 3-((4-methylpiperazin-1-yl)methyl)-5-trifluoromethylaniline (143 mg, 0.523 mmol) was dissolved in anhydrous DMF (3 mL) and stirred under argon atmosphere. DIPEA (0.457 ml, 2.616 mmol) and HATU (323 mg, 0.85 mmol) were added to the resulting reaction solution, and then the reaction mixture was stirred at 60° C. for 18 hours. Then, the reaction solution was quenched with a saturated aqueous NaHCO$_3$ (30 mL) solution and the aqueous layer was extracted with ethyl acetate (3×20 mL). The combined organic layer was washed with water and brine, dried with anhydrous sodium sulfate (Na$_2$SO$_4$) and filtered, and the solvent was removed under reduced pressure. The resulting oily residue was purified by flash column chromatography on silica gel using ethyl acetate-hexane containing 5% methanol to obtain the title compound: 142.2 mg (yield 67.7%); $^1$H NMR (400 MHz, CDCl$_3$) δ 8.25 (s, 1H), 7.97 (s, 1H), 7.94 (s, 1H), 7.87 (d, J=8.0 Hz, 1H), 7.79 (s, 1H), 7.66 (d, J=7.6, 1H), 7.45 (t, J=7.6, 1H), 7.38 (s, 12H), 3.54 (s, 2H), 3.16 (s, 1H), 2.50 (s, 8H), 2.32 (s, 3H); $^{13}$C NMR (100 MHz, CDCl$_3$) δ 165.10, 140.80, 138.34, 135.47, 134.69, 131.38 (q, J=32 Hz), 130.56, 129.01, 127.54, 125.22, 123.67, 122.98, 121.64 (q, J=3 Hz), 115.95 (q, J=4 Hz), 82.37, 78.68, 62.17, 55.03, 52.89, 45.90.

Example 2-4: Preparation of 3-ethynyl-N-(3-(morpholinomethyl)-5-(trifluoromethyl) phenyl)benzamide (Compound 29)

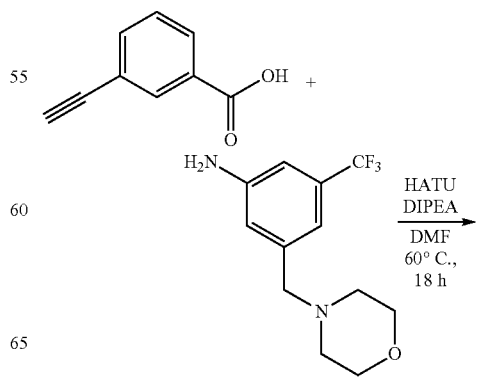

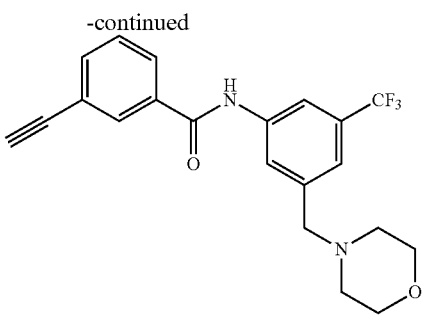

A mixture of 3-ethynylbenzoic acid (140 mg, 0.959 mmol) and 3-morpholinomethyl-5-trifluoromethyl aniline (199.6 mg, 0.767 mmol) was dissolved in anhydrous DMF (3 mL) and stirred under argon atmosphere. DIPEA (0.670 ml, 3.84 mmol) and HATU (474 mg, 1.247 mmol) were added to the resulting reaction solution, and then the reaction mixture was stirred at 60° C. for 18 hours. Then, the reaction solution was quenched with a saturated aqueous NaHCO$_3$ (30 mL) solution and the aqueous layer was extracted with ethyl acetate (3×20 mL). The combined organic layer was washed with water and brine, dried with anhydrous sodium sulfate (Na$_2$SO$_4$) and filtered, and the solvent was removed under reduced pressure. The resulting oily residue was purified by flash column chromatography on silica gel using ethyl acetate-hexane (1:1, v/v) and then ethyl acetate to obtain the title compound: 133 mg (yield: 44.7%); $^1$H NMR (400 MHz, CDCl$_3$) δ 8.69 (s, 1H), 7.97 (s, 1H), 7.88-7.86 (m, 3H), 7.64 (d, J=8.0, 1H), 7.43-7.38 (m, 2H), 3.72-3.70 (m, 4H), 3.50 (s, 1H), 2.45 (s, 4H); $^{13}$C NMR (100 MHz, CDCl$_3$) δ 165.35, 140.04, 138.58, 135.40, 134.68, 131.32 (q, J=32.2 Hz), 130.64, 128.89, 127.67, 125.20, 123.84, 122.85, 121.54 (q, J=3.7 Hz), 116.06 (q, J=3.7 Hz), 82.42, 78.66, 66.90, 62.60, 53.00.

Example 2-5: Preparation of N-(4-chloro-3-(trifluoromethyl)phenyl)-3-ethynylbenzamide (Compound 30)

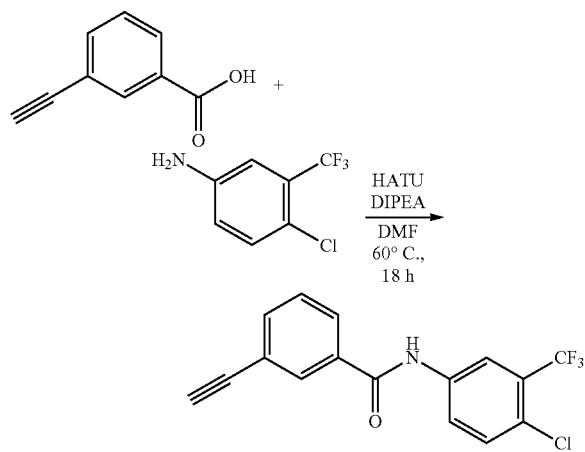

A mixture of 3-ethynylbenzoic acid (161.5 mg, 1.11 mmol) and 4-chloro-3-trifluoromethylaniline (216 mg, 1.11 mmol) was dissolved in anhydrous DMF (4 mL) and stirred under argon atmosphere. DIPEA (0.565 ml, 4.44 mmol) and HATU (549 mg, 1.443 mmol) were added to the resulting reaction solution and then the reaction mixture was stirred at 60° C. for 18 hours. Then, the reaction solution was quenched with a saturated aqueous NaHCO$_3$ (30 mL) solution and the aqueous layer was extracted with ethyl acetate (3×20 mL). The combined organic layer was washed with water and brine, dried with anhydrous sodium sulfate (Na$_2$SO$_4$) and filtered, and the solvent was removed under reduced pressure. The resulting oily residue was purified by flash column chromatography on silica gel using ethyl acetate-hexane (1:3, v/v) to obtain the title compound: 137.7 mg (yield 38.3%); $^1$H NMR (400 MHz, CDCl$_3$) δ 8.63 (s, 1H), 7.96 (d, J=2.4 Hz, 1H), 7.91 (s, 1H), 7.85-7.80 (m, 2H), 7.63 (d, J=7.6 Hz, 1H), 7.44-7.37 (m, 2H), 3.15 (s, 1H); $^{13}$C NMR (100 MHz, CDCl$_3$) δ 165.58, 136.55, 135.60, 134.27, 131.97, 130.61, 128.91 (q, J=4.9 Hz), 128.58, 127.53, 127.43, 124.54, 122.48 (q, J=271.7 Hz), 122.96, 119.56 (q, J=5.4 Hz), 82.26, 78.75.

Example 2-6: Preparation of N-(4-((4-ethylpiperazin-1-yl)methyl)-3-(trifluoromethyl)phenyl)-3-ethynylbenzamide (Compound 31)

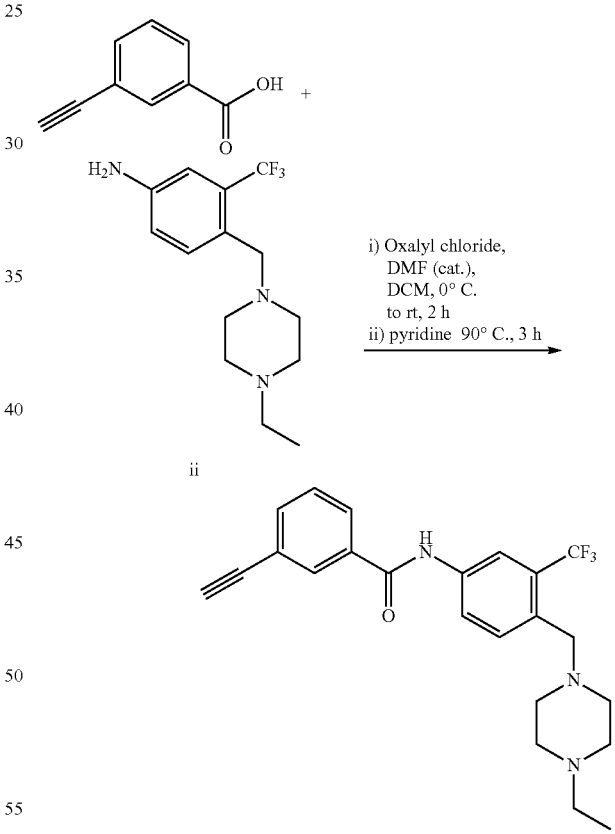

The pyridine (3 ml) containing a solution prepared by stirring 3-ethynylbenzoyl chloride (60.5 mg, 0.415 mmol) and 4-((4-ethylpiperazin-1-yl)methyl)-3-(trifluoromethyl) aniline (100 mg, 0.415 mmol) was heated at 90° C. for 3 hours. The solvent was evaporated under reduced pressure, and the resulting residue was purified by flash column chromatography on silica gel using 100% ethyl acetate and then ethyl acetate containing 5% methanol to obtain the title compound: 136.4 mg (yield 46.6%); $^1$H NMR (400 MHz, CDCl$_3$) δ 8.48 (s, 1H), 7.95 (s, 1H), 7.86-82 (m, 3H), 7.74

(d, J=8.1 Hz, 1H), 7.62 (dt, J=7.7 Hz, 1.2 Hz, 1H), 7.39 (t, J=7.8 Hz, 1H), 3.62 (s, 2H), 3.14 (s, 1H), 2.51-2.38 (m, 10H), 1.10 (t, J=5.2 Hz, 3H); $^{13}$C NMR (100 MHz, CDCl$_3$) δ 165.30, 145.06, 136.45, 135.33, 134.75, 133.99, 131.89, 131.31, 130.61, 128.87, 127.60, 123.57, 122.85, 117.83, 82.43, 78.61, 57.82, 53.15, 53.05, 52.95, 52.91, 52.31, 12.02.

Example 2-7: Preparation of 3-ethynyl-N-(4-(morpholinomethyl)-3-(trifluoromethyl)phenylbenzamide (Compound 32)

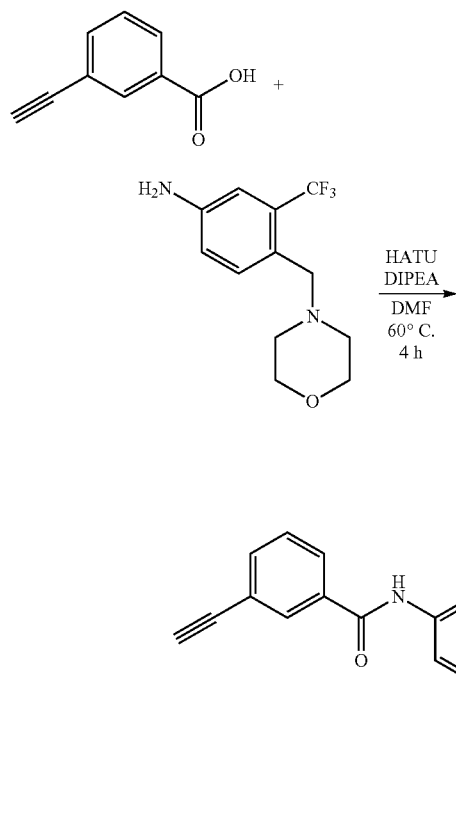

A mixture of 3-ethynylbenzoic acid (40.1 mg, 0.275 mmol) and 4-morpholinomethyl-3-trifluoromethylaniline (71.7 mg, 0.275 mmol) was dissolved in anhydrous DMF (2 mL) and stirred under argon atmosphere. DIPEA (0.139 ml, 1.1 mmol) and HATU (209 mg, 0.55 mmol) were added to the resulting reaction solution, and then the reaction mixture was stirred at 60° C. for 4 hours. Then, the reaction solution was quenched with a saturated aqueous NaHCO$_3$ solution (10 mL) and the aqueous layer was extracted with ethyl acetate (3×20 mL). The combined organic layer was washed with water and brine, dried with anhydrous sodium sulfate (Na$_2$SO$_4$) and filtered, and the solvent was removed under reduced pressure. The resulting oily residue was purified by flash column chromatography on silica gel using ethyl acetate-hexane (1:2, v/v), ethyl acetate-hexane (1:1, v/v) and finally 100% ethyl acetate to obtain the title compound: 46.4 mg (yield 43.45%); $^1$H NMR (400 MHz, CDCl$_3$) δ 8.24 (s, 1H), 7.98 (s, 1H), 7.91-7.87 (m, 3H), 7.79 (d, J=8.4 Hz, 1H), 7.68 (d, J=7.6 Hz, 1H), 7.46 (t, J=8.0 Hz, 1H), 3.76-3.74 (m, 4H), 3.65 (s, 2H), 3.18 (s, 1H), 2.51-2.49 (m, 4H); $^{13}$C NMR (100 MHz, CDCl$_3$) δ 165.11, 136.60, 135.45, 134.71, 133.40, 131.46, 130.51, 129.38 (q, J=30.5 Hz), 128.98, 128.09, 127.59, 123.52 (q, J=271.4 Hz), 122.64, 117.75 (q, J=5.9 Hz), 82.40, 78.67, 67.07, 58.25, 53.59; HRMS (ESI-TOF) m/z calculated for C$_{21}$H$_{20}$F$_3$N$_2$O$_2$ [M+H]$^+$: 389.1477, found: 389.1473.

Example 3: Preparation of Compound of Formula 2 (Compound No. 36)

Example 3-1: Preparation of 4-iodo-1H-indazol-3-amine (Compound 36)

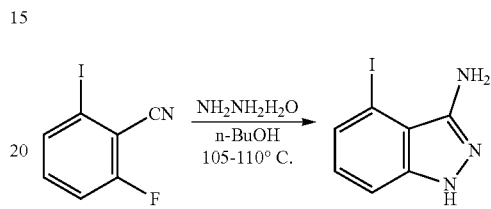

A heated mixture of 2-fluoro-6-iodobenzonitrile (3.0 g, 12.145 mmol) and hydrazine monohydrate (8 mL) was added to n-butanol (40 mL), and the resulting solution was stirred and heated at 110° C. for 6 hours. The reaction mixture was cooled to room temperature and quenched with a mixture of ethyl acetate and water. The aqueous layer was extracted with ethyl acetate (3×50 mL), and the combined organic layer was washed with water and brine and dried with anhydrous Na$_2$SO$_4$. The residue was filtered and the solvent was removed under reduced pressure to obtain the title compound as a pure brown solid: 3.084 g (yield 98%); $^1$H NMR (400 MHz, DMSO-d$_6$) δ 11.80 (s, 1H), 7.35 (d, J=7.2 Hz, 1H), 7.30 (d, J=8.4 Hz, 1H), 6.94 (t, J=7.6 Hz, 1H), 5.06 (s, 2H); $^{13}$C NMR (100 MHz, DMSO-d$_6$) δ 148.98, 141.90, 128.74, 128.10, 115.02, 110.52, 86.35.

Example 4: Preparation of Compound of Formula 1 (Compound Nos. 1 to

Example 4-1: Preparation of N-(3-((3-amino-1H-indazol-4-yl)ethynyl)phenyl)-3-(trifluoromethyl)benzamide (Compound 1)

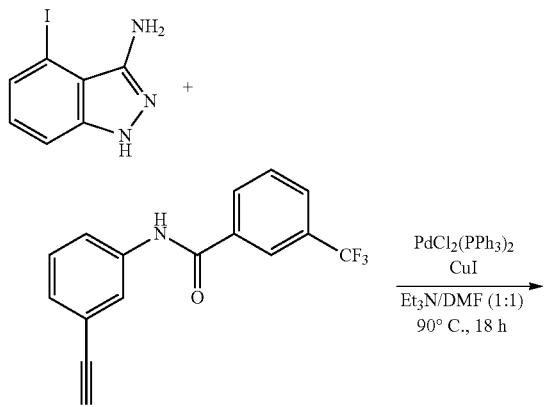

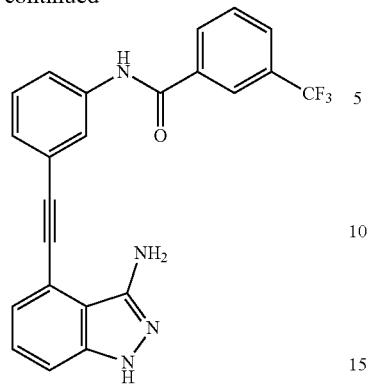

A solution of Compound 36 (75 mg, 0.29 mmol) and N-(3-ethynylphenyl)-3-(trifluoromethyl) benzamide (84 mg, 0.29 mmol) was added to DMF/Et$_3$N (1:1, v/v (4 mL)) and stirred, and PdCl$_2$(PPh$_3$)$_2$ (4.2 mg, 0.006 mmol) and CuI (2.3 mg, 0.012 mmol) were added to the resulting solution. The solution was purged with argon for 15 minutes, sealed and heated at 85 to 90° C. for 18 hours. The solvent was evaporated under reduced pressure, and H$_2$O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na$_2$SO$_4$ and then filtered. The solvent was evaporated under reduced pressure and the resulting residue was purified by flash column chromatography on silica gel using ethyl acetate-hexane (1:1, v/v) and then ethyl acetate-hexane (2:1, v/v) to obtain the title compound as a pure gray solid: 68.3 mg (yield 56%); $^1$H NMR (400 MHz, acetone-d$_6$) δ 11.13 (br. s, 1H), 9.99 (s, 1H), 8.37-8.34 (m, 2H), 8.18 (s, 1H), 7.96-7.93 (m, 2H), 7.79 (t, J=8.0 Hz, 1H), 7.47-7.40 (m, 3H), 7.32 (t, J=7.6 Hz, 1H), 7.21 (d, J=6.8 Hz, 1H), 5.10 (s, 2H); $^{13}$C NMR (100 MHz, acetone-d$_6$) δ 164.28, 139.44, 136.08, 131.87, 131.77, 131.45, 130.42, 130.09, 129.62, 129.19, 128.70, 128.15 (d, J=3 Hz), 127.07, 126.53, 125.50, 124.30 (d, J=4 Hz), 123.16, 122.95, 120.89, 114.70, 110.89, 92.99, 87.07.

Example 4-2: Preparation of N-(3-((3-amino-1H-indazol-4-yl)ethynyl)phenyl)-3,5-bis(trifluoromethyl)benzamide (Compound 2)

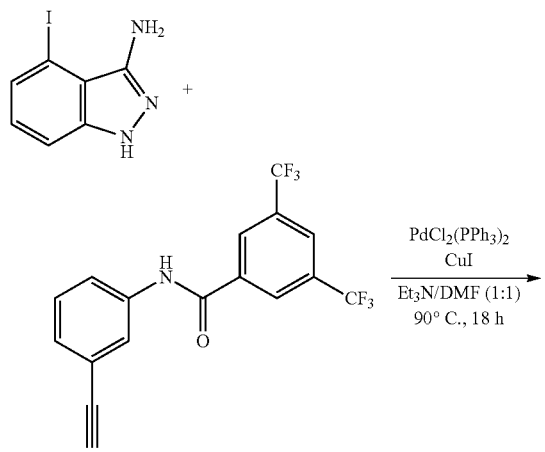

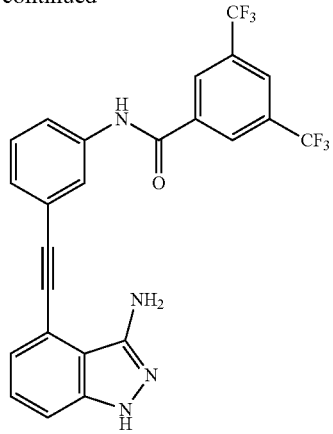

A solution of Compound 36 (51.4 mg, 0.199 mmol) and N-(3-ethynylphenyl)-3,5-bis(trifluoromethyl)benzamide (71 mg, 0.199 mmol) was added to DMF/Et$_3$N (1:1, v/v (4 mL)) and stirred, and PdCl$_2$(PPh$_3$)$_2$ (2.7 mg, 0.004 mmol) and CuI (1.4 mg, 0.0078 mmol) were added to the resulting solution. The solution was purged with argon for 15 minutes, sealed, and heated at 85 to 90° C. for 18 hours. The solvent was evaporated under reduced pressure, and H$_2$O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na$_2$SO$_4$ and then filtered. The solvent was evaporated under reduced pressure, and the resulting residue was purified by flash column chromatography on silica gel using ethyl acetate-hexane (1:1, v/v) and then ethyl acetate-hexane (2:1, v/v) to obtain the title compound as a pure gray solid: 60.5 mg (yield 62.3%); $^1$H NMR (400 MHz, acetone-d$_6$) δ 10.99 (s, 1H), 10.14 (s, 1H), 8.64 (s, 2H), 8.29 (s, 1H), 8.11 (s, 1H), 7.89 (d, J=5.6 Hz, 1H), 7.43-7.33 (m, 4H), 7.20 (d, J=6.0 Hz, 1H), 5.35 (br. s, 2H); $^{13}$C NMR (100 MHz, acetone-d$_6$) δ 162.76, 139.04, 137.41, 131.95, 131.62, 131.29, 130.95, 129.24, 128.34, 127.45, 127.36, 125.07, 124.68, 123.65, 123.08, 123.02, 121.98, 120.98, 111.09, 93.25, 86.83.

Example 4-3: Preparation of N-(3-((3-amino-1H-indazol-4-yl)ethynyl)phenyl)-3-(4-methyl-1H-imidazol-1-yl)-5 (trifluoromethyl)benzamide (Compound 3)

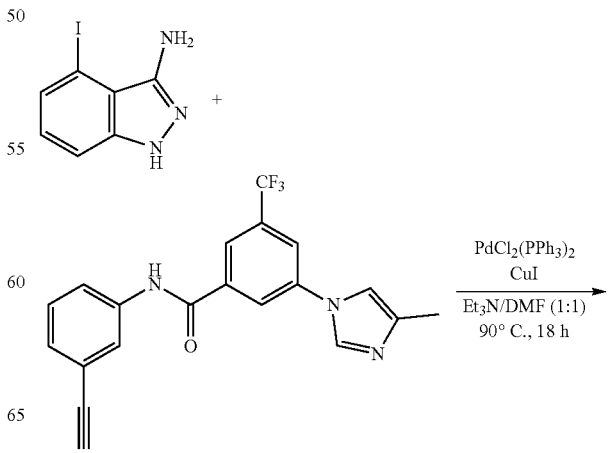

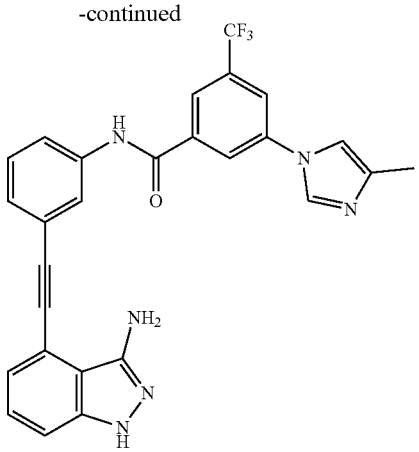

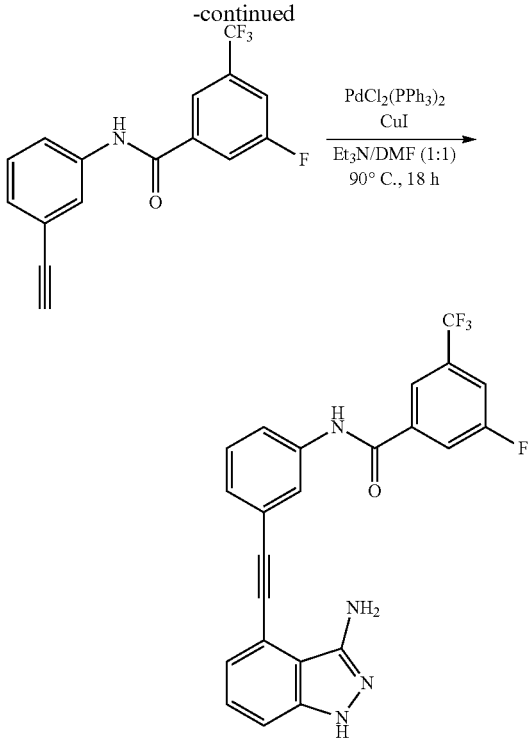

A solution of Compound 36 (45.7 mg, 0.177 mmol) and N-(3-ethynylphenyl)-3-(4-methyl-imidazol-1-yl)-5-(trifluoromethyl)benzamide (78.3 mg, 0.212 mmol) was added to DMF/Et$_3$N (2:3, v/v (5 mL)) and stirred, and PdCl$_2$(PPh$_3$)$_2$ (6.3 mg, 0.009 mmol) and CuI (3.3 mg, 0.0176 mmol) were added to the resulting solution. The solution was purged with argon for 15 minutes, sealed and heated at 85 to 90° C. for 18 hours. The solvent was evaporated under reduced pressure, and H$_2$O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na$_2$SO$_4$ and then filtered. The solvent was evaporated under reduced pressure and the resulting residue was purified by flash column chromatography on silica gel using dichloromethane containing 2-5% methanol to obtain the title compound as a pure solid: 29.1 mg (yield 33%); $^1$H NMR (400 MHz, acetone-d$_6$) δ 11.10 (br. s, 1H), 10.10 (s, 1H), 8.51 (s, 1H), 8.28 (s, 2H), 8.17 (d, J=12.8 Hz, 2H), 7.95 (d, J=8.0 Hz, 1H), 7.57 (s, 1H), 7.52-7.41 (m, 3H), 7.32 (t, J=7.6 Hz, 1H), 7.21 (d, J=6.8 Hz, 1H), 4.98 (br. s, 2H), 2.24 (s, 3H); $^{13}$C NMR (100 MHz, acetone-d$_6$) δ 163.39, 149.02, 141.97, 139.95, 139.27, 138.49, 137.96, 134.99, 132.08, 131.76, 129.29, 127.29, 126.36, 124.97, 123.90, 123.24, 122.99, 120.85, 120.00, 115.17, 114.54, 114.12, 112.98, 110.83, 92.75, 87.19; HRMS (ESI-TOF) m/z calculated for C$_{27}$H$_{20}$F$_3$N$_6$O [M+H]$^+$: 501.1651, found: 501.1650.

Example 4-4: Preparation of N-(3-((3-amino-1H-indazol-4-yl)ethynyl)phenyl)-3-fluoro-5-(trifluoromethyl) benzamide (Compound 4)

A solution of Compound 36 (60 mg, 0.232 mmol) and N-(3-ethynylphenyl)-3-fluoro-5-(trifluoromethyl)benzamide (71.2 mg, 0.232 mmol) was added to DMF/Et$_3$N (1:1, v/v (4 mL)) and stirred, and PdCl$_2$(PPh$_3$)$_2$ (3.2 mg, 0.0046 mmol) and CuI (1.7 mg, 0.0092 mmol) were added to the resulting solution. The solution was purged with argon for 15 minutes, sealed and heated at 85 to 90° C. for 18 hours. The solvent was evaporated under reduced pressure, and H$_2$O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na$_2$SO$_4$ and then filtered. The solvent was evaporated under reduced pressure and the resulting residue was purified by flash column chromatography on silica gel using ethyl acetate-hexane (1:1, v/v) and then 100% ethyl acetate to obtain the title compound as a pure solid: 11.5 mg (yield 11.3%); $^1$H NMR (400 MHz, acetone-d$_6$) δ 8.23 (s, 1H), 8.14-8.11 (m, 2H), 7.92 (d, J=8.0 Hz, 1H), 7.80 (d, J=8.4 Hz, 1H), 7.51-7.40 (m, 3H), 7.31 (t, J=8.0 Hz, 1H), 7.21 (d, J=7.2 Hz, 1H), 4.97-4.95 (m, 2H); $^{13}$C NMR (100 MHz, acetone-d$_6$) δ 163.75, 162.88, 161.28, 139.19, 129.26, 127.27, 126.37, 123.25, 123.07, 122.94, 122.85, 120.88, 120.78, 120.46, 120.42, 118.80, 118.57, 115.81, 115.57, 114.56, 110.84, 92.73, 87.17.

Example 4-5: Preparation of N-(3-((3-amino-1H-indazol-4-yl)ethynyl)phenyl)-3-morpholino-5-(trifluoromethyl) benzamide (Compound 5)

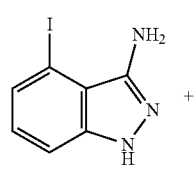 +

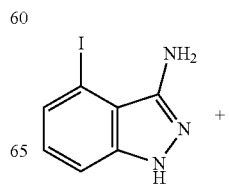 +

-continued

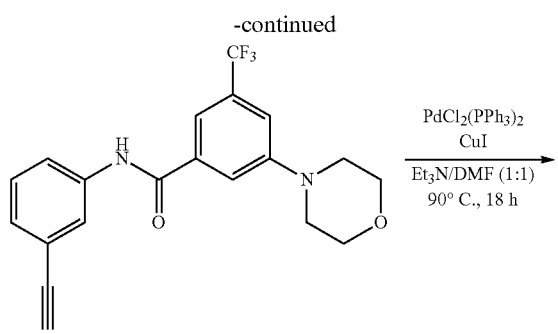

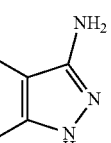

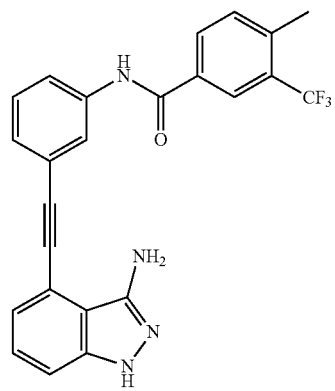

A solution of Compound 36 (60 mg, 0.232 mmol) and N-(3-ethynylphenyl)-3-fluoro-5-(trifluoromethyl)benzamide (86.7 mg, 0.232 mmol) was added to DMF/Et$_3$N (1:1, v/v (4 mL)) and stirred, and PdCl$_2$(PPh$_3$)$_2$ (3.2 mg, 0.0046 mmol) and CuI (1.7 mg, 0.0092 mmol) were added to the resulting solution. The solution was purged with argon for 15 minutes, sealed and heated at 85 to 90° C. for 18 hours. The solvent was evaporated under reduced pressure, and H$_2$O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na$_2$SO$_4$ and then filtered. The solvent was evaporated under reduced pressure, and the resulting residue was purified by flash column chromatography on silica gel using ethyl acetate-hexane (2:1, v/v) and then 100% ethyl acetate to obtain the title compound as a pure gray solid: 68.6 mg (yield 58.6%); $^1$H NMR (400 MHz, DMSO) δ 11.82 (br. s, 1H), 10.50 (s, 1H), 8.04 (s, 1H), 7.87 (d, J=8.4 Hz, 1H), 7.75 (s, 1H), 7.69 (s, 1H), 7.48 (t, J=7.6 Hz, 1H), 7.41-7.39 (m, 2H), 7.35 (d, J=8.0 Hz, 1H), 7.28 (t, J=8.4 Hz, 1H), 7.16 (d, J=7.2 Hz, 1H), 5.16 (s, 2H), 3.79 (t, J=4.8 Hz, 4H), 3.34-3.31 (m, 4H); $^{13}$C NMR (100 MHz, DMSO) δ 165.12, 151.95, 141.75, 139.68, 136.90, 130.83, 130.51, 129.79, 127.35, 126.85, 125.95, 123.43, 123.24, 122.78, 121.74, 120.48, 117.70, 114.40, 114.29, 113.98, 111.53, 93.33, 87.59, 66.36, 48.16.

Example 4-6: Preparation of N-(3-((3-amino-1H-indazol-4-yl)ethynyl)phenyl)-4-methyl-3-(trifluoromethyl) benzamide (Compound 6)

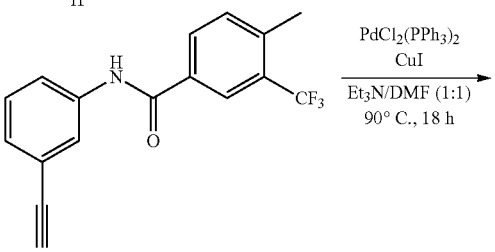

A solution of Compound 36 (60 mg, 0.232 mmol) and N-(3-ethynylphenyl)-3-fluoro-5-(trifluoromethyl)benzamide (70.2 mg, 0.232 mmol) was added to DMF/Et$_3$N (1:1, v/v (4 mL)) and stirred, and PdCl$_2$(PPh$_3$)$_2$ (3.2 mg, 0.0046 mmol) and CuI (1.7 mg, 0.0092 mmol) were added to the resulting solution. The solution was purged with argon for 15 minutes, sealed and heated at 85 to 90° C. for 18 hours. The solvent was evaporated under reduced pressure, and H$_2$O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na$_2$SO$_4$ and then filtered. The solvent was evaporated under reduced pressure, and the resulting residue was purified by flash column chromatography on silica gel using ethyl acetate-hexane (1:1, v/v) and then ethyl acetate-hexane (3:1, v/v) to obtain the title compound as a pure gray solid: 55.5 mg (yield 55.2%); $^1$H NMR (400 MHz, DMSO) δ 11.83 (s, 1H), 10.55 (s, 1H), 8.28 (s, 1H), 8.19 (d, J=7.6 Hz, 1H), 8.07 (s, 1H), 7.87 (d, J=8.0 Hz, 1H), 7.64 (d, J=7.6 Hz, 1H), 7.48 (t, J=8.0 Hz, 1H), 7.41-7.34 (m, 2H), 7.28 (t, J=8.0 Hz, 1H), 7.16 (d, J=6.8 Hz, 1H), 5.17 (s, 2H), 2.54-2.51 (m, 3H); $^{13}$C NMR (100 MHz, DMSO) δ 164.65, 143.20, 141.77, 140.54, 139.75, 133.06, 132.97, 132.06, 129.77, 128.00 (q, J=30 Hz), 127.29, 126.84, 125.45 (q, J=6 Hz), 123.38, 123.27 (q, J=6 Hz), 122.74, 121.63, 114.31, 111.52, 93.38, 87.57, 19.27.

Example 4-7: Preparation of N-(3-((3-amino-1H-indazol-4-yl)ethynyl)phenyl)-4-(4-methylpiperazin-1-yl)-3-(trifluoromethyl)benzamide (Compound 7)

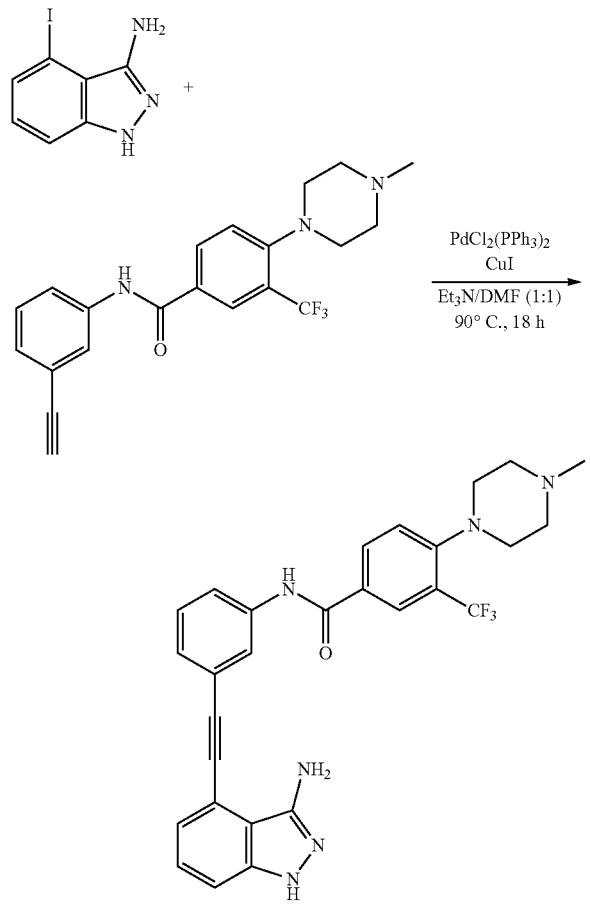

A solution of Compound 36 (51.8 mg, 0.20 mmol) and N-(3-ethynylphenyl)-4-(4-methylpiperazin-1-yl)-3-(trifluoromethyl)benzamide (93 mg, 0.24 mmol) was added to DMF/Et$_3$N (2:3, v/v (5 mL)) and stirred, and PdCl$_2$(PPh$_3$)$_2$ (7 mg, 0.01 mmol) and CuI (3.8 mg, 0.02 mmol) were added to the resulting solution. The solution was purged with argon for 15 minutes, sealed and heated at 85 to 90° C. for 18 hours. The solvent was evaporated under reduced pressure, and H$_2$O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na$_2$SO$_4$ and then filtered. The solvent was evaporated under reduced pressure, and the resulting residue was purified by flash column chromatography on silica gel using dichloromethane containing 2 to 5% methanol and 1% ammonia water (NH$_4$OH) to obtain the title compound as a pure beige solid: 25.6 mg (yield 24.7%); $^1$H NMR (400 MHz, acetone-d$_6$) δ 11.04 (br. s, 1H), 9.85 (s, 1H), 8.32-8.28 (m, 2H), 8.16 (s, 1H), 7.92 (d, J=8.0 Hz, 1H), 7.61 (d, J=8.4 Hz, 1H), 7.47 (t, J=7.9 Hz, 1H), 7.43-7.40 (m, 2H), 7.31 (t, J=8.4 Hz, 1H), 7.20 (d, J=7.0 Hz, 1H), 4.98 (br. s, 2H), 3.06 (t, J=4.7 Hz, 4H), 2.57 (s, 4H), 2.31 (s, 3H); $^{13}$C NMR (100 MHz, acetone-d$_6$) δ 164.07, 155.49, 149.06, 142.00, 139.63, 132.44, 130.59, 129.15, 127.06, 127.01, 126.83, 126.36, 123.59, 123.13, 123.02, 122.80, 120.76, 114.61, 113.00, 110.79, 92.92, 87.03, 55.09, 53.04, 45.41; HRMS (ESI-TOF) m/z calculated for C$_{28}$H$_{26}$F$_3$N$_6$O [M+H]$^+$: 519.2120, found: 519.2134.

Example 4-8: Preparation of N-(3-((3-amino-1H-indazol-4-yl)ethynyl)phenyl)-3,5-bis(trifluoromethyl)benzamide (Compound 8)

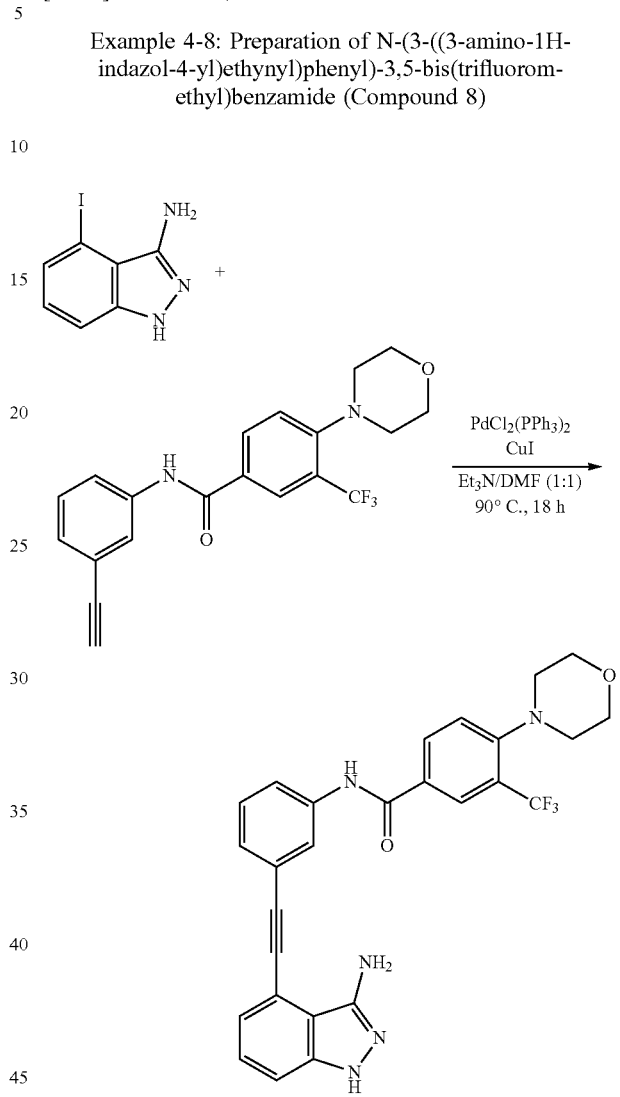

A solution of Compound 36 (56 mg, 0.216 mmol) and N-(3-ethynylphenyl)-4-morpholino-3-(trifluoromethyl)benzamide (97 mg, 0.259 mmol) was added to DMF/Et$_3$N (2:3, v/v (5 mL)) and stirred, and PdCl$_2$(PPh$_3$)$_2$ (7.5 mg, 0.0108 mmol) and CuI (4.1 mg, 0.0216 mmol) were added to the resulting solution. The solution was purged with argon for 15 minutes, sealed and heated at 85 to 90° C. for 18 hours. The solvent was evaporated under reduced pressure, and H$_2$O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na$_2$SO$_4$ and then filtered. The solvent was evaporated under reduced pressure, and the resulting residue was purified by flash column chromatography on silica gel using ethyl acetate-hexane (2:1, v/v) and then 100% ethyl acetate to obtain the title compound as a pure beige solid: 74 mg (yield 67.8%); $^1$H NMR (400 MHz, DMSO) δ 11.82 (s, 1H), 10.52 (s, 1H), 8.29-8.26 (m, 2H), 8.06 (s, 1H), 7.86 (d, J=7.6 Hz, 1H), 7.66 (d, J=8.0 Hz, 1H), 7.47 (t, J=7.6 Hz, 1H), 7.40-7.34 (m, 2H), 7.28 (t, J=8.0 Hz, 1H), 7.16 (d, J=7.2 Hz, 1H), 5.16 (s, 2H), 3.74 (s, 4H), 2.98 (s, 4H); $^{13}$C NMR (100 MHz, DMSO) δ 164.50, 155.03, 149.05, 141.74, 139.80, 133.47, 130.80, 129.78, 127.50 (q, J=6 Hz), 127.24, 126.83, 124.91, 124.63, 124.33, 123.24, 123.02, 122.73, 121.59, 114.29, 112.72, 111.52, 93.37, 87.56; HRMS (ESI-TOF) m/z calculated for $C_{27}H_{23}F_3N_5O_2$ [M+H]$^+$: 506.1804, found: 506.1807.

Example 4-9: Preparation of 3-((3-amino-1H-indazol-4-yl)ethynyl)-N-(3-(trifluoromethyl)phenyl)benzamide (Compound 9)

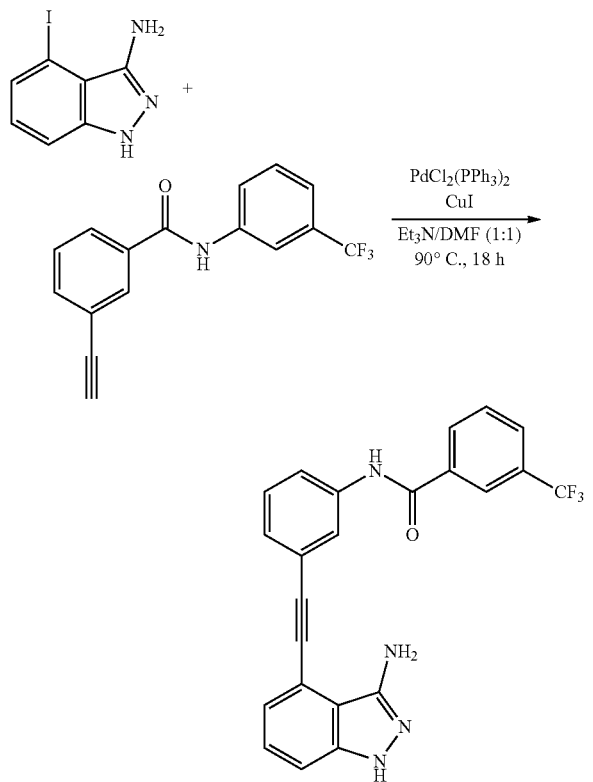

J=8.4 Hz, 1H), 7.33 (t, J=8.0 Hz, 1H), 7.23 (d, J=6.8 Hz, 1H), 5.01 (s, 2H); $^{13}$C NMR (100 MHz, acetone-d$_6$) δ 164.99, 140.08, 135.46, 134.47, 130.61, 130.27, 129.74, 129.07, 128.00, 126.42, 123.54, 123.27, 123.18, 120.21, 116.58, 116.54, 111.10, 92.14, 87.98.

Example 4-10: Preparation of 3-((3-amino-1H-indazol-4-yl)ethynyl)-N-(3,5-bis (trifluoromethyl)phenyl)benzamide (Compound 10)

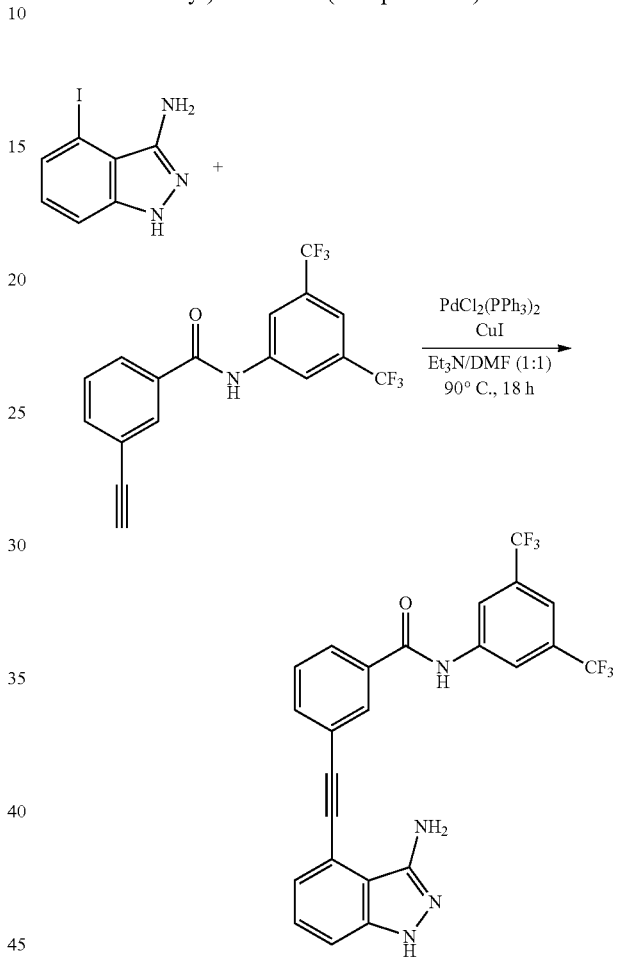

A solution of Compound 36 (60 mg, 0.232 mmol) and 3-ethynyl-N-(3-(trifluoromethyl)phenyl)benzamide (67 mg, 0.232 mmol) was added to DMF/Et$_3$N (1:1, v/v (4 mL)) and stirred, and PdCl$_2$(PPh$_3$)$_2$ (3.2 mg, 0.0046 mmol) and CuI (1.7 mg, 0.0092 mmol) were added to the resulting solution. The solution was purged with argon for 15 minutes, sealed and heated at 85 to 90° C. for 18 hours. The solvent was evaporated under reduced pressure, and H$_2$O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na$_2$SO$_4$ and then filtered. The solvent was evaporated under reduced pressure, and the resulting residue was purified by flash column chromatography on silica gel using ethyl acetate-hexane (1:1, v/v) and then ethyl acetate-hexane (2:1, v/v) to obtain the title compound as a pure gray solid: 42.5 mg (yield 43.7%); $^1$H NMR (400 MHz, acetone-d$_6$) δ 11.09 (br. s, 1H), 9.98 (s, 1H), 8.36 (s, 1H), 8.28 (s, 1H), 8.14 (d, J=8.0 Hz, 1H), 8.09 (d, J=7.6 Hz, 1H), 7.87 (d, J=7.6 Hz, 1H), 7.66-7.61 (m, 2H), 7.49 (d, J=7.6 Hz, 1H), 7.42 (d, A solution of Compound 36 (41.6 mg, 0.161 mmol) and N-(3,5-bis (trifluoromethyl)phenyl)-3-ethynylbenzamide (57.5 mg, 0.161 mmol) was added to DMF/Et$_3$N (1:1, v/v (4 mL)) and stirred, and PdCl$_2$(PPh$_3$)$_2$ (2.2 mg, 0.0032 mmol) and CuI (1.2 mg, 0.0064 mmol) were added to the resulting solution. The solution was purged with argon for 15 minutes, sealed and heated at 85 to 90° C. for 18 hours. The solvent was evaporated under reduced pressure, and H$_2$O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na$_2$SO$_4$ and then filtered. The solvent was evaporated under reduced pressure, and the resulting residue was purified by flash column chromatography on silica gel using ethyl acetate-hexane (1:1, v/v) to obtain the title compound as a pure solid: 10.1 mg (yield 12.8%); $^1$H NMR (400 MHz, acetone-d$_6$) δ 11.12 (br. s, 1H), 10.27 (s, 1H), 8.61 (s, 1H), 8.32 (s, 1H), 8.12 (d, J=8.0 Hz, 1H), 7.88 (d, J=7.6 Hz, 1H), 7.79 (s, 1H), 7.64 (t, J=8.0 Hz, 1H), 7.43 (d, J=8.4 Hz, 1H), 7.32 (t, J=8.4 Hz, 1H), 7.22 (d, J=7.2 Hz, 1H), 5.03 (s, 2H); $^{13}$C NMR (100 MHz, acetone-d$_6$) δ 165.34, 149.07, 142.02, 141.18, 134.84, 134.81, 131.62 (q, J=33 Hz), 130.33, 129.15, 128.07, 126.41, 124.90, 123.28, 122.20, 120.01 (q, J=4 Hz), 116.65 (q, J=4 Hz), 114.28, 112.96, 111.11, 92.05, 88.13.

Example 4-11: Preparation of 3-((3-amino-1H-indazol-4-yl)ethynyl)-N-(3-(4-methyl-1H-imidazol-1-yl)-5-(trifluoromethyl)phenyl) benzamide (Compound 11)

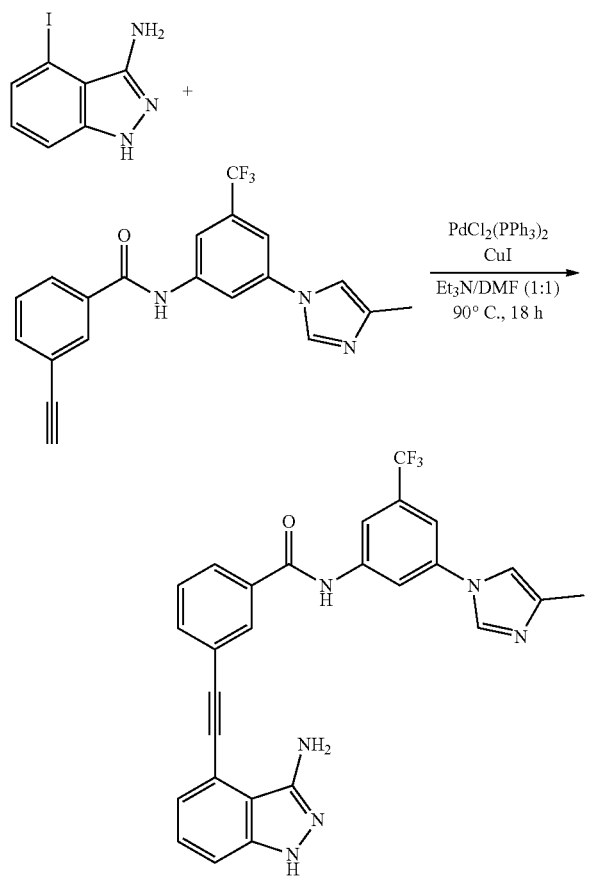

A solution of Compound 36 (52.5 mg, 0.203 mmol) and 3-ethynyl-N-(3-(4-methyl-1H-imidazol-1-yl)-5-(trifluoromethyl)phenyl)benzamide (75 mg, 0.203 mmol) was added to DMF/Et$_3$N (1:1, v/v (4 mL)) and stirred, and PdCl$_2$(PPh$_3$)$_2$ (2.8 mg, 0.004 mmol) and CuI (1.5 mg, 0.008 mmol) were added to the resulting solution. The solution was purged with argon for 15 minutes, sealed, and heated at 85 to 90° C. for 18 hours. The solvent was evaporated under reduced pressure, and H$_2$O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na$_2$SO$_4$, and then filtered. The solvent was evaporated under reduced pressure, and the resulting residue was purified by flash column chromatography on silica gel (Kanto Chemical) using dichloromethane containing 5% methanol to obtain the title compound as a pure solid: 11.1 mg (yield 11%); $^1$H NMR (400 MHz, acetone-d$_6$) δ 11.08 (br. s, 1H), 10.16 (s, 1H), 8.30 (s, 1H), 8.25 (s, 1H), 8.12 (s, 1H), 8.10 (s, 1H), 7.89 (d, J=7.6 Hz, 1H), 7.70-7.65 (m, 2H), 7.44-7.41 (m, 2H), 7.33 (t, J=8.4 Hz, 1H), 7.23 (d, J=6.8 Hz, 1H), 4.98 (s, 2H), 2.24 (s, 3H); $^{13}$C NMR (100 MHz, acetone-d$_6$) δ 165.18, 165.11, 148.94, 141.51, 141.42, 139.83, 138.68, 135.09 (q, J=4 Hz), 134.70, 131.94 (q, J=33 Hz), 130.27, 129.18, 128.03, 126.35, 123.29, 123.22, 122.49, 114.97, 114.88, 114.33, 114.09, 112.97, 112.04 (q, J=4 Hz), 111.07, 92.01, 88.11; HRMS (ESI-TOF) m/z calculated for C$_{27}$H$_{20}$F$_3$N$_6$O [M+H]$^+$: 501.1651, found: 501.1650.

Example 4-12: Preparation of 3-((3-amino-1H-indazol-4-yl)ethynyl)-N-(3-((4-methylpiperazin-1-yl)methyl)-5-(trifluoromethyl)phenyl)benzamide (Compound

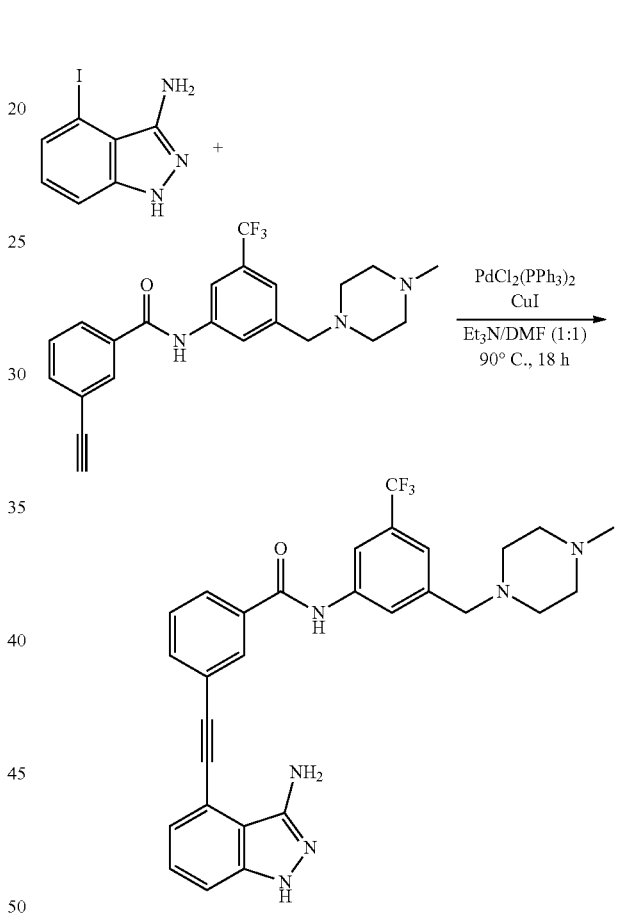

A solution of Compound 36 (35.3 mg, 0.137 mmol) and 3-ethynyl-N-(3-((4-methylpiperazin-1-yl)methyl)-5-(trifluoromethyl)phenyl)benzamide (65.8 mg, 0.164 mmol) was added to DMF/Et$_3$N (2:3, v/v (5 mL)) and stirred, and PdCl$_2$(PPh$_3$)$_2$ (4.9 mg, 0.0068 mmol) and CuI (2.5 mg, 0.0137 mmol) were added to the resulting solution. The solution was purged with argon for 15 minutes, sealed and heated at 85 to 90° C. for 18 hours. The solvent was evaporated under reduced pressure, and H$_2$O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na$_2$SO$_4$ and then filtered. The solvent was evaporated under reduced pressure, and the resulting residue was purified by flash column chromatography on silica gel using dichloromethane containing 1-5% methanol and 1% NH₄OH to obtain the title compound as a pure solid: 11.4 mg (yield 15.6%); ¹H NMR (400 MHz, acetone-d₆) δ 11.06 (br. s, 1H), 9.94 (s, 1H), 8.29-8.27 (m, 2H), 8.11-8.08 (m, 2H), 7.88 (d, J=7.6 Hz, 1H), 7.65 (t, J=8.0, 1H), 7.44 (s, 1H), 7.42 (s, 1H), 7.33 (t, J=8.4, 1H), 7.23 (d, J=6.8, 1H), 4.96 (d, J=10.0 Hz, 1H), 3.61 (s, 2H), 2.49-2.40 (m, 8H), 2.21 (s, 3H); ¹³C NMR (100 MHz, acetone-d₆) δ 164.93, 141.44, 140.05, 139.96, 135.48 (q, J=31 Hz), 134.44, 131.38, 130.48, 130.28, 130.16, 129.24, 129.07, 129.00, 128.00, 126.35, 125.80, 123.68, 123.60, 123.20, 120.38, 115.20 (q, J=4 Hz), 114.31, 111.03, 92.11, 87.98; HRMS (ESI-TOF) m/z calculated for C₂₉H₂₈F₃N₆O [M+H]⁺: 533.2277, found: 533.2277.

Example 4-13: Preparation of 3-((3-amino-1H-indazol-4-yl)ethynyl)-N-(3-((4-methylpiperazin-1-yl)methyl)-5-(trifluoromethyl)phenyl) benzamide (Compound 13)

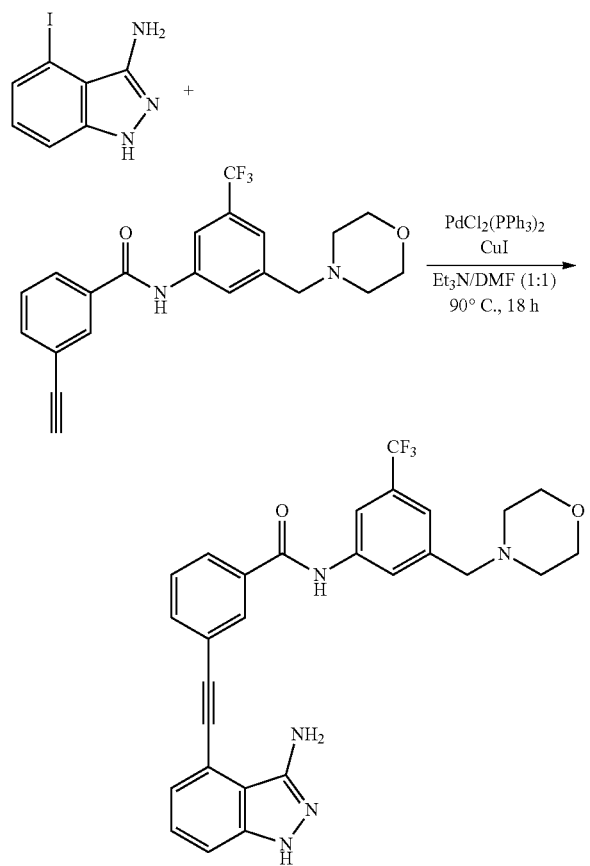

A solution of Compound 36 (58.6 mg, 0.226 mmol) and 3-ethynyl-N-(3-(morpholinomethyl)-5-(trifluoromethyl)phenyl)benzamide (105.5 mg, 0.272 mmol) was added to DMF/Et₃N (2:3, v/v (5 mL)) and stirred, and PdCl₂(PPh₃)₂ (7.9 mg, 0.0113 mmol) and CuI (4.3 mg, 0.0226 mmol) were added to the resulting solution. The solution was purged with argon for 15 minutes, sealed and heated at 85 to 90° C. for 18 hours. The solvent was evaporated under reduced pressure, and H₂O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na₂SO₄ and then filtered. The solvent was evaporated under reduced pressure and the resulting residue was purified by flash column chromatography on silica gel (Kanto Chemical) using dichloromethane containing 2-5% methanol to obtain the title compound as a pure solid: 48.1 mg (yield 41%); ¹H NMR (400 MHz, acetone-d₆) δ 11.10 (br. s, 1H), 9.97 (s, 1H), 8.30 (s, 1H), 8.11-8.09 (m, 2H), 7.87-7.85 (m, 1H), 7.66-7.60 (m, 1H), 7.44 (d, J=6.8 Hz, 1H), 7.42 (s, 1H), 7.32 (dt, J=8.0 Hz, 1.2 Hz, 1H), 7.22 (d, J=6.4, 1H), 5.01 (br. s, 2H), 3.66-3.64 (m, 4H); ¹³C NMR (100 MHz, acetone-d₆) δ 164.98, 149.08, 142.01, 140.37, 140.06, 135.44, 134.46, 130.36 (q, J=32 Hz), 130.29, 129.06, 128.01, 126.40, 125.78, 123.84, 123.24, 123.18, 123.08, 120.50 (q, J=4 Hz), 115.40, 114.34, 111.07, 92.17, 87.99, 66.54, 62.34, 53.54; HRMS (ESI-TOF) m/z calculated for C₂₈H₂₅F₃N₅O₂ [M+H]⁺: 520.1960, found: 520.1960.

Example 4-14: Preparation of 3-((3-amino-1H-indazol-4-yl)ethynyl)-N-(4-chloro-3-(trifluoromethyl)phenyl)benzamide (Compound 14)

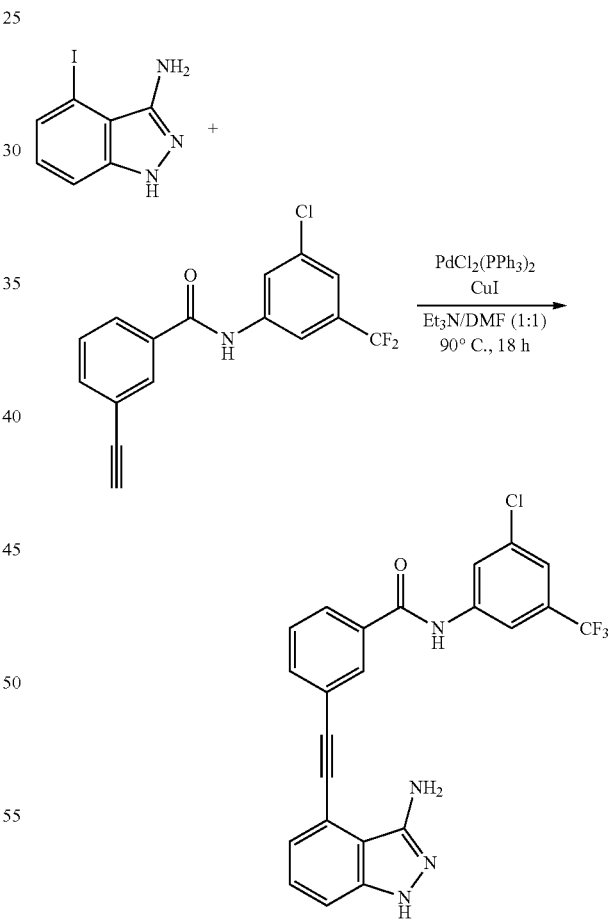

A solution of Compound 36 (38 mg, 0.146 mmol) and N-(4-chloro-3-(trifluoromethyl)phenyl)-3-ethynylbenzamide (57 mg, 0.175 mmol) was added to DMF/Et₃N (2:3, v/v (5 mL)) and stirred, and PdCl₂(PPh₃)₂ (5.1 mg, 0.0073 mmol) and CuI (2.7 mg, 0.0146 mmol) were added to the resulting solution. The solution was purged with argon for 15 minutes, sealed and heated at 85 to 90° C. for 18 hours.

The solvent was evaporated under reduced pressure, and H₂O and ethyl acetate (10 mL each) were added to the residue. The organic layer was separated and the aqueous layer was extracted repeatedly with ethyl acetate (3×10 mL). The combined organic layer was washed with brine solution, dried with anhydrous Na₂SO₄ and then filtered. The solvent was evaporated under reduced pressure, and the resulting residue was purified by flash column chromatography on silica gel using ethyl acetate-hexane (1:1, v/v) and 100% ethyl acetate to obtain the title compound as a pure solid: 50.6 mg (yield 76.2%); ¹H NMR (400 MHz, acetone-d₆) δ 11.05 (br. s, 1H), 10.05 (s, 1H), 8.44 (d, J=2.0 Hz, 1H), 8.27 (s, 1H), 8.20 (dd, J=8.4 Hz, 2.0 Hz, 1H), 8.08 (d, J=7.6 Hz, 1H), 7.88 (d, J=7.6 Hz, 1H), 7.69-7.65 (m, 2H), 7.43 (d, J=8.4 Hz, 1H), 7.33 (t, J=8.4 Hz, 1H), 7.23 (d, J=7.2 Hz, 1H), 4.96 (s, 1H); ¹³C NMR (100 MHz, acetone-d₆) δ 165.02, 149.02, 141.97, 138.70, 135.18, 134.60, 131.99, 130.27, 129.11, 128.00, 127.87, 126.37, 125.36, 124.88, 124.67, 124.40, 123.24, 119.08 (q, J=6 Hz), 114.28, 112.96, 111.06, 92.05, 88.06.

were added to the residue. The organic layer was separated and the aqueous layer was extracted repeatedly with ethyl acetate (3×10 mL). The combined organic layer was washed with brine solution, dried with anhydrous Na₂SO₄ and then filtered. The solvent was evaporated under reduced pressure, and the resulting residue was purified by flash column chromatography on silica gel using ethyl acetate containing 0-20% methanol to obtain the title compound as a pure green solid: 25.6 mg (yield 23%); ¹H NMR (400 MHz, CDCl₃) δ 10.21 (br. s, 1H), 8.93 (s, 1H), 7.97 (s, 1H), 7.91 (s, 1H), 7.86 (d, J=8.4 Hz, 1H), 7.79 (t, J=7.6 Hz, 1H), 7.67 (d, J=8.0 Hz, 1H), 7.55 (d, J=7.2 Hz, 1H), 7.32-7.29 (m, 1H), 7.14-7.07 (m, 3H), 4.79 (br. s, 2H), 3.58 (s, 2H), 2.51-2.41 (m, 10H), 1.11-1.08 (m, 4H); ¹³C NMR (100 MHz, CDCl₃) δ 165.52, 148.99, 141.76, 136.63, 134.81, 134.49, 133.71, 131.25, 129.92, 128.90, 127.62, 127.23, 125.39, 124.10, 123.58, 123.06, 122.67, 117.88, 114.50, 113.12, 110.85, 92.62, 87.88, 57.78, 52.92, 52.79, 52.26, 11.84; HRMS (ESI-TOF) m/z calculated for C₃₀H₃₀F₃N₆O [M+H]⁺: 547.2433, found: 547.2438.

Example 4-15: Preparation of 3-((3-amino-1H-indazol-4-yl)ethynyl)-N-(4-((4-ethylpiperazin-1-yl)methyl)-3-(trifluoromethyl)phenyl)benzamide (Compound 15)

Example 4-16: Preparation of 3-((3-amino-1H-indazol-4-yl)ethynyl)-N-(4-(morpholinomethyl)-3-(trifluoromethyl)phenyl)benzamide (Compound 16)

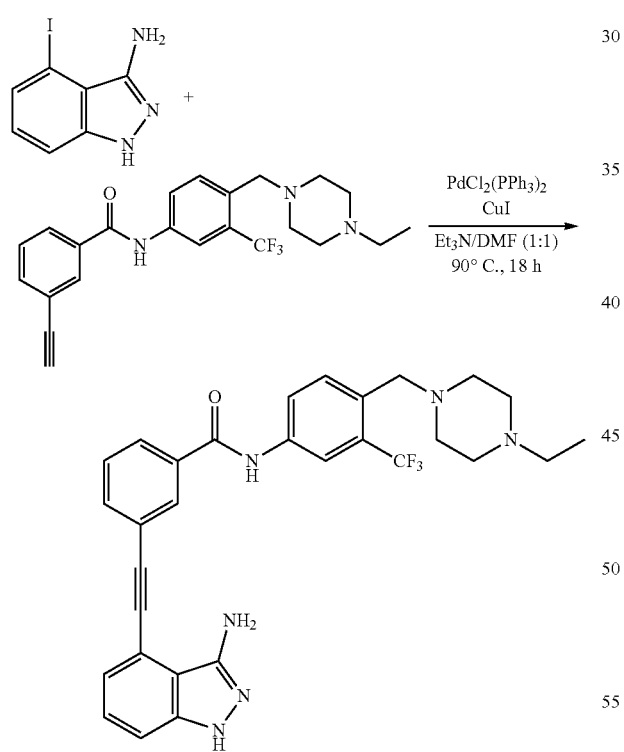

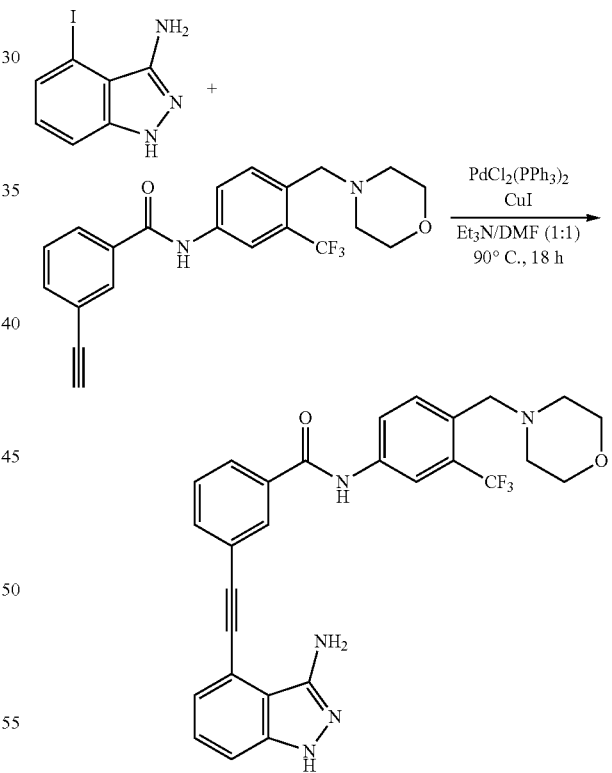

A solution of Compound 36 (53 mg, 0.205 mmol) and N-(4-((4-ethylpiperazin-1-yl)methyl)-3-(trifluoromethyl)phenyl)-3-ethynylbenzamide (85 mg, 0.205 mmol) was added to DMF/Et₃N (1:1, v/v (4 mL)) and stirred, and PdCl₂(PPh₃)₂ (3 mg, 0.004 mmol) and CuI (2 mg, 0.008 mmol) were added to the resulting solution. The solution was purged with argon for 15 minutes, sealed and heated at 85 to 90° C. for 18 hours. The solvent was evaporated under reduced pressure, and H₂O and ethyl acetate (10 mL each)

A solution of Compound 36 (45 mg, 0.174 mmol) and 3-ethynyl-N-(4-(morpholinomethyl)-3-(trifluoromethyl)phenyl)benzamide (81 mg, 0.209 mmol) was added to DMF/Et₃N (2:3, v/v (5 mL)) and stirred, and PdCl₂(PPh₃)₂ (6 mg, 0.0086 mmol) and CuI (3.2 mg, 0.0172 mmol) were added to the resulting solution. The solution was purged with argon for 15 minutes, sealed, and heated at 85 to 90° C. for 18 hours. The solvent was evaporated under reduced pressure, and H₂O and ethyl acetate (10 mL each) were added to the residue. The organic layer was separated and the aqueous layer was extracted repeatedly with ethyl acetate (3×10 mL). The combined organic layer was washed with brine solution, dried with anhydrous $Na_2SO_4$ and then filtered. The solvent was evaporated under reduced pressure and the resulting residue was purified by flash column chromatography on silica gel (Kanto Chemical) using ethyl acetate containing 0-20% methanol to obtain the title compound as a pure solid: 57.2 mg (yield 63.4%); $^1H$ NMR (400 MHz, DMSO) δ 11.84 (s, 1H), 10.66 (s, 1H), 8.24 (s, 1H), 8.08 (d, J=8.4 Hz, 1H), 8.03 (d, J=8.0 Hz, 1H), 7.87 (d, J=7.6 Hz, 1H), 7.75 (d, J=8.4 Hz, 1H), 7.65 (t, J=7.6 Hz, 1H), 7.37 (d, J=8.4 Hz, 1H), 7.30 (t, J=8.4 Hz, 1H), 7.19 (d, J=6.8 Hz, 1H), 5.16 (s, 2H), 3.60-3.59 (m, 6H), 2.40 (s, 4H); $^{13}C$ NMR (100 MHz, DMSO) δ 165.39, 149.06, 141.77, 138.65, 135.50, 134.94, 132.20, 131.88, 130.75, 129.63, 128.78, 128.02 (q, J=33 Hz), 126.81, 126.15, 123.99, 123.38, 122.80, 117.79 (q, J=6 Hz), 114.10, 112.75, 111.70, 92.72, 88.51, 66.70, 58.34, 53.76; HRMS (ESI-TOF) m/z calculated for $C_{28}H_{25}F_3N_5O_2$ $[M+H]^+$: 520.1960, found: 520.1955.

Experimental Example

The protein kinase activity inhibition of the compounds of Compound Nos. 1 to 16 synthesized in Examples of the present invention was verified in the following Experimental Example 1, and the anticancer activity thereof against cancer cells was determined in Experimental Example 2.

Experimental Example 1: Verification of Inhibitory Effect on Kinase Activity (ABL-1 and $ABL^{T315I}$)

The kinase inhibitory effect of the compounds of Compound Nos. 1 to 16 was measured. Kinase analysis was conducted in a "Hot Spot" analysis platform manner. Specific kinase/substrate pairs and cofactors were prepared in a reaction buffer (20 mM HEPES (pH 7.5), 10 mM $MgCl_2$, 1 mM EGTA, 0.02% Brij35, 0.02 mg/ml BSA, 0.1 mM $Na_3VO_4$, 2 mM DTT and 1% DMSO). 10 concentrations of compounds that were serially diluted 3 times in sequence from a concentration of 20 μM were added to the reaction mixture, and a mixture of ATP (10 μM, Sigma) and 33P ATP (Perkin Elmer) was added thereto after 20 minutes. The reaction was conducted at 25° C. for 120 minutes, the spots during the reaction were filtered using P81 ion exchange filter paper (Whatman #3698-915), and the unbound phosphate was removed by washing with 0.1% phosphoric acid using a filter.

The following Table 1 shows the inhibitory activity of kinase quantified depending on the concentration of each experimental compound that was added based on 100% of the kinase activity of the negative control group (kinase treated only with DMSO, not treated with the compound).

Meanwhile, kinase inhibitory activity against ABL and T315I mutations of imatinib (*Bioorg. Med. Chem. Lett.* 2012, 22, 5279), nilotinib (*Brit. J. Cancer,* 2006, 94, 1765), ponatinib (*Cancer Cell.* 2009, 16, 401.) and 1H-indazol-3-amine (*Eur. J. Med. Chem.* 2015, 104, 139) as positive control groups were determined according to values in the respective references. In addition, the activity of imatinib and ponatinib against DDR1 (*J. Mol. Biol.* 2014, 426, 2457) and the activity of nilotinib (*Eur. J. Pharm.* 2008, 599, 44) was determined with reference to published papers.

TABLE 1

| Experimental compound | $IC_{50}$, nM | | |
|---|---|---|---|
| | $ABL^{wild}$ | $ABL^{T315I}$ | DDR1 |
| Compound No. 1 | 313 | 2550 | 53.3 |
| Compound No. 2 | 667 | $ND^b$ | 96.5 |
| Compound No. 3 | 17.1 | 1290 | 13.1 |
| Compound No. 4 | 172 | $ND^a$ | 82.8 |
| Compound No. 5 | 637 | $ND^a$ | 20.1 |
| Compound No. 6 | 104 | 2960 | 22.6 |
| Compound No. 7 | 151 | $ND^a$ | 31.9 |
| Compound No. 8 | 5.21 | 183 | 14.7 |
| Compound No. 9 | 210 | $ND^a$ | 18.4 |
| Compound No. 10 | 186 | $ND^a$ | 33.0 |
| Compound No. 11 | 15.4 | 1060 | 21.0 |
| Compound No. 12 | 60.5 | 1150 | 29.1 |
| Compound No. 13 | 571 | 2510 | 25.3 |
| Compound No. 14 | 255 | $ND^a$ | 20.0 |
| Compound No. 15 | 0.625 | 5.82 | 3.70 |
| Compound No. 16 | 103 | 1360 | 16.3 |
| Imatinib | 217 | — | 337 |
| Nilotinib | 20 | — | 43 |
| Ponatinib | 0.37 | 2.0 | 9.4 |
| (4-(4-(3-amino-1H-indazol-4-yl)benzoyl)piperazin-1-yl)(2,4-dichlorophenyl)methanone | 14 | 450 | $ND^a$ |

$^a$Not determined.

As shown in Table 1 above, the compounds of Compound Nos. 1 to 16 exhibited inhibitory activity against ABL and DDR1. Specifically, the compounds of Compound Nos. 8 and 15 showed excellent inhibitory activity against ABL and DDR1 exhibited $IC_{50}$ for ABL of 5.21 nM and 0.625 nM, respectively, and $IC_{50}$ for DDR1 of 14.7 nM and 3.70 nM, respectively. In addition, Compound Nos. 8 and 15 exhibited inhibitory activity against the T315I point mutation of ABL, as well as ABL and DDR1, and exhibited $IC_{50}$ of 183 nM and 5.82 nM, respectively. In particular, Compound No. 15 exhibited excellent inhibitory activity against a T315I point mutation of ABL as well as ABL and DDR1.

Experimental Example 2: Verification of Anticancer Effect of Inhibitor Against Human Leukemia Cancer Cell (K-562)

The cell line used for an MTT assay was K-562 (human leukemia cancer), and was obtained from the Korea Cell Line Bank and then cultured. The medium herein used was RPMI 1640 medium containing 10% fetal bovine serum, and the culture was conducted in a constant-temperature constant-humidity incubator (37° C., 5% $CO_2$). The cells were seeded at a density of $3\times10^3$ cells/well in a 96-well microplate and cultured in a $CO_2$ incubator for 24 hours, the medium was removed, and further culture was performed for 72 hours in 100 μl of respective inhibitor solutions diluted to different concentrations. 15 μl of an MTT solution (Promega, CellTiter 96) was added thereto and cultured for 4 hours. Then, blue formazan, formed by adding 100 μl of a stop solution (Promega, CellTiter 96), was dissolved.

After the culture solution was allowed to stand for 18 hours or more, absorbance was measured at 570 nm to obtain $IC_{50}$ (a concentration at which 50% of cancer cells are inhibited). 72 hours after treatment or non-treatment with different concentrations of the compounds Nos. 1 to 16 synthesized in Examples above, the anti-proliferative effect of each compound on K562 cells was measured as $GI_{50}$, and the result for each compound added was shown in Table 2 below.

The following Table 2 shows the anticancer activity of target indazoles, quantified depending on the concentration of each experimental compound that was added, based on 100% of the cancer cell activity of the negative control group (treated with only DMSO, not-treated with the compound).

Meanwhile, the antiproliferative activity against K562 of imatinib (*Oncotarget* 2016, 7, 45562), nilotinib (*Proc. Am. Assoc. Cancer. Res.* 2005, 46, 5987) and (4-(4-(3-amino-1H-indazol-4-yl)benzoyl)piperazin-1-yl)(2,4-dichlorophenyl)methanone (*Eur. J. Med. Chem.* 2015, 104, 139.) as positive control groups were determined according to values in the references.

TABLE 2

| Experimental compound | $GI_{50}$, μm K562 |
|---|---|
| Compound No. 1 | 1.45 ± 1.16 |
| Compound No. 2 | 40.71 ± 7.15 |
| | ($GI_{50}$ at concentration of 10 μM) |
| Compound No. 3 | 0.12 ± 1.29 |
| Compound No. 4 | 2.10 ± 1.11 |
| Compound No. 5 | 2.14 ± 1.15 |
| Compound No. 6 | 1.62 ± 1.24 |
| Compound No. 7 | ND$^a$ |
| Compound No. 8 | 0.02 ± 1.33 |
| Compound No. 9 | 3.75 ± 1.22 |
| Compound No. 10 | 0.46 ± 1.34 |
| Compound No. 11 | 0.14 ± 1.28 |
| Compound No. 12 | 0.29 ± 1.19 |
| Compound No. 13 | 0.74 ± 1.27 |
| Compound No. 14 | 3.33 ± 1.18 |
| Compound No. 15 | 0.03 ± 1.39 |
| Compound No. 16 | 0.52 ± 1.25 |
| Imatinib | 0.267 ± 0.03 |
| Nilotinib | 0.08 ± 0.09 |
| (4-(4-(3-amino-1H-indazol-4-yl)benzoyl)piperazin-1-yl)(2,4-dichlorophenyl)methanone | 6.50 |

$^a$Not determined.

As shown in Table 2 above, Compound Nos. 1, 3 to 6, and 8 to 16, excluding the compounds of Compound Nos. 2 and 7, exhibited an excellent proliferation inhibitory effect on K-562 cancer cells.

Specifically, the $GI_{50}$ values of Compound Nos. 8 and 15, exhibiting excellent anti-proliferative activity against K-562 cancer cells, were 0.02 μM and 0.03 μM, which correspond to 13- and 8.9-fold higher inhibitory effects than imatinib used as a positive control group, respectively, and 4- and 2.7-fold higher inhibitory effects than nilotinib, respectively.

Preparation Example

Meanwhile, the novel compound represented by Formula 1 according to the present invention can be formulated in various forms according to the purpose. Examples of some formulation methods including incorporation of the compound represented by Formula 1 according to the present invention as an active ingredient are as follows, but the present invention is not limited thereto.

Formulation Example 1: Tablet (Direct Pressurization)

5.0 mg of the active ingredient was sieved and 14.1 mg of lactose, 0.8 mg of crospovidone USNF and 0.1 mg of magnesium stearate were mixed and pressurized into tablets.

Formulation Example 2: Tablet (Wet Granulation)

5.0 mg of the active ingredient was sieved and was mixed with 16.0 mg of lactose and 4.0 mg of starch. 800.3 mg of Polysorbate 80 was dissolved in pure water, and an appropriate amount of the resulting solution was added to the resulting mixture, followed by granulation. The granules were dried, sieved and mixed with 2.7 mg of colloidal silicon dioxide and 2.0 mg of magnesium stearate. The granules were pressed into tablets.

Formulation Example 3. Powders and Capsules 5.0 mg of the active ingredient was sieved and then mixed with 14.8 mg of lactose, 10.0 mg of polyvinylpyrrolidone and 0.2 mg of magnesium stearate. Hard No. 5 gelatin capsules were filled with the resulting mixture.

Formulation Example 4. Injection

Injections were prepared by incorporating 100 mg of the active ingredient as well as 180 mg of mannitol, 26 mg of $Na_2HPO_4.12H_2O$ and 2,974 mg of distilled water.

The novel indazole derived compound according to the present invention has excellent ability to inhibit the activity of ABL protein kinase, T315I mutant ABL protein kinase and DDR1 protein kinase. Therefore, the novel indazole derived compound can be used for the purpose of treating, preventing and alleviating cancer caused by abnormal cell growth.

The pharmaceutical composition for preventing, alleviating or treating cancer including a compound selected from an indazole derived compound according to the present invention, a pharmaceutically acceptable salt thereof, a hydrate thereof and a stereoisomer thereof as an active ingredient, exhibits high inhibitory activity and a high anti-proliferative effect selective for cancer cells, and exhibits low cytotoxicity, thus being useful for the prevention or treatment of cancer.

The kinds of cancer that can be treated, prevented or alleviated by treatment with the compound according to the present invention include blood cancer, lung cancer, breast cancer, stomach cancer, liver cancer, colon cancer, skin cancer, uterine cancer, brain cancer, laryngeal cancer, prostate cancer, bladder cancer, esophageal cancer, thyroid cancer, kidney cancer, rectal cancer and the like.

In particular, the compound according to the present invention exhibits excellent inhibitory activity against T315I mutant ABL protein kinase as well as ABL protein kinase and DDR1 protein kinase, and thus can be used for the prevention, alleviation or treatment of blood cancer, especially chronic myelogenous leukemia (CML).

Although embodiments of the present invention have been described above, it will be obvious to those skilled in the art that the present invention can be implemented in other specific embodiments without changing technical concepts or essential features of the present invention. Therefore, it should be construed that the aforementioned embodiments are illustrative and not restrictive in all respects.

What is claimed is:
1. A compound selected from an indazole-derived compound represented by the following Formula 1, a pharmaceutically acceptable salt thereof, a hydrate thereof and a stereoisomer thereof:

[Formula 1]

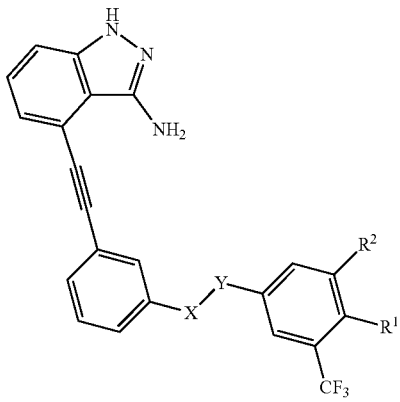

wherein $R^1$ and $R^2$ each independently represent hydrogen; a halogen atom; a $C_1$-$C_{13}$ alkyl group; a $C_3$-$C_{10}$ aryl group; a $C_3$-$C_{10}$ cyclic group; a $C_3$-$C_{10}$ heteroaryl group; and a $C_3$-$C_{10}$ heterocyclic group;

X and Y are each independently —NH—; or —C(O)—; and wherein the $C_1$-$C_{13}$ alkyl group or the $C_3$-$C_{10}$ cyclic group contains at least one substituent selected from the group consisting of hydrogen; a hydroxy group; a halogen group; a $C_1$-$C_{13}$ alkyl group; a $C_1$-$C_6$ alkoxy group; an amino group (—NR$_3$R$_4$); a nitro group (—N(O)$_2$); an amide group (—(C═O)NR$_3$R$_4$); a carboxyl group (—C(O)OH); a nitrile group (—CN); a urea group (—NR$_3$(C═O)NR$_4$—); a sulfonamide group (—NHS(O)$_2$—); a sulfide group (—S—); a sulfone group (—S(O)$_2$—); a phosphinyl group (—P(O)R$_3$R$_4$); a $C_6$-$C_{10}$ aryl group; a $C_3$-$C_{10}$ heteroaryl group; and a $C_3$-$C_{10}$ heterocyclic group, the $C_3$-$C_{10}$ aryl group, the $C_3$-$C_{10}$ heteroaryl group or the $C_3$-$C_{10}$ heterocyclic group contains at least one substituent selected from the group consisting of hydrogen; a hydroxy group; a halogen group; a carbonyl group (—(C═O)R$_3$R$_4$); a $C_1$-$C_3$ alkyl group substituted or unsubstituted with halogen or a $C_3$-$C_{10}$ heterocyclic group; a $C_1$-$C_3$ alkoxy group substituted or unsubstituted with halogen or a $C_3$-$C_{10}$ heterocyclic group; $C_6$-$C_{10}$ phenoxy; an amino group (—NR$_3$R$_4$); a nitro group (—N(O)$_2$); an amide group (—(C═O)NR$_3$R$_4$); a carboxyl group (—C(O)OH); a nitrile group (—CN); a urea group (—NR$_3$(C═O)NR$_4$—); a sulfonamide group (—NHS(O)$_2$—); a sulfide group (—S—); a sulfone group (—S(O)$_2$—); a phosphinyl group (—P(O)R$_3$R$_4$); a $C_6$-$C_{10}$ aryl group; a $C_3$-$C_{10}$ heteroaryl group and a $C_3$-$C_{10}$ heterocyclic group, $R_3$ and $R_4$ described above each independently contain at least one selected from the group consisting of hydrogen; a $C_1$-$C_6$ alkyl group; a $C_1$-$C_6$ alkenyl group; a $C_1$-$C_6$ alkynyl group; a $C_6$-$C_{10}$ aryl group; a $C_3$-$C_{10}$ heteroaryl group; and a $C_3$-$C_{10}$ heterocyclic group, and the $C_3$-$C_{10}$ heteroaryl group and the $C_3$-$C_{10}$ heterocyclic group contain at least one heteroatom selected from the group consisting of N, O, and S.

2. The compound according to claim 1, wherein $R^1$ and $R^2$ each independently represent hydrogen; a halogen atom selected from F and Cl; a methyl group; a substituted methyl group; a trifluoromethyl group; a $C_3$-$C_6$ heterocyclic group containing at least one heteroatom selected from O and N; or a $C_3$-$C_6$ heteroaryl group containing at least one heteroatom selected from 0 and N, the substituted methyl group contains at least one substituent selected from the group consisting of a $C_6$-$C_{10}$ aryl group; a $C_3$-$C_{10}$ heteroaryl group; and a $C_3$-$C_{10}$ heterocyclic group, and the $C_3$-$C_6$ heterocyclic group or the $C_3$-$C_6$ heteroaryl group contains a substituent of hydrogen or a $C_1$-$C_3$ alkyl group.

3. The compound according to claim 1, wherein, when X is —NH—, Y is —C(O)—, and when X is —C(O)—, Y is —NH—.

4. The compound according to claim 1, wherein the indazole-derived compound is selected from the group consisting of the following compound Nos. 1 to 16:

(Compound No. 1) N-(3-((3-amino-1H-indazol-4-yl)ethynyl)phenyl)-3-(trifluoromethyl)benzamide;

(Compound No. 2) 4N-(3-((3-amino-1H-indazol-4-yl)ethynyl)phenyl)-3,5-bis (trifluoromethyl)benzamide;

(Compound No. 3) N-(3-((3-amino-1H-indazol-4-yl)ethynyl)phenyl)-3-(4-methyl-1H-imidazol-1-yl)-5-(trifluoromethyl)benzamide;

(Compound No. 4) N-(3-((3-amino-1H-indazol-4-yl)ethynyl)phenyl)-3-fluoro-5-(trifluoromethyl)benzamide;

(Compound No. 5) N-(3-((3-amino-1H-indazol-4-yl)ethynyl)phenyl)-3-morpholino-5-(trifluoromethyl)benzamide;

(Compound No. 6) N-(3-((3-amino-1H-indazol-4-yl)ethynyl)phenyl)-4-methyl-3-(trifluoromethyl)benzamide;

(Compound No. 7) N-(3-((3-amino-1H-indazol-4-yl)ethynyl)phenyl)-4-(4-methylpiperazin-1-yl)-3-(trifluoromethyl)benzamide;

(Compound No. 8) N-(3-((3-amino-1H-indazol-4-yl)ethynyl)phenyl)-3,5-bis (trifluoromethyl)benzamide;

(Compound No. 9) 3-((3-amino-1H-indazol-4-yl)ethynyl)-N-(3-(trifluoromethyl)phenyl)benzamide;

(Compound No. 10) 3-((3-amino-1H-indazol-4-yl)ethynyl)-N-(3,5-bis(trifluoromethyl)phenyl)benzamide;

(Compound No. 11) 3-((3-amino-1H-indazol-4-yl)ethynyl)-N-(3-(4-methyl-1H-imidazol-1-yl)-5-(trifluoromethyl)phenyl)benzamide;

(Compound No. 12) 3-((3-amino-1H-indazol-4-yl)ethynyl)-N-(3-((4-methylpiperazin-1-yl)methyl)-5-(trifluoromethyl)phenyl)benzamide;

(Compound No. 13) 3-((3-amino-1H-indazol-4-yl)ethynyl)-N-(3-((4-methylpiperazin-1-yl)methyl)-5-(trifluoromethyl)phenyl)benzamide;

(Compound No. 14) 3-((3-amino-1H-indazol-4-yl)ethynyl)-N-(4-chloro-3-(trifluoromethyl)phenyl)benzamide;

(Compound No. 15) 3-((3-amino-1H-indazol-4-yl)ethynyl)-N-(4-((4-ethylpiperazin-1-yl)methyl)-3-(trifluoromethyl)phenyl)benzamide; and (Compound No. 16) 3-((3-amino-1H-indazol-4-yl)ethynyl)-N-(4-(morpholinomethyl)-3-(trifluoromethyl)phenylbenzamide.

5. The compound according to claim 1, wherein the pharmaceutically acceptable salt is a salt of an inorganic acid or organic acid selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

6. A pharmaceutical composition for alleviating or treating cancer comprising the compound according to claim 1 as an active ingredient, wherein the cancer is related with activity of at least one protein kinase of an ABL protein kinase, a T315I point mutation ABL protein kinase and a DDR1 protein kinase.

7. The pharmaceutical composition according to claim 6, wherein the pharmaceutical composition is administered to a cancer patient having at least one of an ABL gene, a T315I mutant ABL gene and a DDR1 gene.

8. The pharmaceutical composition according to claim 6, wherein the pharmaceutical composition inhibits activity of at least one protein kinase of an ABL protein kinase, a T315I point mutation ABL protein kinase and a DDR1 protein kinase.

9. The pharmaceutical composition according to claim 6, wherein the cancer is selected from the group consisting of blood cancer, lung cancer, breast cancer, stomach cancer, liver cancer, colon cancer, skin cancer, uterine cancer, brain cancer, laryngeal cancer, prostate cancer, bladder cancer, esophageal cancer, thyroid cancer, kidney cancer and rectal cancer.

10. The pharmaceutical composition according to claim 9, wherein the blood cancer is selected from the group consisting of chronic myelogenous leukemia, acute myelogenous leukemia, chronic lymphocytic leukemia or acute lymphocytic leukemia.

11. The pharmaceutical composition according to claim 10, wherein the blood cancer is chronic myelogenous leukemia.

12. A method of preparing a compound selected from a compound represented by the following Formula 1, a pharmaceutically acceptable salt thereof, a hydrate thereof and a stereoisomer thereof, the method comprising reacting a compound represented by the following Formula 2 with a compound represented by the following Formula 3 under the condition of a carbon-carbon bond formation reaction between the iodine group of Formula 2 and the alkynyl carbon of Formula 3:

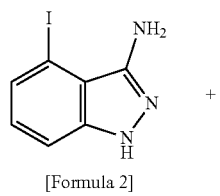

[Formula 2]

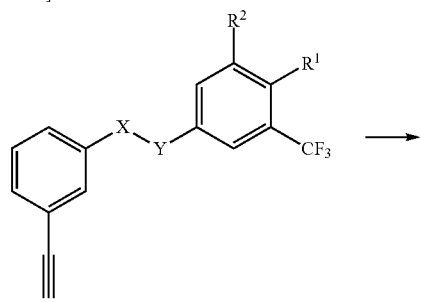

[Formula 3]

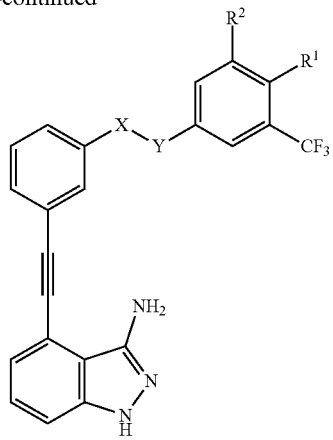

[Formula 1]

wherein $R^1$ and $R^2$ each independently represent hydrogen; a halogen atom; a $C_1$-$C_{13}$ alkyl group; a $C_3$-$C_{10}$ aryl group; a $C_3$-$C_{10}$ cyclic group; a $C_3$-$C_{10}$ heteroaryl group; and a $C_3$-$C_{10}$ heterocyclic group;

X and Y are each independently —NH—; or —C(O)—;

wherein the $C_1$-$C_{13}$ alkyl group or the $C_3$-$C_{10}$ cyclic group contains at least one substituent selected from the group consisting of hydrogen; a hydroxy group; a halogen group; a $C_1$-$C_{13}$ alkyl group; a $C_1$-$C_6$ alkoxy group; an amino group (—$NR_3R_4$); a nitro group (—$N(O)_2$); an amide group (—(C=O)$NR_3R_4$); a carboxyl group (—C(O)OH); a nitrile group (—CN); a urea group (—$NR_3$(C=O)$NR_4$—); a sulfonamide group (—NHS(O)$_2$—); a sulfide group (—S—); a sulfone group (—S(O)$_2$—); a phosphinyl group (—P(O)$R_3R_4$); a $C_6$-$C_{10}$ aryl group; a $C_3$-$C_{10}$ heteroaryl group; and a $C_3$-$C_{10}$ heterocyclic group, the $C_3$-$C_{10}$ aryl group, the $C_3$-$C_{10}$ heteroaryl group or the $C_3$-$C_{10}$ heterocyclic group contains at least one substituent selected from the group consisting of hydrogen; a hydroxy group; a halogen group; a carbonyl group (—(C=O)$R_3R_4$); a $C_1$-$C_3$ alkyl group substituted or unsubstituted with halogen or a $C_3$-$C_{10}$ heterocyclic group; a $C_1$-$C_3$ alkoxy group substituted or unsubstituted with halogen or a $C_3$-$C_{10}$ heterocyclic group; $C_6$-$C_{10}$ phenoxy; an amino group (—$NR_3R_4$); a nitro group (—$N(O)_2$); an amide group (—(C=O)$NR_3R_4$); a carboxyl group (—C(O)OH); a nitrile group (—CN); a urea group (—$NR_3$(C=O)$NR_4$—); a sulfonamide group (—NHS(O)$_2$—); a sulfide group (—S—); a sulfone group (—S(O)$_2$—); a phosphinyl group (—P(O)$R_3R_4$); a $C_6$-$C_{10}$ aryl group; a $C_3$-$C_{10}$ heteroaryl group and a $C_3$-$C_{10}$ heterocyclic group, $R_3$ and $R_4$ described above each independently contain at least one selected from the group consisting of hydrogen; a $C_1$-$C_6$ alkyl group; a $C_1$-$C_6$ alkenyl group; a $C_1$-$C_6$ alkynyl group; a $C_6$-$C_{10}$ aryl group; a $C_3$-$C_{10}$ heteroaryl group; and a $C_3$-$C_{10}$ heterocyclic group, and the $C_3$-$C_{10}$ heteroaryl group and the $C_3$-$C_{10}$ heterocyclic group contain at least one heteroatom selected from the group consisting of N, O, and S.

* * * * *